(12) United States Patent
Basude et al.

(10) Patent No.: US 11,648,118 B2
(45) Date of Patent: May 16, 2023

(54) TISSUE GRASPING DEVICES AND RELATED METHODS

(71) Applicants: Raghuveer Basude, Fremont, CA (US); Shri Krishna Basude, Fremont, CA (US)

(72) Inventors: Raghuveer Basude, Fremont, CA (US); Shri Krishna Basude, Fremont, CA (US)

(*) Notice: Subject to any disclaimer, the term of this patent is extended or adjusted under 35 U.S.C. 154(b) by 299 days.

(21) Appl. No.: 16/735,419

(22) Filed: Jan. 6, 2020

(65) Prior Publication Data

US 2020/0138569 A1     May 7, 2020

Related U.S. Application Data

(63) Continuation of application No. PCT/US2018/041016, filed on Jul. 6, 2018.

(60) Provisional application No. 62/529,373, filed on Jul. 6, 2017, provisional application No. 62/529,384, filed on Jul. 6, 2017, provisional application No. 62/529,389, filed on Jul. 6, 2017, provisional
(Continued)

(51) Int. Cl.
*A61F 2/24* (2006.01)

(52) U.S. Cl.
CPC ............ *A61F 2/246* (2013.01); *A61F 2/2463* (2013.01); *A61F 2/2466* (2013.01); *A61F 2210/0014* (2013.01); *A61F 2220/0008* (2013.01); *A61F 2250/0003* (2013.01); *A61F 2250/0051* (2013.01)

(58) Field of Classification Search
CPC ....... A61F 2/246; A61F 2/2463; A61F 2/2466
USPC .................................................. 623/2.1–2.19
See application file for complete search history.

(56) References Cited

U.S. PATENT DOCUMENTS 8,449,606 B2    5/2013   Eliasen et al.
9,414,918 B2    8/2016   Chau et al.
(Continued)

FOREIGN PATENT DOCUMENTS

JP    2006528034 A    12/2006
JP    2008514307 A    5/2008
(Continued)

OTHER PUBLICATIONS

EP18828922.7 Extended European Search Report dated Feb. 24, 2021.
(Continued)

*Primary Examiner* — Suzette J Gherbi
(74) *Attorney, Agent, or Firm* — Wilson Sonsini Goodrich & Rosati

(57) ABSTRACT

A prosthetic device for sealing a native heart valves to prevent or reduce regurgitation comprises a spacer having one or more anchors. The spacer may also have atrial support structures, ventricular support structures, or both atrial and ventricular support structures In some cases, the spacer has anchors that attach to the leaflets as well as atrial and ventricular support. In some cases, the spacer straddles the annulus and is located by anchors, and in some cases the support structures can be implanted within the native heart valve. In some cases, the prosthetic device reduces the annulus diameter when implanted within the native heart vasculature. In some cases, the prosthetic device cinches the annulus when implanted within the native heart vasculature.

11 Claims, 59 Drawing Sheets

Related U.S. Application Data application No. 62/529,392, filed on Jul. 6, 2017, provisional application No. 62/529,380, filed on Jul. 6, 2017.

(56) References Cited

U.S. PATENT DOCUMENTS

| | | | |
|---|---|---|---|
| 9,526,616 | B2 | 12/2016 | Nieminen et al. |
| 10,188,392 | B2* | 1/2019 | Wei .................. A61B 17/08 |
| 2005/0075713 | A1* | 4/2005 | Biancucci ............ A61F 2/2418 |
| | | | 623/1.11 |
| 2008/0228223 | A1 | 9/2008 | Alkhatib |
| 2009/0259306 | A1* | 10/2009 | Rowe .................... A61F 2/2433 |
| | | | 623/2.12 |
| 2010/0022823 | A1 | 1/2010 | Goldfarb et al. |
| 2010/0042208 | A1 | 2/2010 | Herrmann et al. |
| 2011/0004227 | A1 | 1/2011 | Goldfarb et al. |
| 2013/0338764 | A1 | 12/2013 | Thornton et al. |
| 2014/0067048 | A1 | 3/2014 | Chau et al. |
| 2014/0222136 | A1 | 8/2014 | Geist et al. |
| 2015/0273119 | A1 | 10/2015 | Heo et al. |
| 2018/0206984 | A1* | 7/2018 | Noe ....................... A61F 2/2409 |
| 2019/0030285 | A1 | 1/2019 | Prabhu et al. |
| 2020/0229806 | A1 | 7/2020 | Goldfarb et al. |
| 2020/0375732 | A1* | 12/2020 | Morriss ................. A61F 2/2403 |
| 2021/0000592 | A1* | 1/2021 | Christianson .......... A61F 2/2418 |
| 2021/0186686 | A1* | 6/2021 | Delgado ................ A61F 2/2418 |
| 2021/0346023 | A1* | 11/2021 | Krone .............. A61B 17/00234 |

FOREIGN PATENT DOCUMENTS

| | | |
|---|---|---|
| JP | 2016506794 A | 3/2016 |
| WO | WO-2004071336 A2 | 8/2004 |
| WO | WO-2019010370 A1 | 1/2019 |

OTHER PUBLICATIONS

PCT/US2018/041016 International Search Report and Written Opinion dated Sep. 25, 2018.

* cited by examiner

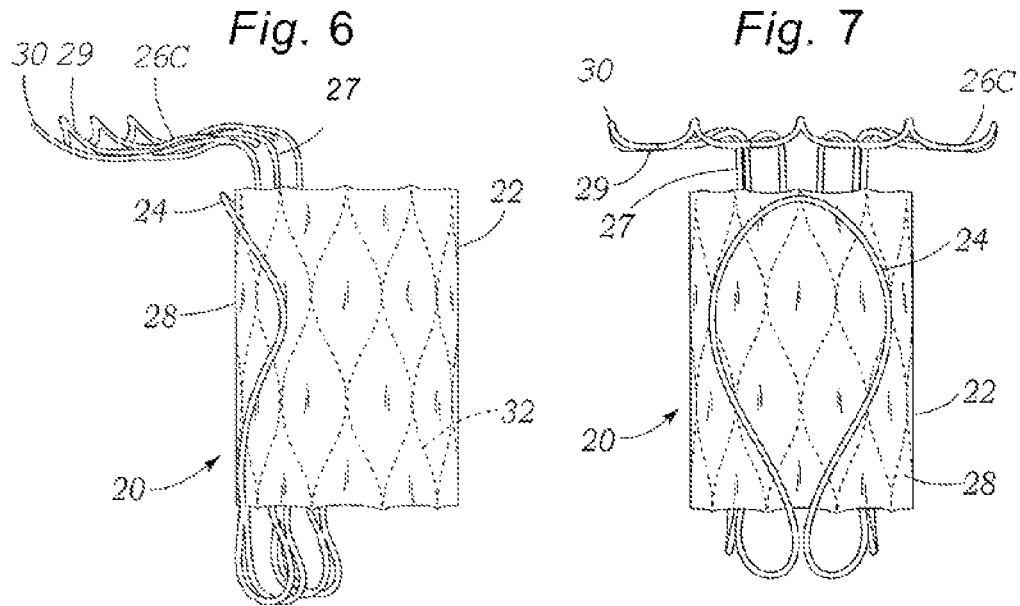
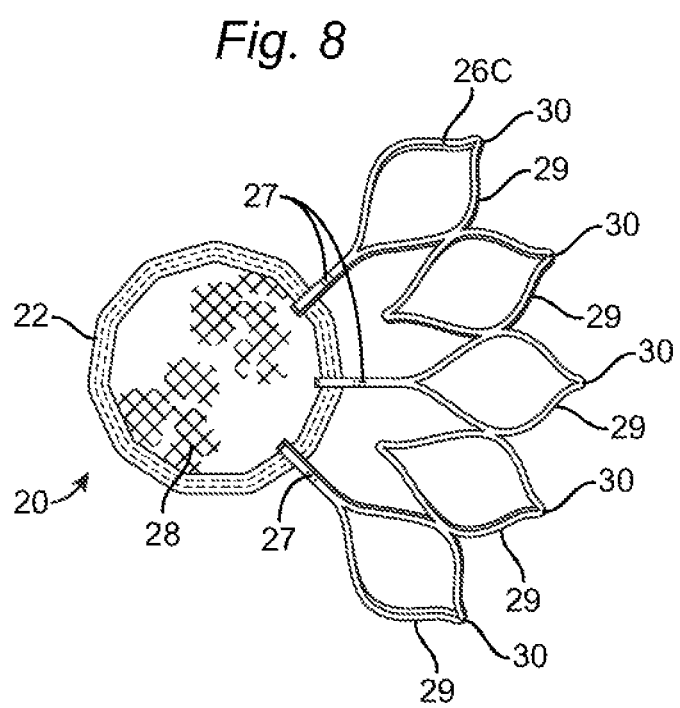

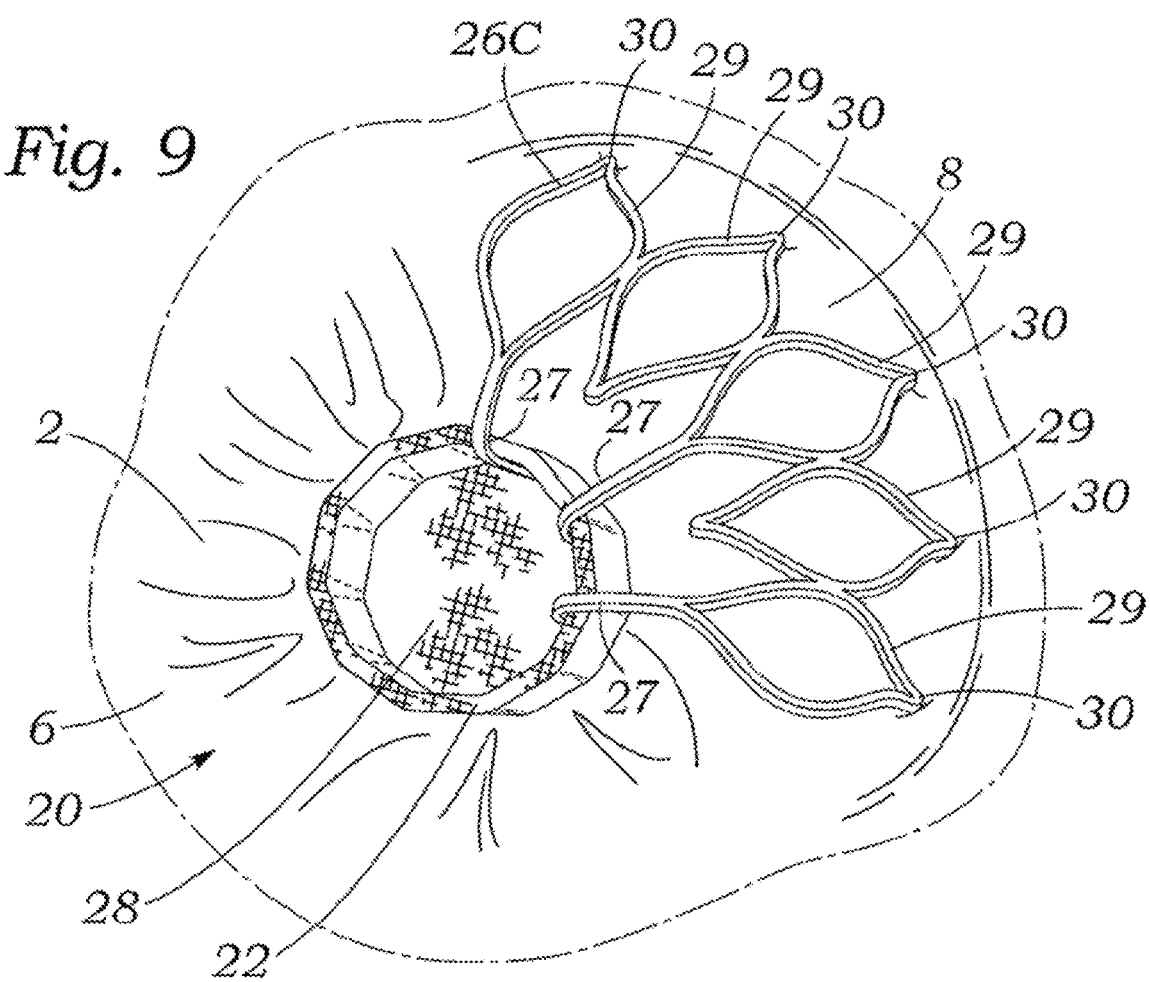

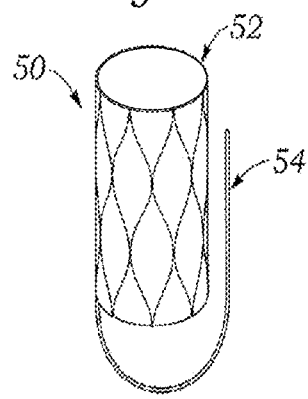
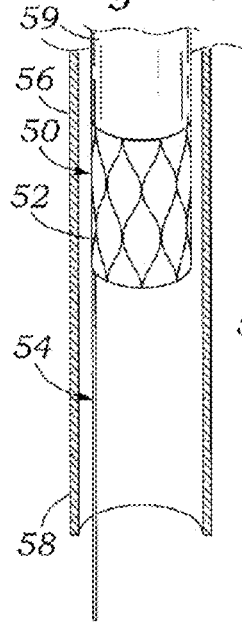 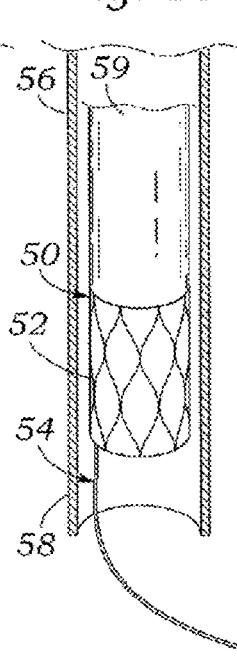 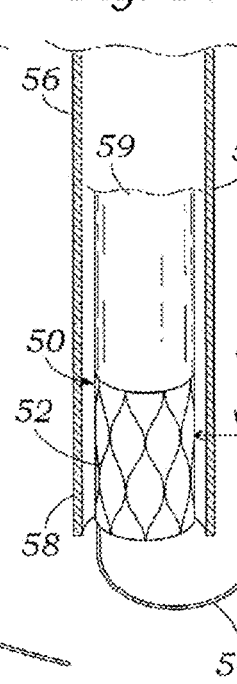 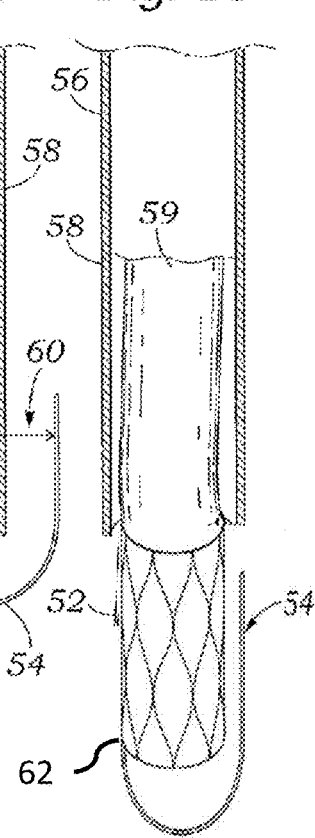

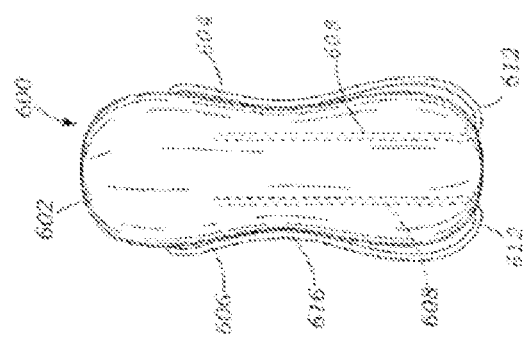
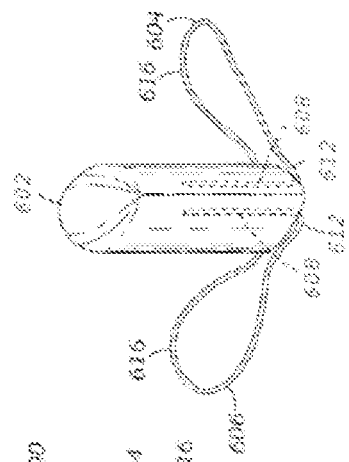
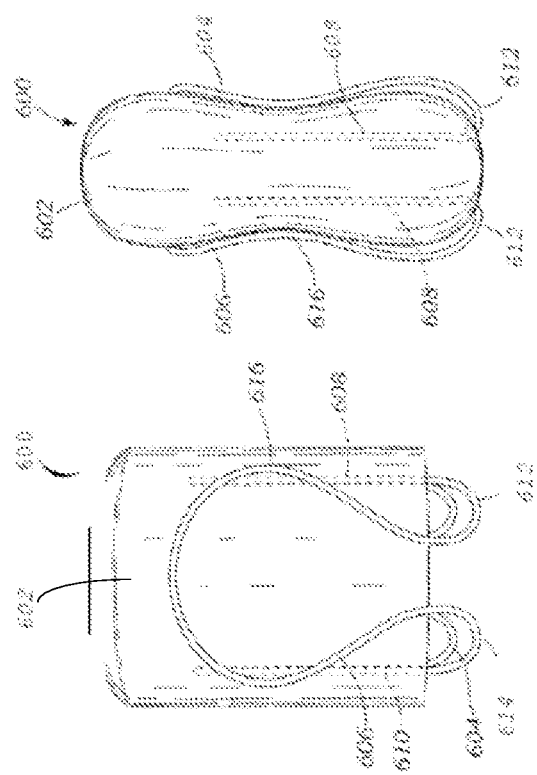
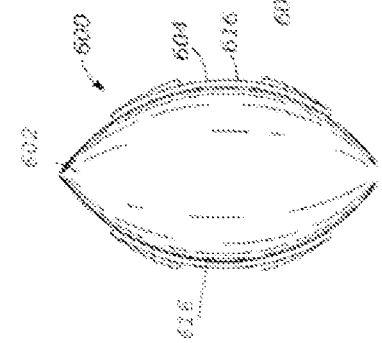

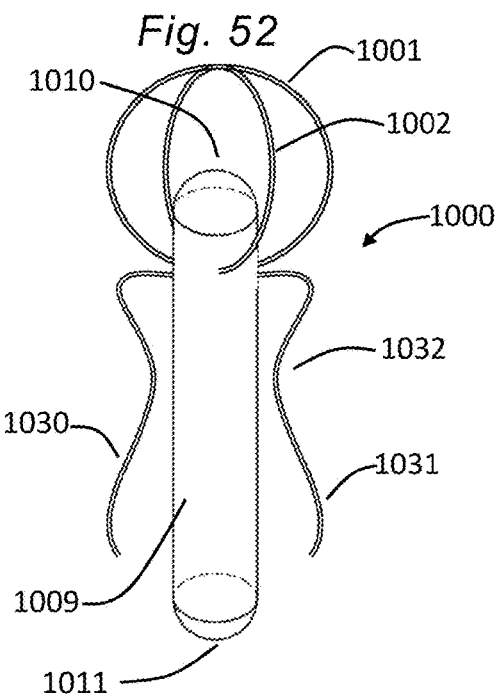
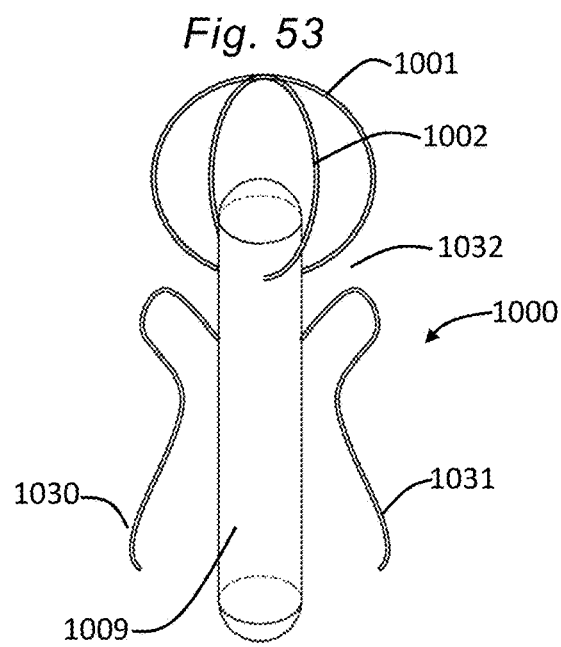
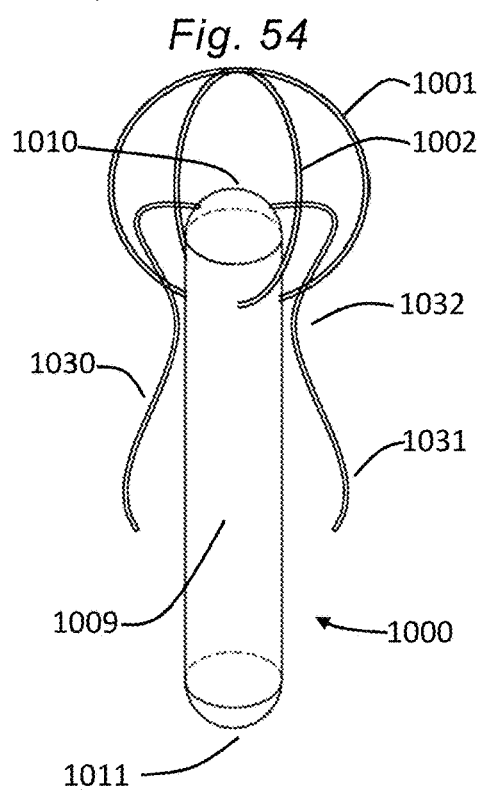
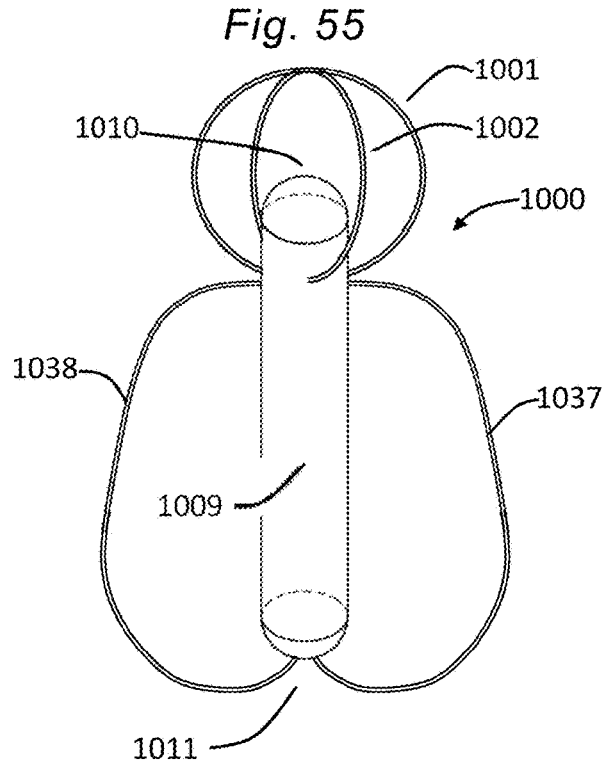

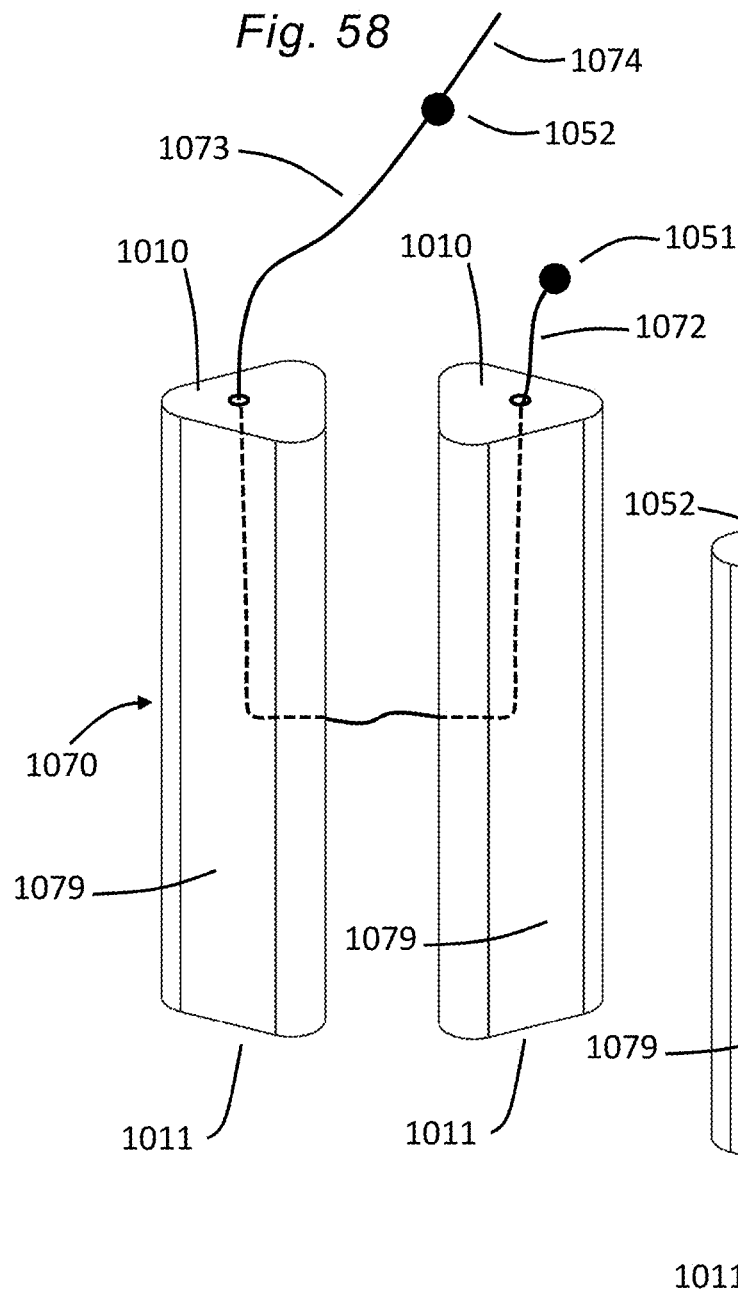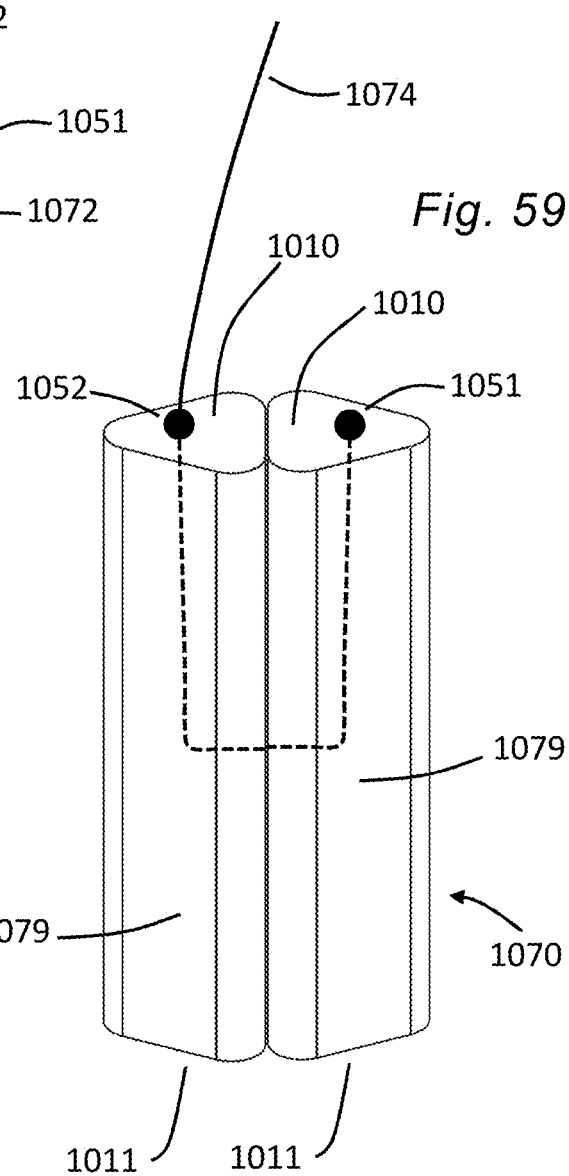

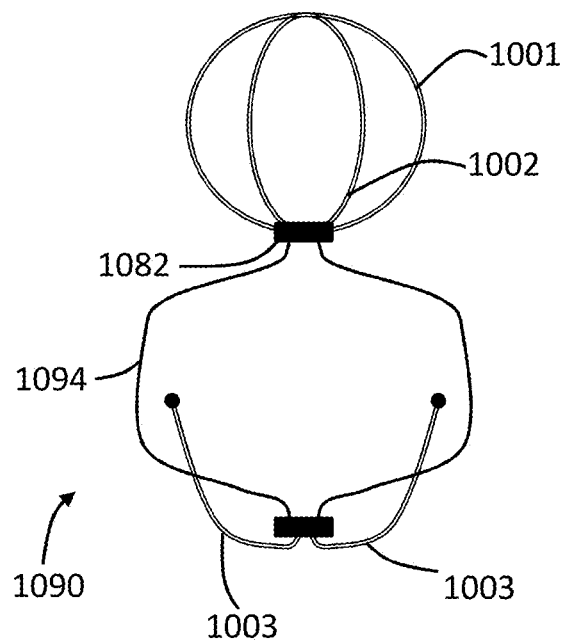
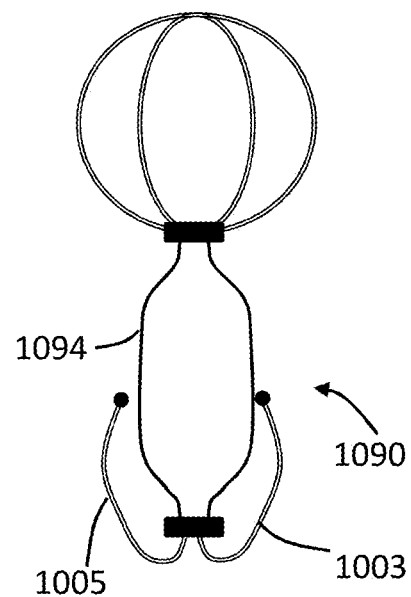
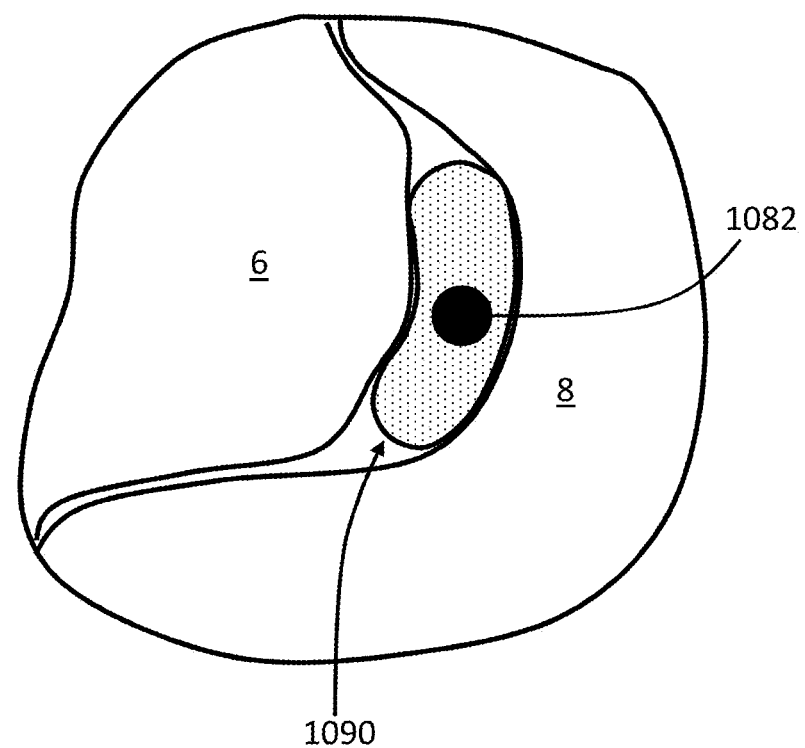

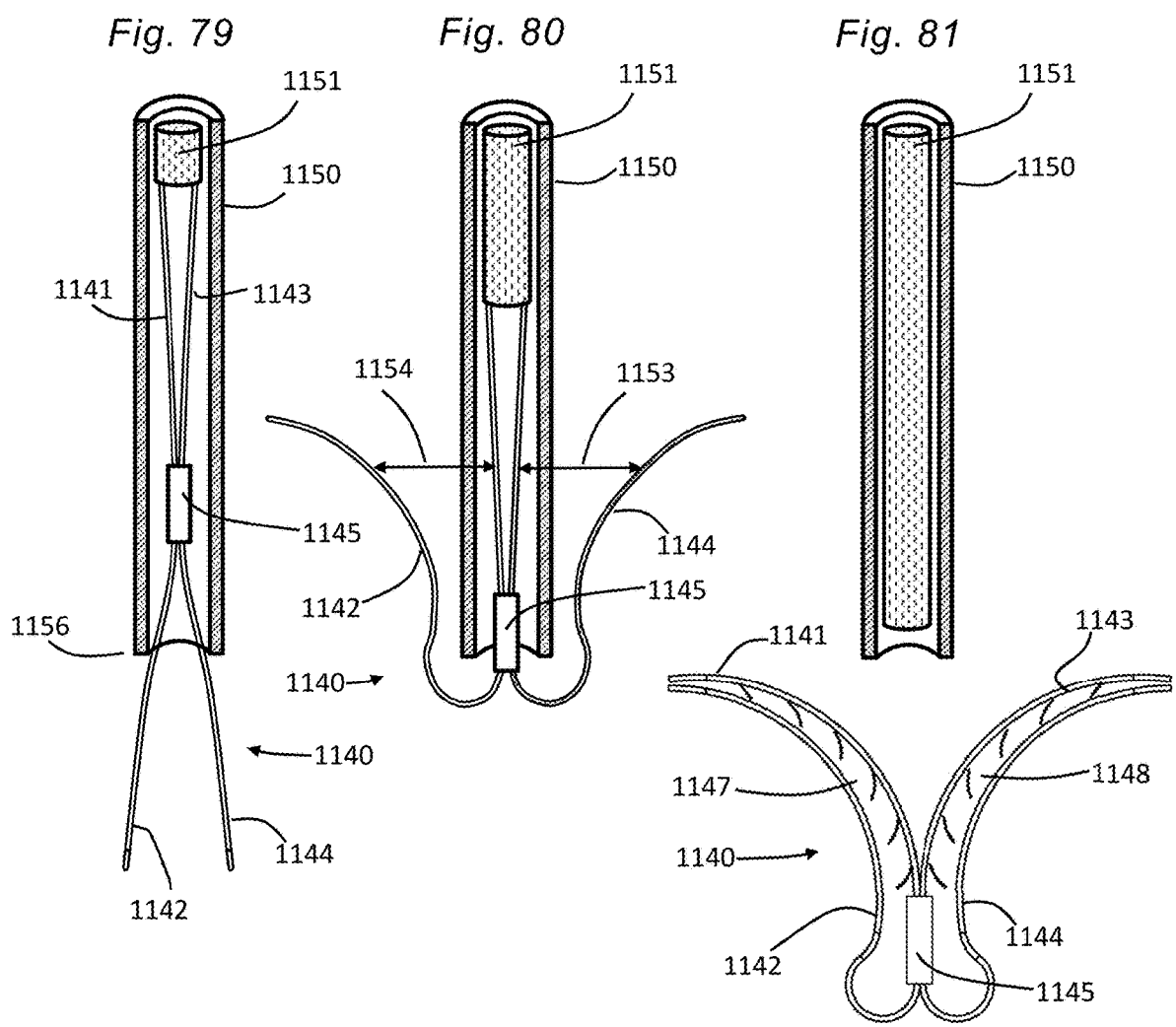

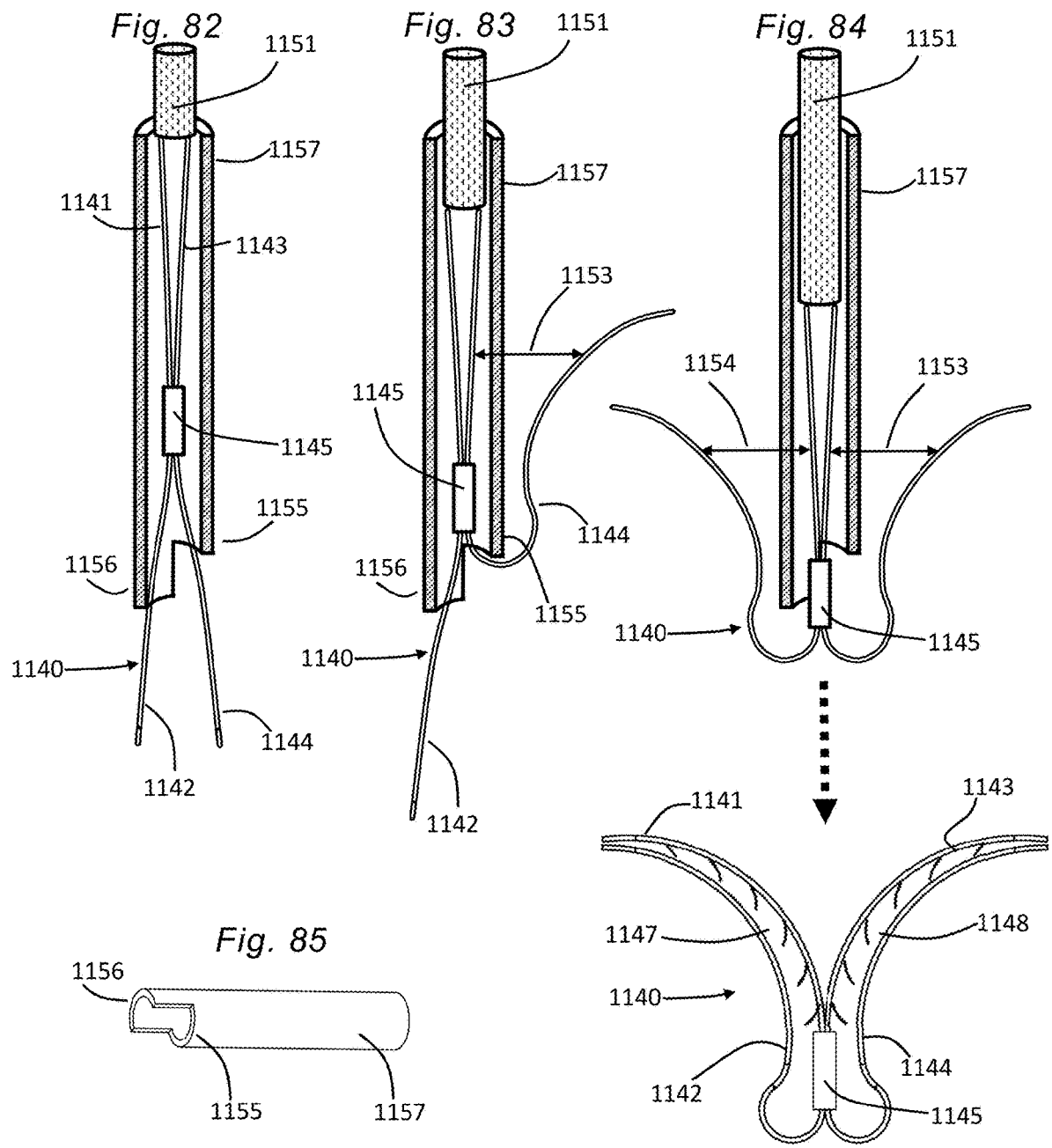

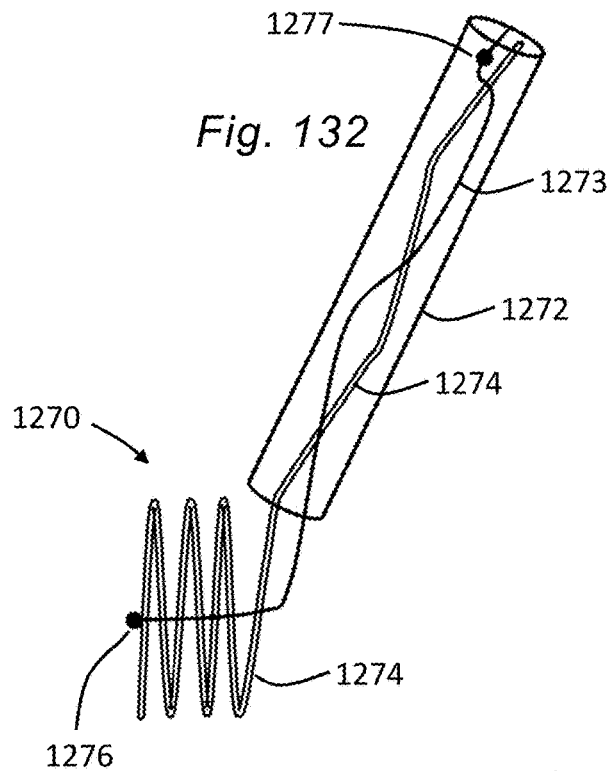
Fig. 132
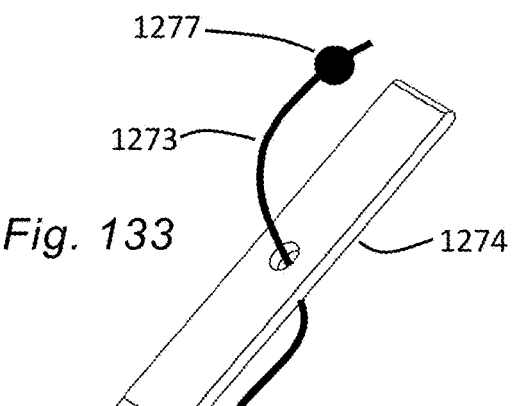
Fig. 133
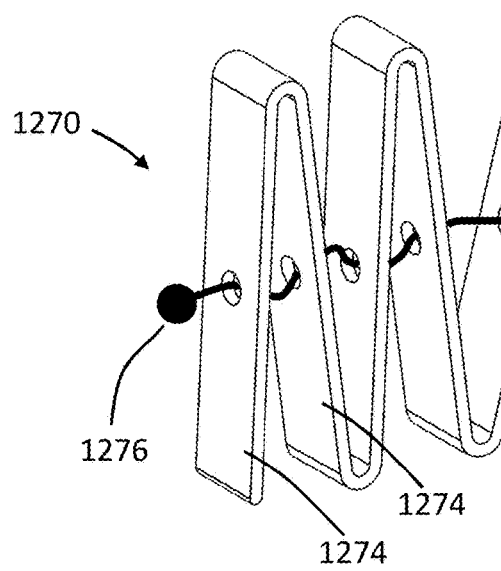
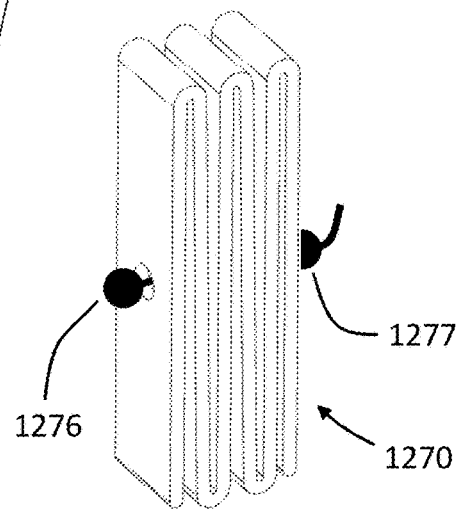
Fig. 134

TISSUE GRASPING DEVICES AND RELATED METHODS

CROSS REFERENCE TO RELATED APPLICATIONS

This application is a continuation of PCT Application No. PCT/US2018/041016, filed Jul. 6, 2018, which claims the benefit of provisional patent application nos. 62,529,373, filed Jul. 6, 2017; 62,529,384, filed Jul. 6, 2017; 62,529,389, filed Jul. 6, 2017; 62,529,392, filed Jul. 6, 2017; 62,529,380, filed Jul. 6, 2017.

BACKGROUND OF THE INVENTION

Field of the Invention. This application relates generally to medical devices and methods for repairing heart valves. More particularly, the present invention relates to methods and devices for the repair of mitral and tricuspid heart valves, venous valves, and other tissue structure through minimally invasive and other procedures.

The native heart valves (i.e., the aortic, pulmonary, tricuspid and mitral valves) serve critical functions in assuring the forward flow of an adequate supply of blood through the cardiovascular system. These heart valves can be rendered less effective by congenital malformations, inflammatory processes, infectious conditions or disease. Such damage to the valves can result in serious cardiovascular compromise or death. For many years, the definitive treatment for such disorders was the surgical repair or replacement of the valve during open heart surgery. However, such surgeries are highly invasive and are prone to many complications. Therefore, elderly and frail patients with defective heart valves often went untreated. More recently, transvascular techniques have been developed for introducing and implanting prosthetic devices in a manner that is much less invasive than open heart surgery. Such transvascular techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets extending downward from the annulus into the left ventricle. The mitral valve annulus can form a "D" shaped, oval, or otherwise out-of-round cross-sectional shape having major and minor axes. The anterior leaflet can be larger than the posterior leaflet, forming a generally "C" shaped boundary between the abutting free edges of the leaflets when they are closed together When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates, the oxygenated blood that is collected in the left atrium flows into the left ventricle. When the muscles of the left atrium relax and the muscles of the left ventricle contract, the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systole phase of heart contraction. Mitral regurgitation is the most common form of valvular heart disease. Mitral regurgitation has different causes, such as leaflet prolapse, dysfunctional papillary muscles and/or stretching of the mitral valve annulus resulting from dilation of the left ventricle. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Some prior techniques for treating mitral regurgitation include stitching portions of the native mitral valve leaflets directly to one another. The most common treatments for mitral valve regurgitation rely on valve replacement or repair including leaflet and annulus remodeling, the latter generally referred to as valve annuloplasty. Other prior techniques include the use of a spacer implanted between the native mitral valve leaflets. Despite these prior techniques, there is a continuing need for improved devices and methods for treating mitral valve regurgitation.

SUMMARY OF THE INVENTION

This invention provides apparatus, such as implants and prosthetic devices, and methods for fabrication, implanting, and using, such apparatus for sealing native heart valves to prevent or reduce regurgitation.

Spacers

1. Incompressible Body. In some embodiments, a prosthetic device for treating heart valve regurgitation comprises a radially incompressible and/or non-expandable body having a first end, a second end, and an outer surface extending from the first end to the second end and an anchor having a connection portion and a leaflet capture portion, wherein the connection portion is coupled to the body such that the leaflet capture portion is biased against the outer surface of the body when the body is in a radially expanded state, the prosthetic device is configured to capture a leaflet of a native heart valve between the leaflet capture portion of the anchor and the outer surface of the body, and the body is configured to prevent blood from flowing through the body in a direction extending from the first end to the second end and in a direction extending from the second end to the first end.

2. Incompressible Rigid Body. In some embodiments, a prosthetic device for treating heart valve regurgitation comprises a radially incompressible and rigid body having a first end, a second end, and an outer surface extending from the first end to the second end and an anchor having a connection portion and a leaflet capture portion, wherein the connection portion is coupled to the body such that the leaflet capture portion is biased against the outer surface of the body, the prosthetic device is configured to capture a leaflet of a native heart valve between the leaflet capture portion of the anchor and the outer surface of the body, and the body is configured to prevent blood from flowing through the body in a direction extending from the first end to the second end and in a direction extending from the second end to the first end.

3. Incompressible Flexible Body. In some embodiments, a prosthetic device for treating heart valve regurgitation comprises a radially incompressible and flexible body having a first end, a second end, and an outer surface extending from the first end to the second end and an anchor having a connection portion and a leaflet capture portion, wherein the connection portion is coupled to the body such that the leaflet capture portion is biased against the outer surface of the body, the prosthetic device is configured to capture a leaflet of a native heart valve between the leaflet capture portion of the anchor and the outer surface of the body, and the body is configured to prevent blood from flowing through the body in a direction extending from the first end to the second end and in a direction extending from the second end to the first end.

4. Anchorless Incompressible Body. In some embodiments, a prosthetic device for treating heart valve regurgitation comprises a radially incompressible and/or non-expandable body having a first end, a second end, and an outer surface extending from the first end to the second end and having a support portion, wherein the support portion is coupled to the body such that the leaflet positioned against the outer surface of the body such that some sliding movement may be present, however, in totality, the position of the body is configured to prevent blood from flowing through the body in a direction extending from the first end to the second end and in a direction extending from the second end to the first end.

5. Anchorless, Incompressible Rigid Body. In some embodiments, a prosthetic device for treating heart valve regurgitation comprises a radially incompressible and rigid body having a first end, a second end, and an outer surface extending from the first end to the second end and having a support portion, wherein the support portion is coupled to the body such that the leaflet positioned against the outer surface of the body such that some sliding movement may be present, however, in totality, the position of the body is configured to prevent blood from flowing through the body in a direction extending from the first end to the second end and in a direction extending from the second end to the first end.

6. Anchorless, Incompressible Flexible Body. In some embodiments, a prosthetic device for treating heart valve regurgitation comprises a radially incompressible and flexible body having a first end, a second end, and an outer surface extending from the first end to the second end and having a support portion, wherein the support portion is coupled to the body such that the leaflet positioned against the outer surface of the body such that some sliding movement may be present, however, in totality, the position of the body is configured to prevent blood from flowing through the body in a direction extending from the first end to the second end and in a direction extending from the second end to the first end.

7. Anchorless Freely Floating Compressible and Expandable Body. In some embodiments, a prosthetic device for treating heart valve regurgitation comprises an anchorless and radially compressible and radially expandable body having a first end, a second end, and an outer surface extending from the first end to the second end, wherein the outer surface when in a radially expanded state, comes in contact with the leaflet, and the body is configured to prevent blood from flowing through the body in a direction extending from the first end to the second end and in a direction extending from the second end to the first end, and configured to freely float within a confined space.

8. Anchorless, Retrievable, Freely Floating Compressible and Expandable Body. In some embodiments, a prosthetic device for treating heart valve regurgitation comprises an anchorless and radially compressible and radially expandable body having a first end, a second end, and an outer surface extending from the first end to the second end, wherein the outer surface when in a radially expanded state, comes in contact with the leaflet, and the body is configured to prevent blood from flowing through the body in a direction extending from the first end to the second end and in a direction extending from the second end to the first end, and configured to freely float relative to the native within a confined space, and is retrievable from either the first end or the second end and/or both ends.

9. Anchorless, Retrievable, Freely Floating Incompressible and Expandable Body. In some embodiments, a prosthetic device for treating heart valve regurgitation comprises an anchorless and radially incompressible and radially not expandable body having a first end, a second end, and an outer surface extending from the first end to the second end, wherein the outer surface when in a radially expanded state, comes in contact with the leaflet, and the body is configured to prevent blood from flowing through the body in a direction extending from the first end to the second end and in a direction extending from the second end to the first end, and configured to freely float relative to the native within a confined space, and is retrievable from either the first end or the second end or both ends.

10. Anchorless with Support Structures, Retrievable, Freely Floating Compressible and Expandable Body. In some embodiments, a prosthetic device for treating heart valve regurgitation comprises an anchorless and radially compressible and radially expandable body having a first end, a second end, and an outer surface extending from the first end to the second end, and having support structures that extend in the atrium or ventricle or both, wherein the outer surface when in a radially expanded state, comes in contact with the leaflet, and the body is configured to prevent blood from flowing through the body in a direction extending from the first end to the second end and in a direction extending from the second end to the first end, and configured to freely float relative to the native valves within a confined space as defined by the support structures.

11. Valve and Flow Around. In some embodiments, the body is non-radially compressible to a compressed state in which a leaflet-receiving gap exists between the body and the leaflet capture portion of the anchor, and the body is resiliently self-expandable to the expanded state. In some embodiments, the anchor comprises a first clip portion and a second clip portion, and the device is configured to capture the leaflet between the first and second clip portions. In some embodiments, the body is formed from Nitinol and is non-radially self-expandable to the expanded state. In some embodiments, the body comprises a metallic frame and a blood-impermeable fabric mounted on the frame. In some embodiments, the body is configured to allow blood to flow from atrium to the ventricle both through the artificial valve and around the body between the body and a non-captured leaflet during diastole, and configured to allow the non-captured leaflet to close around the body to prevent mitral regurgitation during systole.

12. Anchor. In some embodiments, the outer surface of the body comprises a first side against which the anchor is biased and a second side opposite the first side, and the connection portion of the anchor is coupled to the body on the second side of the body. In some embodiments, the anchor comprises an elongated member that is coupled to the second side of the body at a connection location and the elongated member comprises a ventricular portion that extends from the connection location across the first end of the body. In some embodiments, the ventricular portion comprises first and second ventricular portions and the first ventricular portion is substantially parallel to the second ventricular portion.

13. Atrial Stabilization, Shapes. In some embodiments, the anchor is coupled to the first end of the body and the device further comprises an atrial stabilizing member extending from the second end of the body. In some embodiments, the body is configured to move within the native heart valve along with motion of the captured leaflet. In some embodiments, an atrial end portion of the body comprises a tapered shoulder that reduces in diameter moving toward the atrial end portion of the body. In some embodiments, the body comprises a crescent cross-sectional shape. In some embodiments, the body comprises a dog-bone shape. In some embodiments the atrial or ventricular section forms a loop or configured to a shape so as to limit the movement of the body. In some embodiments, the body comprises a flattened oval shape. In some embodiments, the anchor comprises first and second anchors and the device is configured to be secured to both native mitral valve leaflets.

In some embodiments, a prosthetic device for treating heart valve regurgitation comprises a main body portion having a connection portion and a free end portion, wherein the connection portion is configured to be coupled to a first one of the two native mitral valve leaflets such that the device is implanted within a native mitral valve orifice, and when the device is implanted within the native mitral valve orifice, the free end portion moves laterally toward a second one of the two native mitral valve leaflets during systole, thereby helping to seal the orifice and reduce mitral regurgitation during systole, and the free end portion moves laterally away from the second native mitral valve leaflet during diastole to allow blood to flow from the left atrium to the left ventricle during diastole.

In some embodiments, the connection portion of the main body is thicker than the free end portion. In some embodiments, the main body portion further comprises an atrial portion that contacts the native mitral valve annulus within the left atrium adjacent to the first native mitral valve leaflet. In some embodiments, the device further comprises a ventricular anchor that clips around a lower end of the first native mitral valve leaflet, thereby securing the device to the first native mitral valve leaflet. In some embodiments, the anchor comprises a paddle shape with a broad upper end portion and a relatively narrow neck portion, wherein the neck portion couples the upper end portion to the main body. In some embodiments either the anchor or the body have traumatic and/or atraumatic barbs to stabilize the device. In some embodiments, the body is made of in inflatable balloon.

14. Leaf-Springs. In some preferred embodiments, the devices, systems and methods of the invention are adapted for fixation of tissue at a treatment site. Exemplary tissue fixation applications include cardiac valve repair, septal defect repair, vascular ligation and clamping, laceration repair and wound closure, but the invention may find use in a wide variety of tissue approximation and repair procedures. In a particularly preferred embodiment, the devices, systems and methods of the invention are adapted for repair of cardiac valves, and particularly the mitral valve, as a therapy for regurgitation. The invention enables two or more valve leaflets to be coapted using an "edge-to-edge" or "bow-tie" technique to reduce regurgitation, yet does not require open surgery through the chest and heart wall as in conventional approaches. In addition, the position of the leaflets may vary in diseased mitral valves depending upon the type and degree of disease, such as calcification, prolapse or flail. These types of diseases can result in one leaflet being more mobile than the other (e.g. more difficult to capture), and therefore more difficult to grasp symmetrically in the same grasp with the other leaflet. The features of the present invention allow the fixation devices to be adapted to meet the challenges of unpredictable target tissue geometry, as well as providing a more robust grasp on the tissue once it is captured. The present invention comprises of features that allow the implant to be retrieved post implantation. Additionally, the invention optionally incorporates known and typical visualization techniques to enable the device placement procedure to be performed without the use of general anesthesia.

The devices, systems and methods of the invention are centered on variety of devices which may be used individually or in a variety of combinations to form interventional systems. In preferred embodiments, the interventional system includes a multi-catheter guiding system, a delivery catheter and an interventional device. Each of these components will be discussed herein.

In an exemplary embodiment, the invention provides a fixation device having a pair of outer arms (or fixation elements), each outer arm having a free end and an engagement surface for engaging the tissue, wherein the outer arms are moveable between a first position for capturing the tissue and a second position for fixing the tissue. Preferably, the engagement surfaces are spaced apart in the first position and are closer together and generally face toward each other in the second position. The fixation device is preferably delivered to a target location in a patient's body by a delivery catheter having an elongated shaft, a proximal end and a distal end, the delivery catheter being configured to be positioned at the target location from a remote access point such as a vascular puncture or cut-down or a surgical penetration. In a preferred embodiment, the target location is a valve in the heart.

A particular advantage of the present invention is its ability to coapt the leaflets of the mitral valve (or any other tissue with which it is used) in a parallel or vertical relationship as well as grasp the leaflets along its anatomical profile. In other words, even with minimal or no coaptation depth, the leaflets may be captured, drawn together and fixed such that their proximal upstream surfaces are disposed parallel to each other and generally aligned with the direction of flow through the valve at the point of coaptation. In some embodiments of the fixation device, the use of sufficiently rigid outer arms, highly frictional and compressive inner arms and a passive closure mechanism enables the leaflets to be grasped in a spaced-apart relationship and then drawn together in a coapted relationship while keeping the leaflets vertical (aligned with blood flow) to achieve the optimal coapted configuration.

A particular advantage of the present invention is its ability to coapt the leaflets of the mitral valve (or any other tissue with which it is used) in a close anatomical relationship of the leaflet shape, while grasping alongside the anatomical contours of the leaflets. In other words, the leaflets may be captured, drawn together and fixed such that their natural anatomical shape is retained. In some embodiments of the fixation device, the use of sufficiently flexible outer arms, highly frictional and compressive inner arms and a passive closure mechanism enables the leaflets to be grasped in a spaced-apart relationship and then drawn together in a coapted relationship while keeping the leaflets vertical (aligned with blood flow) to achieve the optimal coapted configuration.

The fixation device is preferably delivered with the outer arms in a delivery position configured to minimize the profile of the device. When approaching the mitral valve from the atrial side, some embodiments of the fixation device allow the device to be delivered with the free ends of the outer arms pointing in a generally proximal direction forming an angle of less than about 90°, preferably less than about 20°, relative to the longitudinal axis of the delivery device shaft, so as to be able to grasp the leaflets from the ventricular side. In this position the engagement surfaces are facing generally toward each other, being disposed at an angle of less than about 180°, and preferably less than about 40°, relative to each other. For ventricular approaches, in the delivery position the free ends of the outer arms are pointing in a generally distal direction and form an angle of less than about 90°, preferably less than about 20° relative to the longitudinal axis of the delivery device shaft, so as to be able to grasp the leaflets from the ventricular side. In this position, the engagement surfaces are facing generally toward each other, usually being disposed at an angle of less than about 180°, and preferably less than about 90°, relative to each other. Alternatively, in some ventricular approaches, it may be preferred to have the free ends of the fixation elements pointing in a generally proximal direction and the engagement surfaces facing away from each other in the delivery position.

In order to provide for the reversibility and removability of the devices and systems of the invention, the leaflets are lifted off the sufficiently flexible arms using sutures or wires and/or the catheter. In mitral repair applications, this is particularly important due to the presence of chordae tendineae, valve leaflets and other tissues with which devices may become entangled. For approaches from the atrial side of the mitral valve (in the inverted position), the free ends will be pointing in a generally distal direction relative to the catheter shaft and the engagement surfaces will be facing generally away from each other, usually being disposed at an angle of more than about 180°, and preferably more than 270° relative to each other. For ventricular approaches to the valve in the mimicked inverted position, the free ends will be pointing in a distal direction relative to the catheter shaft and the engagement surfaces will be facing generally toward each other, usually being disposed at an angle of less than about 180°, and preferably less than 90° relative to each other. This, with the intent to invert and disengage the arms In the open position the engagement surfaces of the outer arms preferably form an angle of up to 180° relative to each other so as to maximize the area in which to capture the valve leaflets or other target tissue. The outer arms are preferably flexible to a closed position in which the engagement surfaces engage each other or form an angle as small as 0° relative to each other. The distal arms are configured to be flexible and left permanently in any of various positions while exerting a compressive force opposing the proximal arms to allow for the fixation of tissues of various thickness, geometry, and spacing.

A particular advantage of this invention is that both outer and inner arms are sufficiently superelastic and flexible to exert persistent and gentle opposing forces on the tissue, while allowing for small movements to conform with a) anatomical shape of the leaflet and b) physiological forces on the leaflets.

Another particular advantage of this invention is that the frictional elements (barbs) are placed medially along the long axis of the arm body and confined by continuous and solid side surface. Unlike in the MitraClip® device, the barbs are not exposed along the sides. This is advantageous as it significantly reduces the risk of entanglement of chordae tendineae, valve leaflets and other tissues with which devices may become entangled. Further, this feature reduces the risk of entanglement or sutures or wires or other such delivery catheter elements that may potentially come in contact with the fixation device.

One aspect of the invention provides a tissue shaping device adapted to be deployed in a vessel to reshape tissue adjacent the vessel. In an exemplary embodiment the device comprises of a leaf-spring like apposing features to engage the leaflet from atrial and ventricular sides. Two such leaf-spring features may be connected at the base to grasp each of the posterior and anterior leaflets of a mitral valve. In some embodiments, the above leaf-springs can be made of sheet metal and/or wire and/or strips and/or any other suitable material form. In some embodiments, the leaf-springs can have anchors and/or barbs to grasp and/or restrain the captured tissue/leaflets.

In some embodiments, the leaf-springs are configured to cinch the annulus in addition to restraining the leaflets to better mitigate regurgitation.

In some embodiments the opposing leaf springs can be formed from a combination of wires and/or sheet metal and/or strips and/or solid and/or hollow forms, with or without cut patterns.

In some embodiments, the leaf springs can be expandable and/or compressible, such that they can be in a compressed configuration in the delivery system and be deployed in an expanded configuration.

In some embodiments, the catheter shafts may be used to manipulate the features of the leaf-springs to capture the leaflets.

In some embodiments, the catheter may use sutures or wires or any other prevalent technique commonly used in the interventional catheter technology to manipulate the leaf-springs to either capture both leaflets at the same time or sequentially capture leaflets.

In some embodiments, only one apposing leaf-spring may used instead of a pair of opposing leaf-springs. This, to capture only one leaflet (anterior or posterior leaflet), while the other leaflet is free.

In some embodiments, a non-captured one of the anterior and posterior mitral valve leaflets is not secured to the sealing device when the prosthetic sealing device is implanted at the native mitral valve.

In some embodiments, advancing a delivery device to a native mitral valve region via a left ventricle comprises inserting the delivery device into the left ventricle through an incision in an apex of the left ventricle.

In some embodiments, advancing the delivery system to the native mitral valve region from the left ventricle comprises inserting the delivery device into the left ventricle through an incision in an apex of the left ventricle.

In some embodiments, when the delivery system is advanced to the native mitral valve region of the heart, the anchor is held in a substantially straightened position within the delivery catheter extending distally along a side of the body of the prosthetic sealing device.

In some embodiments, a method of implanting a prosthetic sealing device at a native mitral valve of a heart comprises of advancing a delivery system to a native mitral valve region of a heart from a left atrium of the heart, the delivery system housing the prosthetic sealing device, proximally retracting an outer sheath of the delivery system such that anchors of the prosthetic sealing device are not confined within the delivery system, retracting the delivery system toward the left atrium of the heart such that native mitral valve leaflets are positioned between the anchors of the prosthetic sealing device and the delivery system, proximally retracting an inner sheath of the delivery system such that a body of the prosthetic sealing device is not confined within the delivery system, wherein the body is configured to prevent the flow of blood through the body during systole and during diastole, and removing the delivery system from the native mitral valve region of the heart.

In some embodiments, advancing the delivery system to the native mitral valve region from the left atrium comprises advancing the delivery system through an incision in a portion of a septum between the left atrium and a right atrium. In some embodiments, when the delivery system is advanced to the native mitral valve region of the heart, the device is held in a substantially straightened position within the delivery catheter extending proximally from body of the prosthetic sealing device.

15. Spacer Leaf-spring. In other aspects, the present invention provides prosthetic devices and related methods for helping to seal native heart valves and prevent or reduce regurgitation therethrough, as well as devices and related methods for implanting such prosthetic devices.

One aspect of the invention provides a tissue shaping device adapted to be deployed in a vessel to reshape tissue adjacent the vessel. In an exemplary embodiment the device comprises of a leaf-spring and spacer like features to engage the leaflet from atrial and ventricular sides. Two such leaf-spring features may be connected at the base and/or apex to grasp each of the posterior and anterior leaflets of a mitral valve. Further, the invention emulates Alfieri edge-to-edge valve repair in combination with a spacer to mitigate regurgitation.

In some embodiments, the above leaf-springs can be made of sheet metal and/or wires. In some embodiments, the leaf-spring can be made of elastic and/or superelastic metals or polymers and/or ceramics.

In some embodiments, a prosthetic device comprises of leaf springs configured to be implanted within a native mitral valve orifice and coupled to a first one of the two native mitral leaflets or to the native mitral annulus adjacent the first native mitral leaflet, or freely float wherein, when implanted the device is configured to fill the space between the two coapting leaflets, such that a free portion of the assembled device not coupled to the first native mitral leaflet or the mitral annulus adjacent the first native mitral leaflet moves laterally toward and seals against the second of the two native mitral leaflets to reduce mitral regurgitation, and during diastole the portion of the device not coupled to the first native mitral leaflet or the native mitral annulus adjacent the first native mitral leaflet moves laterally away from the second native mitral leaflet to allow blood to flow from the left atrium to the left ventricle.

In some embodiments, the assembled segmented sheet comprises of a ventricular and/or atrial anchors or support structures that is configured to position the device between the said native mitral leaflet via direct contact with either the native valves or using atrial or ventricular walls, so as to reduce regurgitation.

In some embodiments, a ventricular end of the assembled sheet is tethered to a location in the left ventricle below the native mitral leaflets. In some embodiments, the lower end of the assembled sheet is tethered to the papillary muscle heads in the left ventricle. In some embodiments, the assembled sheet has a generally trapezoidal shape, with a broader portion adjacent to the mitral annulus and a narrower portion positioned between the native mitral leaflets.

In some embodiments, the atrial end of the assembled sheet is tethered to a location in the left atrium above the native mitral leaflets. In some embodiments, the assembled sheet has a generally trapezoidal shape, with a narrower portion at the mitral annulus and a broader portion positioned above and/or below the annulus.

In some embodiments, a non-captured one of the anterior and posterior mitral valve leaflets is not secured to the sealing device when the prosthetic sealing device is implanted at the native mitral valve.

In some embodiments, advancing a delivery device to a native mitral valve region via a left ventricle comprises inserting the delivery device into the left ventricle through an incision in an apex of the left ventricle.

In some embodiments, advancing the delivery system to the native mitral valve region from the left atrium comprises inserting the delivery device through an incision in the left atrium.

In some embodiments, when the delivery system is advanced to the native mitral valve region of the heart, the ventricular anchor is held in a substantially straightened position within the delivery catheter extending distally along a side of the body of the prosthetic sealing device.

In some embodiments, a method of implanting a prosthetic sealing device at a native mitral valve of a heart comprises advancing a delivery system to a native mitral valve region of a heart from a left atrium of the heart, the delivery system housing the prosthetic sealing device, proximally retracting an outer sheath of the delivery system such that anchors of the prosthetic sealing device are not confined within the delivery system, retracting the delivery system toward the left atrium of the heart such that native mitral valve leaflets are positioned between the anchors of the prosthetic sealing device and the delivery system, proximally retracting an inner sheath of the delivery system such that a body of the prosthetic sealing device is not confined within the delivery system, wherein the body is configured to prevent the flow of blood through the body during systole and during diastole, and removing the delivery system from the native mitral valve region of the heart.

In some embodiments, advancing the delivery system to the native mitral valve region from the left atrium comprises advancing the delivery system through an incision in a portion of a septum between the left atrium and a right atrium. In some embodiments, when the delivery system is advanced to the native mitral valve region of the heart, the anchor is held in a substantially straightened position within the delivery catheter extending proximally from body of the prosthetic sealing device.

16. Spacer Sheet. In other aspects, the present invention provides prosthetic devices and related methods for helping to seal native heart valves and prevent or reduce regurgitation therethrough, as well as devices and related methods for implanting such prosthetic devices.

In some embodiments, a prosthetic device comprises of segmented sheets configured to be assembled within the heart chambers and implanted within a native mitral valve orifice and coupled to a first one of the two native mitral leaflets or to the native mitral annulus adjacent the first native mitral leaflet, or freely float wherein when implanted, the sheet is configured to fill the space between the two coapting leaflets, such that a free portion of the assembled sheet not coupled to the first native mitral leaflet or the mitral annulus adjacent the first native mitral leaflet moves laterally toward and seals against the second of the two native mitral leaflets to reduce mitral regurgitation, and during diastole the portion of the sheet not coupled to the first native mitral leaflet or the native mitral annulus adjacent the first native mitral leaflet moves laterally away from the second native mitral leaflet to allow blood to flow from the left atrium to the left ventricle.

In some embodiments, a prosthetic device comprises of segmented sheets configured to be assembled within the heart chambers and implanted within a native mitral valve orifice and coupled to the two native mitral leaflets, wherein when implanted the sheet is configured to fill the space between the two coapting leaflets, such that the assembled sheet seals mitral regurgitation during systole.

In some embodiments, the assembled segmented sheet comprises a ventricular and/or atrial anchors or support structures that is configured to position the device between the said native mitral leaflet via direct contact with either the native valves or atrial or ventricular walls, so as to reduce regurgitation.

In some embodiments, a lower end of the assembled sheet is tethered to a location in the left ventricle below the native mitral leaflets. In some embodiments, the lower end of the assembled sheet is tethered to the papillary muscle heads in the left ventricle. In some embodiments, the upper end is tethered to the atrial wall. In some embodiments, the assembled sheet has a generally trapezoidal shape, with a broader portion adjacent to the mitral annulus and a narrower portion positioned between the native mitral leaflets.

In some embodiments, a non-captured one of the anterior and posterior mitral valve leaflets is not secured to the sealing device when the prosthetic sealing device is implanted at the native mitral valve.

In some embodiments, advancing a delivery device to a native mitral valve region via a left ventricle comprises inserting the delivery device into the left ventricle through an incision in an apex of the left ventricle.

In some embodiments, when the delivery system is advanced to the native mitral valve region of the heart, the anchor is held in a substantially straightened position within the delivery catheter extending distally along a side of the body of the prosthetic sealing device.

In some embodiments, a method of implanting a prosthetic sealing device at a native mitral valve of a heart comprises advancing a delivery system to a native mitral valve region of a heart from a left atrium of the heart, the delivery system housing the prosthetic sealing device, proximally retracting an outer sheath of the delivery system such that anchors of the prosthetic sealing device are not confined within the delivery system, retracting the delivery system toward the left atrium of the heart such that native mitral valve leaflets are positioned between the anchors of the prosthetic sealing device and the delivery system, proximally retracting an inner sheath of the delivery system such that a body of the prosthetic sealing device is not confined within the delivery system, wherein the body is configured to prevent the flow of blood through the body during systole and during diastole, and removing the delivery system from the native mitral valve region of the heart.

In some embodiments, advancing the delivery system to the native mitral valve region from the left atrium comprises advancing the delivery system through an incision in a portion of a septum between the left atrium and a right atrium. In some embodiments, when the delivery system is advanced to the native mitral valve region of the heart, the anchor is held in a substantially straightened position within the delivery catheter extending proximally from body of the prosthetic sealing device.

17. Annulus Reshaping Device. In other aspects, the present invention provides a tissue shaping device (such as a percutaneous mitral valve annuloplasty device) adapted to be deployed in a vessel to reshape tissue adjacent the vessel. The device comprises a first frictional member (or distal anchors or barbs) and a second frictional member (or proximal anchors or barbs) adapted to be deployed by a catheter to engage a vessel wall, wherein the device includes a leaf-spring feature adapted to engage the two frictional members and provide a support structure disposed between and operatively connecting the first frictional member and the second frictional member while providing the ability to cinch the annulus with sufficient surface area to distribute the cinching force to mitigate the cheese cutter effect. In some embodiments, the leaf spring support structure can additionally be configured to exert a radial compressive force on the annulus. In some embodiments, the frictional members are barbs that are configured to atraumatically engage with the tissue. In some embodiments, there may be intermediate frictional members in between the first and second frictional members to further augment engagement with tissue. In some embodiments, the frictional members are adapted to engage a coronary sinus. In some embodiments, the frictional members are adapted to engage a coronary sinus and the entire device (including the leaf spring) is configured to reshape the annulus to mitigate mitral valve regurgitation.

In some embodiments of the invention provides a tissue shaping device (such as a percutaneous mitral valve annuloplasty device) adapted to be deployed in a vessel to reshape tissue adjacent the vessel. The device comprises a first anchor and a second anchor and a telescoping leaf spring, that can be adapted to be deployed by a catheter to engage a vessel wall. The two anchors can be reversibly engaged or disengaged atraumatically during deployment and the telescoping leaf spring can be manipulated to cinch the annulus and additionally exert a radial compressive force on the annulus. In some embodiments, the method includes locking the telescoping leaf springs in the deployment configuration. In some embodiments, the anchors are adapted to engage a coronary sinus.

In some embodiments of the invention provides a tissue shaping device (such as a percutaneous mitral valve annuloplasty device) adapted to be deployed in a vessel to reshape tissue adjacent the vessel. The device comprises a first anchor and a second anchor and an elastic expandable leaf spring that can be adapted to be deployed by a catheter to engage a vessel wall. The two anchors can be reversibly engaged or disengaged atraumatically during deployment and the elastic expandable leaf spring can be manipulated to cinch the annulus and additionally exert a radial compressive force on the annulus. In some embodiments, the anchors are adapted to engage a coronary sinus.

In some embodiments the method includes capturing the first anchor and/or the second anchor within the catheter after the first anchoring step. The capturing step may include advancing a catheter distally over the anchor to place the anchor inside the catheter in the delivery configuration.

In some embodiments the method includes applying a proximally directed force on the mitral valve annuloplasty device after the first anchoring step. In some embodiments, the method includes uncoupling the device from a delivery tool after the second anchoring step. The uncoupling may comprise releasing a hitch wire from the device and removing a tether from the device.

In some embodiments, the device is scaled to be larger or smaller to accommodate the size of the annulus.

In a first specific aspect of the present invention, a prosthetic sealing device comprises a leaf-spring having a atrial leaf-spring segment and a ventricular leaf-spring segment. The segments are joined at a base and re configured to open in response to an opening force to form to a leaflet-receiving gap and to resiliently close toward each other when the opening force is removed. A body is attached to the base of the leaf-spring, where the body is configured to expand to inhibit the flow of blood through the body.

In particular embodiments, the body may comprise a self-expanding structure or may comprise a balloon expandable stent like structure. In other particular embodiments, the body may comprise a balloon, and the prosthetic sealing device may comprise an inflator or other means for remotely inflating the balloon to allow size adjustment after implantation. In yet further particular embodiments, the body may comprise a hollowed shaft, wherein the shaft is typically flexible and/or foldable. Alternatively, the body may comprise a solid, flexible body, a sponge-like material that is compressible and flexible, or may comprise a gel-like material.

In still further particular embodiments, the body and the leaf springs may be covered or coated with a material that promotes tissue in-growth. For example, the tissue in-growth promoting material may comprise a polyester fabric.

In yet other particular embodiments, the leaf-springs may comprise atraumatic barbs to securely grasp leaflets. The leaf-springs and body may be made of a shape memory or super-elastic material, such as a nickel-titanium alloy.

In still other particular embodiments, the prosthetic sealing devices may further comprising a second set of leaf springs that are configured to secure both anterior and posterior leaflets, with the body attached in between or at the side the two sets of the leaf springs. In some cases, the prosthetic sealing devices may further comprise a third set of leaf springs configured to secure each of the three tricuspid valve leaflets, with the body attached in between or at a side the leaf springs.

In yet additional particular embodiments, the prosthetic sealing devices further comprise two or more sets of leaf springs that are configured to secure a single leaflet.

In other instances, the prosthetic sealing devices comprises a retrieval suture configured to retrieve the prosthetic device during and/or after implantation. Optionally, the prosthetic device may be covered or coated with materials that inhibit formation of scar/fibrous tissue.

In a second specific aspect, the present invention provides method for inhibiting regurgitation in heart valves including mitral valves and tricuspid valve. The methods comprise providing a prosthetic sealing device as described above. A delivery port of a delivery cannula is positioned adjacent to a target heart valve in a patient, and the ventricular segment of the prosthetic sealing device is advanced distally through the delivery port of the delivery catheter. The ventricular segment of the prosthetic sealing device is positioned on one side of a target leaflet, and the atrial segment of the prosthetic sealing device is advanced distally through the delivery port of the delivery catheter to form the leaflet-receiving gap. The leaflet-receiving gap is positioned over the target leaflet, and the prosthetic sealing device is further advanced from the port such that the leaf-spring segments resiliently close over and capture the target leaflet. A tether or suture may optionally be used to lift and/or drop the leaf-spring to allow for repositioning and/or recapture of the target leaflet. Typically, the body is then expanded to inhibit a flow of blood therethrough.

The target heart valve is typically a mitral valve, and the target leaflet may be a posterior leaflet or an anterior leaflet. When only a single target leaflet is captured, a non-captured leaflet remains free to function after the prosthetic sealing device has been implanted. Alternatively, a second valve leaflet with a second set of leaf springs on the prosthetic sealing device may be used to capture both the leaflets.

The following numbered clauses describe other examples, aspects, and embodiments of the inventions described herein:
332

1. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a radially uncompressed configuration; advancing the prosthetic sealing device distally relative to the delivery catheter such that an anchor of the prosthetic sealing device moves out of the catheter and forms a leaflet-receiving gap between an end portion of the anchor and the delivery catheter; positioning either a posterior or an anterior mitral valve leaflet in the gap; and advancing a radially uncompressed body of the prosthetic sealing device out of the delivery catheter such that the body interacts with a portion of the elastically resilient anchor, reducing the gap, and capturing the leaflet between the body and the end portion of the anchor, wherein the body is configured to prevent the flow of blood through the body during systole and during diastole; wherein a non-captured one of the anterior and posterior leaflets is not secured to the prosthetic sealing device when the prosthetic sealing device is implanted for intended use at the native mitral valve.

2. The method of clause 1, wherein advancing a delivery catheter through the native mitral valve from a left atrium comprises advancing the delivery catheter through an incision in a portion of a septum between the left atrium and a right atrium.

3. The method of clause 1, wherein when the delivery catheter is advanced to the native mitral valve region of the heart, the anchor is held in a substantially straightened position within the delivery catheter extending distally from body of the prosthetic sealing device.

4. The method of clause 1, wherein when the device is laterally compressed within the delivery catheter and self-expands on delivery.

5. The method of clause 1, wherein when the device is laterally compressed within the delivery catheter and mechanically expanded on delivery.

6. The method of clause 1, wherein when the device is folded within the delivery catheter and self-unfolds on delivery.

7. The method of clause 1, wherein when the device is in a deflated configuration within the delivery catheter and inflated during delivery.

8. The method of clause 1, wherein when the device is in a deflated configuration within the delivery catheter and inflated post-delivery.

9. The method of clause 1, wherein the body comprises of wires, rods, flat wires, sheet metal or a combination of thereof, wherein the body comprises barbs or features that promote secure capture of leaflets.

10. The method of clause 1, wherein the anchor comprises of wires, rods, flat wires, sheet metal or a combination of thereof.

11. The method of clause 1, wherein the device comprises of wires, rods, flat wires, sheet metal or a combination of thereof, wherein the device comprises barbs or features that promote secure capture of leaflets.

12. The method of clause 1, wherein when the prosthetic device material comprises of metal, polymer, ceramic, super-elastic, shape-memory, gas, liquid, organic material or a combination of thereof.

13. The method of clause 1, wherein when the prosthetic device is fully or partially covered with fabric cover, polymer or metallic coating, drug, organic material or a combination of thereof.

14. A method of implanting a prosthetic sealing device at a native mitral valve, the method comprising: advancing a delivery device to a native mitral valve region via a left ventricle, the delivery catheter housing the prosthetic sealing device in a uncompressed configuration; allowing an anchor of the prosthetic sealing device to move radially out of the delivery device while a body of the prosthetic sealing device is in a uncompressed configuration, such that a leaflet-receiving gap forms between an end portion of the anchor and the delivery device; positioning either a posterior or an anterior mitral valve leaflet in the gap such that the leaflet is captured between the body and the anchor, wherein the body is configured to prevent the flow of blood through the body during systole and during diastole; wherein a non-captured one of the anterior and posterior mitral valve leaflets is not secured to the prosthetic sealing device when the prosthetic sealing device is implanted for intended use at the native mitral valve.

15. The method of clause 14, wherein advancing a delivery device to a native mitral valve region via a left ventricle comprises inserting the delivery device into the left ventricle through an incision in an apex of the left ventricle.

16. The method of clause 14, wherein advancing a delivery catheter through the native mitral valve from a left ventricle comprises advancing the delivery catheter through an aorta.

17. The method of clause 14, wherein when the delivery catheter is advanced to the native mitral valve region of the heart, the anchor is held in a substantially straightened position within the delivery catheter.

18. The method of implanting a prosthetic device, comprising: advancing a prosthetic device in an uncompressed configuration to an implantation location using a delivery apparatus, wherein the prosthetic device comprises a spacer body, a first anchor, and a second anchor; wherein the anchors are resiliently biased and have a first and a second configuration; and advancing the prosthetic sealing device distally relative to the delivery catheter such that the anchors of the prosthetic sealing device move out of the catheter in the first configuration and forms a leaflet-receiving gap between the end portion of the first anchor and the delivery catheter; positioning either a posterior or an anterior mitral valve leaflet in the gap formed by the first anchor; and manipulating the prosthetic sealing device distally relative to the delivery catheter such that first anchor transitions to the second configuration and the second anchor transitions to the first position; wherein the first anchor resiliently captures the first leaflet; positioning the second mitral valve leaflet in the gap formed by the second anchor; and manipulating the prosthetic sealing device distally relative to the delivery catheter such that second anchor transitions to the second configuration, wherein the second anchor resiliently captures the second leaflet; advancing the uncompressed body of the prosthetic sealing device out of the delivery catheter such that the body interacts with a portion of the elastically resilient anchor, and capturing the leaflets between the body and the end portion of the anchors, wherein the body is configured to prevent the flow of blood through the body during systole and during diastole; when the prosthetic sealing device is implanted for intended use at the native mitral valve.

19. The method of clause 18, wherein advancing a delivery catheter through the native mitral valve from a left atrium comprises advancing the delivery catheter through an incision in a portion of a septum between the left atrium and a right atrium.

20. The method of clause 18, wherein when the delivery catheter is advanced to the native mitral valve region of the heart, the anchor is held in a substantially straightened position within the delivery catheter.

21. The method of clause 18, wherein advancing a delivery device to a native mitral valve region via a left ventricle comprises inserting the delivery device into the left ventricle through an incision in an apex of the left ventricle.

22. The method of clause 18, wherein advancing a delivery catheter through the native mitral valve from a left ventricle comprises advancing the delivery catheter through an aorta.

Lateral Clauses

23. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a laterally compressed configuration; advancing the prosthetic sealing device distally relative to the delivery catheter such that an anchor of the prosthetic sealing device moves out of the catheter and forms a leaflet-receiving gap between an end portion of the anchor and the delivery catheter; positioning either a posterior or an anterior mitral valve leaflet in the gap; and advancing a laterally compressed body of the prosthetic sealing device out of the delivery catheter such that the body self-expands laterally towards the end portion of the anchor, reducing the gap, and capturing the leaflet between the body and the end portion of the anchor, wherein the body is configured to prevent the flow of blood through the body during systole and during diastole; wherein a non-captured one of the anterior and posterior leaflets is not secured to the prosthetic sealing device when the prosthetic sealing device is implanted for intended use at the native mitral valve.

24. A method of implanting a prosthetic sealing device at a native mitral valve, the method comprising: advancing a delivery device to a native mitral valve region via a left ventricle, the delivery catheter housing the prosthetic sealing device in a laterally compressed configuration; allowing an anchor of the prosthetic sealing device to move laterally out of the delivery device while a body of the prosthetic sealing device is in a compressed configuration, such that a leaflet-receiving gap forms between an end portion of the anchor and the delivery device; positioning either a posterior or an anterior mitral valve leaflet in the gap; and allowing the body of the prosthetic sealing device to laterally self-expand such that the leaflet is captured between the body and the anchor, wherein the body is configured to prevent the flow of blood through the body during systole and during diastole; wherein a non-captured one of the anterior and posterior mitral valve leaflets is not secured to the prosthetic sealing device when the prosthetic sealing device is implanted for intended use at the native mitral valve.

25. The method of implanting a prosthetic device, comprising: advancing a prosthetic device in a laterally compressed configuration to an implantation location using a delivery apparatus, wherein the prosthetic device comprises a spacer body, a first anchor, and a second anchor; wherein the anchors are resiliently biased and have a first and a second configuration; and advancing the prosthetic sealing device distally relative to the delivery catheter such that the anchors of the prosthetic sealing device moves out of the catheter in the first configuration and forms a leaflet-receiving gap between the end portion of the first anchor and the delivery catheter; positioning either a posterior or an anterior mitral valve leaflet in the gap formed by the first anchor; and advancing the prosthetic sealing device distally relative to the delivery catheter such that first anchor transitions to the second configuration and the second anchor transitions to the first configuration; wherein the first anchor resiliently captures the first leaflet; positioning the second mitral valve leaflet in the gap formed by the second anchor; and advancing the prosthetic sealing device distally relative to the delivery catheter such that second anchor transitions to the second configuration and resiliently captures the leaflet; advancing a laterally compressed body of the prosthetic sealing device out of the delivery catheter such that the body resiliently expands laterally to interact with a portion of the elastically resilient anchor to further engage with the leaflets, and capturing the leaflets between the body and the end portion of the anchors, wherein the body is configured to prevent the flow of blood through the body during systole and during diastole; when the prosthetic sealing device is implanted for intended use at the native mitral valve.

Spacer With Support Clauses

26. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a flexible space occupying configuration; wherein, the prosthetic sealing device comprises of a flexible body, an atrial support structure, and a ventricular support structure; advancing the prosthetic sealing device distally relative to the delivery catheter such that the ventricular support structure of the prosthetic sealing device moves out of the catheter and expands in the ventricular space; advancing the prosthetic sealing device out of the delivery catheter such that the body straddles the annulus and/or leaflet coapting space; retracting the delivery catheter and releasing the atrial support structure, whereby the atrial support structure resiliently expands in the atrial space; wherein the body is configured to prevent the flow of blood through the body during systole and during diastole; wherein a prosthetic device is allowed limited motion as constrained by the two support structures when the prosthetic sealing device is implanted for intended use at the native mitral valve.

27. A method of implanting a prosthetic sealing device at a native mitral valve, the method comprising: advancing a delivery device to a native mitral valve region via a left ventricle in to the left atrium, the delivery catheter housing the prosthetic sealing device in a flexible space occupying configuration; wherein, the prosthetic sealing device comprises of a flexible body, an atrial support structure, and a ventricle support structure; manipulating the delivery catheter to release the atrial support structure in the left atrium whereby the atrial support structure resiliently expands in the left atrium; manipulating the delivery catheter to further deploy the prosthetic device such that the body straddles the anulus and/or leaflet coapting space; manipulating the delivery catheter to release the ventricular support structure, whereby, the ventricular support structure resiliently expands in the ventricular space; wherein the body is configured to prevent the flow of blood through the body during systole and during diastole; wherein a prosthetic device is allowed limited motion as constrained by the two support structures when the prosthetic sealing device is implanted for intended use at the native mitral valve.

Expandable Spacer with Atrial and/or Ventricle Support Structures Clauses

28. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a compressed configuration; wherein, the prosthetic sealing device comprises of a body, an atrial support structure, and a ventricle support structure; advancing the prosthetic sealing device distally relative to the delivery catheter such that the ventricular support structure of the prosthetic sealing device moves out of the catheter and expands in the ventricular space; advancing the prosthetic sealing device out of the delivery catheter such that the body resiliently expands and straddles the annulus and/or leaflet coapting space; retracting the delivery catheter and releasing the atrial support structure, whereby the atrial support structure resiliently expands in the atrial space; wherein the expanded body is configured to prevent the flow of blood through the body during systole and during diastole; wherein a prosthetic device is allowed limited motion as constrained by the two support structures when the prosthetic sealing device is implanted for intended use at the native mitral valve.

29. A method of implanting a prosthetic sealing device at a native mitral valve, the method comprising: advancing a delivery device to a native mitral valve region via a left ventricle in to the left atrium, the delivery catheter housing the prosthetic sealing device in a compressed configuration; wherein, the prosthetic sealing device comprises of a body, an atrial support structure, and a ventricle support structure; manipulating the delivery catheter to release the atrial support structure in the left atrium whereby the atrial support structure resiliently expands in the left atrium; manipulating the delivery catheter to further deploy the prosthetic device such that the body resiliently expands and straddles the annulus and/or leaflet coapting space; manipulating the delivery catheter to release the ventricular support structure, whereby, the ventricular support structure resiliently expands in the ventricular space; wherein the body is configured to prevent the flow of blood through the body during systole and during diastole; wherein a prosthetic device is allowed limited motion as constrained by the two support structures when the prosthetic sealing device is implanted for intended use at the native mitral valve.

Balloon Spacer Clauses

30. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a deflated configuration; comprising of an inflatable body and an anchor, wherein the body and anchor are attached together; advancing the prosthetic sealing device distally relative to the delivery catheter such that an anchor of the prosthetic sealing device moves out of the catheter and forms a leaflet-receiving gap between an end portion of the anchor and the delivery catheter; positioning either a posterior or an anterior mitral valve leaflet in the gap; and advancing a deflated body of the prosthetic sealing device out of the delivery catheter and inflating the body such that the body inflates towards the end portion of the anchor, reducing the gap, and capturing the leaflet between the body and the end portion of the anchor, wherein the body is configured to prevent the flow of blood through the body during systole and during diastole; wherein a non-captured one of the anterior and posterior leaflets is not secured to the prosthetic sealing device when the prosthetic sealing device is implanted for intended use at the native mitral valve.

31. The method of clause 30, wherein advancing a delivery catheter through the native mitral valve from a left atrium comprises advancing the delivery catheter through an incision in a portion of a septum between the left atrium and a right atrium.

32. The method of clause 30, wherein when the delivery catheter is advanced to the native mitral valve region of the heart, the anchor is held in a substantially straightened position within the delivery catheter extending distally from body of the prosthetic sealing device.

33. The method of clause 30, wherein when the body of the device is in a deflated configuration within the delivery catheter and inflated during delivery.

34. The method of clause 30, wherein when the body of the device is in a deflated configuration within the delivery catheter and inflated post-delivery.

35. The method of clause 30, wherein when the body of the device is in a deflated configuration within the delivery catheter and inflated during delivery.

36. The method of clause 30, wherein when the device is in a deflated configuration within the delivery catheter and inflated post-delivery.

37. A method of implanting a prosthetic sealing device at a native mitral valve, the method comprising: advancing a delivery device to a native mitral valve region via a left ventricle, the delivery catheter housing the prosthetic sealing device in a deflated configuration; comprising of an inflatable body and an anchor, wherein the body and anchor are attached together; allowing an anchor of the prosthetic sealing device to move resiliently out of the delivery device while a body of the prosthetic sealing device is in a deflated configuration, such that a leaflet-receiving gap forms between an end portion of the anchor and the delivery device; positioning either a posterior or an anterior mitral valve leaflet in the gap; and inflating the body of the prosthetic sealing device to inflate such that the leaflet is captured between the body and the anchor, wherein the body is configured to prevent the flow of blood through the body during systole and during diastole; wherein a non-captured one of the anterior and posterior mitral valve leaflets is not secured to the prosthetic sealing device when the prosthetic sealing device is implanted for intended use at the native mitral valve.

38. The method of implanting a prosthetic device, comprising: advancing a prosthetic device in a laterally compressed configuration to an implantation location using a delivery apparatus, wherein the prosthetic device comprises an inflatable spacer body, a first anchor, and a second anchor; wherein the anchors are resiliently biased and have a first and a second configuration; and advancing the prosthetic sealing device distally relative to the delivery catheter such that the anchors of the prosthetic sealing device moves out of the catheter in the first configuration and forms a leaflet-receiving gap between the end portion of the first anchor and the delivery catheter; positioning either a posterior or an anterior mitral valve leaflet in the gap formed by the first anchor; and advancing the prosthetic sealing device distally relative to the delivery catheter such that first anchor transitions to the second configuration and the second anchor transitions to the first configuration; wherein the first anchor resiliently captures the first leaflet; positioning the second mitral valve leaflet in the gap formed by the second anchor; and advancing the prosthetic sealing device distally relative to the delivery catheter such that second anchor transitions to the second configuration and resiliently captures the leaflet; and advancing a deflated body of the prosthetic sealing device out of the delivery catheter and inflating the body such that the body inflates towards the end portion of the anchors, to further engage with the leaflets, and securely capturing the leaflets between the body and the end portion of the anchors, wherein the body is configured to prevent the flow of blood through the body during systole and during diastole; when the prosthetic sealing device is implanted for intended use at the native mitral valve.

39. The method of clause 38, wherein advancing a delivery catheter through the native mitral valve from a left atrium comprises advancing the delivery catheter through an incision in a portion of a septum between the left atrium and a right atrium.

40. The method of clause 38, wherein when the delivery catheter is advanced to the native mitral valve region of the heart, the anchor is held in a substantially straightened position within the delivery catheter.

41. The method of clause 38, wherein advancing a delivery device to a native mitral valve region via a left ventricle comprises inserting the delivery device into the left ventricle through an incision in an apex of the left ventricle.

42. The method of clause 38, wherein advancing a delivery catheter through the native mitral valve from a left ventricle comprises advancing the delivery catheter through an aorta.

Inflatable Spacer with Supports

43. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a deflated configuration; wherein, the prosthetic sealing device comprises of an inflatable body, an atrial support structure, and a ventricle support structure; advancing the prosthetic sealing device distally relative to the delivery catheter such that the ventricular support structure of the prosthetic sealing device moves out of the catheter and expands in the ventricular space; advancing the prosthetic sealing device out of the delivery catheter such that the body straddles the annulus and/or leaflet coapting space; inflating the body; retracting the delivery catheter and releasing the atrial support structure, whereby the atrial support structure resiliently expands in the atrial space; wherein the inflated body is configured to prevent the flow of blood through the body during systole and during diastole; wherein a prosthetic device is allowed limited motion as constrained by the two support structures when the prosthetic sealing device is implanted for intended use at the native mitral valve.

44. A method of implanting a prosthetic sealing device at a native mitral valve, the method comprising: advancing a delivery device to a native mitral valve region via a left ventricle in to the left atrium, the delivery catheter housing the prosthetic sealing device in a deflated configuration; wherein, the prosthetic sealing device comprises of an inflatable body, an atrial support structure, and a ventricular support structure; manipulating the delivery catheter to release the atrial support structure in the left atrium whereby the atrial support structure resiliently expands in the left atrium; manipulating the delivery catheter to further deploy the prosthetic device such that the body straddles the annulus and/or leaflet coapting space; inflating the body; manipulating the delivery catheter to release the ventricular support structure, whereby, the ventricular support structure resiliently expands in the ventricular space; wherein the body is configured to prevent the flow of blood through the body during systole and during diastole; wherein a prosthetic device is allowed limited motion as constrained by the two support structures when the prosthetic sealing device is implanted for intended use at the native mitral valve.

Leaf-Spring Clauses

45. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a straightened configuration; wherein, the prosthetic sealing device comprises of an atrial leaf-spring segment and a ventricular leaf-spring segment that are resiliently joined together at the base; advancing the prosthetic sealing device distally relative to the delivery catheter such that the ventricular segment of the prosthetic sealing device moves out of the catheter and forms a leaflet-receiving gap between an end portion of the anchor and the delivery catheter; positioning either a posterior or an anterior mitral valve leaflet in the gap; and advancing the atrial portion of the prosthetic sealing device out of the delivery catheter such that the atrial segment of the leaf-spring resiliently moves towards the end portion of the ventricular leaf-spring, reducing the gap and capturing the leaflet between the atrial and ventricular segments of the leaf-spring; wherein a non-captured one of the anterior and posterior leaflets is not secured to the prosthetic sealing device when the prosthetic sealing device is implanted for intended use at the native mitral valve.

46. The method of clause 45, wherein advancing a delivery catheter through the native mitral valve from a left atrium comprises advancing the delivery catheter through an incision in a portion of a septum between the left atrium and a right atrium.

47. The method of clause 45, wherein when the delivery catheter is advanced to the native mitral valve region of the heart, the anchor is held in a substantially straightened position within the delivery catheter extending distally from body of the prosthetic sealing device.

48. The method of clause 45, wherein when the leaf-spring is made of sheet metal.

49. The method of clause 45, wherein when the leaf-spring is made of wires, rods, flat wires, sheet metal or a combination of thereof, wherein the atrial and/or ventricular segments of the leaf-spring have frictional features, such as barbs, to enhance secure grasp of the leaflet.

50. The method of clause 45, wherein when the anchor is made of wires, rods, flat wires, sheet metal or a combination of thereof.

51. The method of clause 45, wherein when the prosthetic device is made of metal, polymer, ceramic, super-elastic, shape-memory, gas, liquid, gel, or a combination of thereof.

52. A method of implanting a prosthetic sealing device at a native mitral valve, the method comprising: advancing a delivery device to a native mitral valve region via a left ventricle, the delivery catheter housing the prosthetic sealing device in a straightened configuration; wherein, the prosthetic sealing device comprises of an atrial leaf-spring segment and a ventricular leaf-spring segment that are resiliently joined together at the base; allowing the ventricular segment of the leaf-spring to resiliently move laterally out of the delivery device while the atrial segment of the leaf-spring is in a straightened configuration within the delivery device, such that a leaflet-receiving gap forms between an end portion of the ventricular segment of the leaf-spring and the delivery device; positioning either a posterior or an anterior mitral valve leaflet in the gap; and allowing the atrial segment of the leaf-spring to resiliently move towards the ventricular segment, such that the leaflet is captured between the two leaf-spring segments; wherein a non-captured one of the anterior and posterior mitral valve leaflets is not secured to the prosthetic sealing device when the prosthetic sealing device is implanted for intended use at the native mitral valve.

53. The method of implanting a prosthetic device, comprising: advancing a prosthetic device in a straightened configuration to an implantation location using a delivery apparatus, wherein the prosthetic device comprises of a first leaf-spring and a second leaf-spring that are connected at the base; and each leaf-spring comprises of an atrial segment and a ventricular segment that are configured with a bias towards each other; wherein the ventricular segments of the leaf-spring s have a first and a second configuration; advancing the prosthetic sealing device distally relative to the delivery catheter such that the first ventricular segment of the prosthetic sealing device moves out of the catheter in the first configuration and forms a leaflet-receiving gap between the end portion of the first segment and the delivery catheter; positioning either a posterior or an anterior mitral valve leaflet in the gap formed by the first ventricular leaf-spring segment; and advancing the prosthetic sealing device distally relative to the delivery catheter such that first ventricular leaf-spring segment transitions to the second configuration and the second ventricular leaf-spring segment transitions to the first configuration; wherein the first ventricular leaf-spring segment resiliently captures the first leaflet; positioning the second mitral valve leaflet in the gap formed by the second ventricular leaf-spring segment; and allowing the prosthetic sealing device such that second ventricular leaf-spring segment transitions to the second configuration and resiliently captures the leaflet; advancing the straightened prosthetic sealing device out of the delivery catheter such that the first leaflet gets captured between the first atrial and ventricular segments of the first leaf-spring and the second leaflet gets captured between the second atrial and ventricular segments of the second leaf-spring; wherein the leaf-spring prosthetic device is configured to prevent the regurgitant flow of blood during systole; similar to Alfieri edge-to-edge repair technique when the prosthetic sealing device is implanted for intended use at the native mitral valve.

Spacer and Leaf-Spring Clauses

54. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a compressed and straightened configuration; wherein, the prosthetic sealing device comprises of a leaf-spring and a body, wherein the leaf-spring comprises of a atrial leaf-spring segment and a ventricular leaf-spring segment that are resiliently joined together at the base; wherein, the body is attached at the base of the leaf-spring; advancing the prosthetic sealing device distally relative to the delivery catheter such that the ventricular segment of the prosthetic sealing device moves out of the catheter and forms a leaflet-receiving gap between an end portion of the anchor and the delivery catheter; positioning either a posterior or an anterior mitral valve leaflet in the gap; and advancing the atrial portion of the prosthetic sealing device and the body out of the delivery catheter such that the atrial segment of the leaf-spring resiliently moves towards the end portion of the ventricular leaf-spring, reducing the gap and capturing the leaflet between the atrial and ventricular segments of the leaf-spring; wherein the body resiliently expands and is configured to prevent the flow of blood through the body during systole and during diastole; wherein a non-captured one of the anterior and posterior leaflets is not secured to the prosthetic sealing device when the prosthetic sealing device is implanted for intended use at the native mitral valve.

55. A method of implanting a prosthetic sealing device at a native mitral valve, the method comprising: advancing a delivery device to a native mitral valve region via a left ventricle, the delivery catheter housing the prosthetic sealing device in a compressed and straightened configuration; wherein, the prosthetic sealing device comprises of a leaf-spring and a body, wherein the leaf-spring comprises of a atrial leaf-spring segment and a ventricular leaf-spring segment that are resiliently joined together at the base; wherein, the body is attached at the base of the leaf-spring; allowing the ventricular segment of the leaf-spring to resiliently move laterally out of the delivery device, while the atrial segment of the leaf-spring in a straightened configuration within the delivery device, such that a leaflet-receiving gap forms between an end portion of the ventricular segment of the leaf-spring and the delivery device; positioning either a posterior or an anterior mitral valve leaflet in the gap; and allowing the atrial segment of the leaf-spring to resiliently move towards the ventricular segment, such that the leaflet is captured between the two leaf-spring segments; wherein the body resiliently expands and is configured to prevent the flow of blood through the body during systole and during diastole; wherein a non-captured one of the anterior and posterior mitral valve leaflets is not secured to the prosthetic sealing device when the prosthetic sealing device is implanted for intended use at the native mitral valve.

56. The method of implanting a prosthetic device, comprising: advancing a prosthetic device in a compressed and straightened configuration to an implantation location using a delivery apparatus, wherein the prosthetic device comprises of a first leaf-spring, a compressible body, and a second leaf-spring; wherein the body is sandwiched between the two leaf-springs; wherein, the body, first leaf-spring and second leaf-spring are connected at the base; and each leaf-spring comprises of an atrial segment and a ventricular segment that are configured with a resilient bias towards each other; wherein the ventricular segments of the leaf-springs have a first and a second configuration; advancing the prosthetic sealing device distally relative to the delivery catheter such that the first ventricular segment of the prosthetic sealing device moves out of the catheter in the first configuration and forms a leaflet-receiving gap between the end portion of the first segment and the delivery catheter; positioning either a posterior or an anterior mitral valve leaflet in the gap formed by the first ventricular leaf-spring segment; and advancing the prosthetic sealing device distally relative to the delivery catheter such that first ventricular leaf-spring segment transitions to the second configuration and the second ventricular leaf-spring segment transitions to the first configuration; wherein the first ventricular leaf-spring segment resiliently captures the first leaflet; positioning the second mitral valve leaflet in the gap formed by the second ventricular leaf-spring segment; and allowing the prosthetic sealing device such that second ventricular leaf-spring segment transitions to the second configuration and resiliently captures the leaflet; advancing the straightened prosthetic sealing device out of the delivery catheter such that the first leaflet gets captured between the first atrial and ventricular segments of the first leaf-spring, and the second leaflet gets captured between the second atrial and ventricular segments of the second leaf-spring; wherein the body resiliently expands to occupy space between the two leaflets; wherein the expanded body of the prosthetic device is configured to prevent the regurgitant flow of blood during systole; when the prosthetic sealing device is implanted for intended use at the native mitral valve.

57. The method of clause 56, wherein the body comprises of superelastic stent like material.

58. The method of clause 56, wherein advancing a delivery catheter through the native mitral valve from a left atrium comprises advancing the delivery catheter through an incision in a portion of a septum between the left atrium and a right atrium.

59. The method of clause 56, wherein when the delivery catheter is advanced to the native mitral valve region of the heart, the anchor is held in a substantially straightened position within the delivery catheter extending distally from body of the prosthetic sealing device.

60. The method of clause 56, wherein when the device is laterally compressed within the delivery catheter and self-expands on delivery and wherein the ventricular segments of the two leaf-springs move out of the delivery catheter at the same time and forms a leaflet-receiving gap between their end portions and the delivery catheter; advancing the body and the atrial segments of the delivery catheter allows for capture of the leaflets between the ventricular and atrial segments of the leaf-springs; the atrial segments allow for repositioning and/or repeated capture of the two leaflets simultaneously or sequentially using sutures, wires, or mechanical levers.

61. The method of clause 56, wherein when the device is laterally compressed within the delivery catheter and the body is mechanically expanded on delivery.

62. The method of clause 56, wherein when the body is folded within the delivery catheter and self-unfolds on delivery.

63. The method of clause 56, wherein when the body is in a deflated configuration within the delivery catheter and inflated during delivery.

64. The method of clause 56, wherein when the body is in a deflated configuration within the delivery catheter and inflated post-delivery.

65. The method of clause 56, wherein the body comprises of wires, rods, flat wires, sheet metal or a combination of thereof.

66. The method of clause 56, wherein the leaf-springs comprise wires, rods, flat wires, sheet metal or a combination of thereof.

67. The method of clause 56, wherein the device comprises of wires, rods, flat wires, sheet metal or a combination of thereof.

68. The method of clause 56, wherein when the prosthetic device material comprises of metal, polymer, ceramic, super-elastic, shape-memory, gas, liquid, organic material or a combination of thereof.

69. The method of clause 56, wherein when the prosthetic device is fully or partially covered with polyester, carbon, graphene, fluorocarbon (e.g. PTFE, PFA, FEP, ECTFE, ETFE), polypropylene, PEEK, PVDF, HDPE, LDPE, UHMWPE, Phosphorylcholine, hydroxyapatite, CaP, THV, polyglycerol sebacate, polylactic acid, polyglycolic acid, polymeric, metallic, ceramic and/or resorbable web, fibrous, braid, knit, woven or non-woven fabric; polymeric, metallic (e.g. Titanium, tantalum, gold, platinum), ceramic, drug, inorganic and/or organic material coating or a combination of thereof.

Spacer Sheet Clauses

70. A method of implanting a prosthetic sealing device at a native mitral valve of a heart, the method comprising: advancing a delivery catheter to a native mitral valve region of a heart from a left atrium of the heart, the delivery catheter housing the prosthetic sealing device in a laterally compressed configuration; advancing the prosthetic sealing device distally relative to the delivery catheter such that the prosthetic sealing device moves out of the catheter and seats against the annulus along the commissure to commissure gap, expanding to its natural configuration and thereby reducing the gap between the body and the leaflet, wherein the body is configured to prevent the flow of blood through the body during systole and during diastole.

71. The method of clause 70, wherein anchors or support members attached to the body keeps it within the gap between the leaflets.

72. The method of clause 70, wherein advancing a delivery catheter through the native mitral valve from a left atrium comprises advancing the delivery catheter through an incision in a portion of a septum between the left atrium and a right atrium.

73. The method of clause 70, wherein when the delivery catheter is advanced to the native mitral valve region of the heart, the anchor is held in a substantially straightened position within the delivery catheter extending distally from body of the prosthetic sealing device.

74. A method of implanting a prosthetic sealing device at a native mitral valve of a heart, the method comprising: advancing a delivery catheter to a native mitral valve region of a heart from a left atrium of the heart, the delivery catheter housing the prosthetic sealing device that contains a series of segments that can be assembled within the atria; and the assembled body is placed in the gap of the leaflet to reduce the gap to mitigate valve regurgitation.

Annulus Reshaping Device Clauses

75. A method of performing mitral valve annuloplasty on a patient's heart comprising: percutaneously delivering a mitral valve device to a coronary sinus, the mitral valve device comprising a first anchor, a second anchor, and a leaf spring like elongate body extending there between, the elongate body defining a longitudinal axis of the mitral valve device; anchoring the first anchor in an anchored configuration in the coronary sinus, wherein in the anchored configuration the first anchor comprises a flexible elongate member and a securing member for securing a first and second end of the flexible elongate member therein at a distal end of the securing member, the securing member generally aligned with the elongate body along the longitudinal axis, a first segment of the flexible elongate member extending from a distal end of the first anchor to a proximal end of the first anchor to engage the elongate body proximal the securing member, and a second segment of the flexible elongate member extending from where the first segment engages the elongate body to the distal end of the first anchor, and anchoring the second anchor in the coronary sinus.

76. The method of clause 75, wherein the elongate member can be made of multiple members that can slide, to reduce the distance between the distal and proximal anchors.

77. The method of clause 75, further comprising locking the sliding members in deployed configuration.

78. The method of clause 75, wherein there are more than one intermediate anchors and elongate members between the first and second anchors.

79. The method of clause 75, wherein the elongate member is stretchable and/or elastic and/or superelastic.

80. The method of clause 75, wherein the device is coated and/or covered with metal or polymer to improve biocompatibility.

81. The method of clause 75, wherein the device is coated and/or covered with metal or polymer to improve tissue ingrowth.

82. The method of clause 75, wherein the device is coated and/or covered with metal or polymer to limit tissue ingrowth for ease of removability post implantation.

83. The method of clause 75, wherein the device is made of bio-absorbable metal and/or polymer.

84. The method of clause 75, wherein the device is made of metal and/or polymer.

85. The method of clause 75, wherein the device is coated and/or impregnated and/or filled with drugs.

Native Heart Valve Implantation Clauses

86. A method of implanting a prosthetic sealing device at a native valve of a heart, the method comprising: advancing a delivery catheter to a native valve region of a heart, the delivery catheter housing the prosthetic sealing device in a radially uncompressed configuration; advancing the prosthetic sealing device distally relative to the delivery catheter such that one or more anchors of the prosthetic sealing device move out of the catheter and form a leaflet-receiving gap between an end portion of the anchor and the delivery catheter; positioning all or some of the valve leaflets in the gaps; and advancing a radially uncompressed body of the prosthetic sealing device out of the delivery catheter such that the body interacts with a portion of the elastically resilient anchor, and capturing the leaflets between the body and the end portion of the anchors, wherein the body is configured to prevent the flow of blood through the body during systole and during diastole; wherein any of the non-captured leaflets are not secured to the prosthetic sealing device when the prosthetic sealing device is implanted for intended use at the native valve.

87. The method of above clauses 86, wherein the native valve is a tricuspid valve and the prosthetic device has two or less anchors.

88. The method of above clauses 86, wherein the native valve is a tricuspid valve and the prosthetic device has three or more anchors.

89. The method of above clauses 1 to 88, wherein any of the exemplary embodiments and examples described in the above clauses or in this application, some or all can be made retrievable using known device retrievable methods, including some of the techniques described in this application.

90. The method of above clauses 1 to 88, wherein certain variations and modifications apparent to those skilled in the art, including embodiments or examples or clauses that may not provide all the features and benefits described herein; including obvious modifications and equivalents thereof; including embodiments comprising of various combinations or sub-combinations of the specific features and aspects of the embodiments examples claimed in the above clauses, wherein, the steps of any methods need not be performed sequentially.

BRIEF DESCRIPTION OF THE DRAWINGS

FIG. 6. is a side view of an exemplary sealing device.

FIG. 7. is another side view of the sealing device of FIG. 6.

FIG. 8. is an atrial end view of the sealing device of FIG. 6.

FIG. 9. is an atrial end view of the sealing device of FIG. 6 implanted at a native mitral valve.

FIG. 11. shows a sealing device having an anchor that extends from one side of a body, around a ventricular end of the body, and along a second side of the body.

FIGS. 12-15 show a method of deploying the sealing device of FIG. 11 from a delivery sheath FIG. 16. shows a portion of a human heart with an exemplary sealing device being implanted at the mitral region in a trans-septal approach.

FIGS. 18-21. show an exemplary prosthetic device having two anchors.

FIGS. 44-55 show exemplary prosthetic devices having various anchor configurations that allow for constrained location within the valve region and/or free floating and/or removability or combination of thereof.

FIGS. 58 and 59 show an alternate embodiment with non-circular body and the strings enter and exit from the atrial tip of the device.

FIGS. 61-67 show exemplary embodiments based on balloons as spacers.

FIGS. 79-81 show a method of deploying the exemplary device embodiment of FIG. 77 from a delivery sheath.

FIGS. 82-84 show a method of deploying the exemplary device embodiment of FIG. 77 from a stepped delivery sheath that allows for sequential engagement of leaflets.

FIG. 85 shows the distal stepped feature of the delivery sheath.

FIG. 132 shows an embodiment of spacer device 1270 that is segmented and can be assembled when released from the catheter 1272 in the atrium prior to deployment in the mitral valve.

FIG. 133 shows the embodiment 1272 with cinching string 1273 and crimps 1276, 1207.

FIG. 134 shows the embodiment 1272 in the cinched configuration.

DETAILED DESCRIPTION OF THE INVENTION

Figure 1:
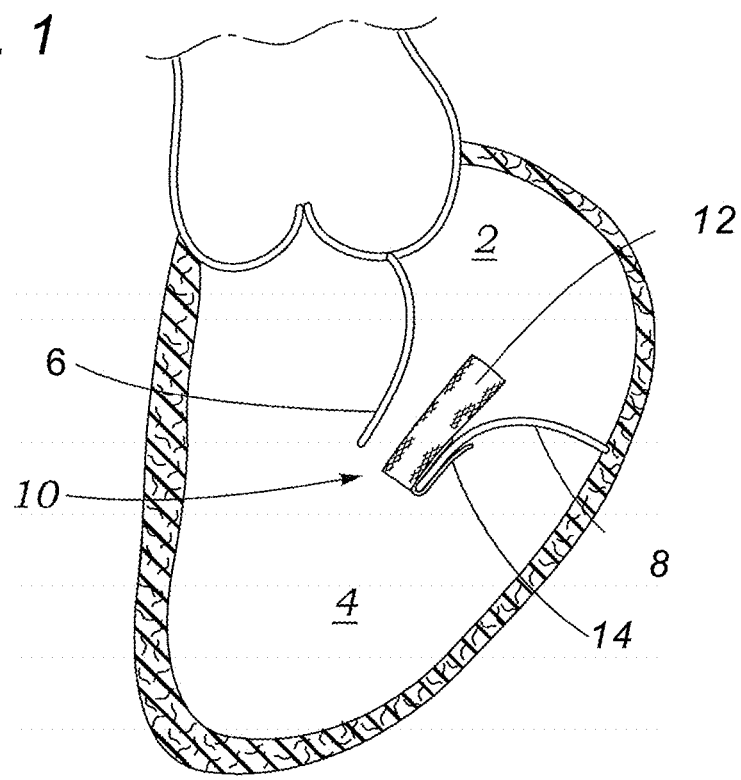
FIG. 1 shows a portion of a human heart with an exemplary embodiment of a sealing device attached to the native posterior mitral leaflet.

Described herein are embodiments of prosthetic devices that are primarily intended to be implanted at one of the mitral, aortic, tricuspid, or pulmonary valve regions of a human heart, as well as apparatuses and methods for implanting the same. The prosthetic devices can be used to help restore and/or replace the functionality of a defective native mitral valve. The disclosed embodiments should not be construed as limiting in any way. Instead, the present disclosure is directed toward all novel and nonobvious features and aspects of the various disclosed embodiments, alone and in various combinations and sub-combinations with one another.

Spacers

In some embodiments, a prosthetic device comprises a body and an anchor. The body is configured to be positioned within the native mitral valve orifice to help create a more effective seal between the native leaflets to prevent or minimize mitral regurgitation. The body can comprise a structure that is impervious to blood and that allows the native leaflets to close around the sides of the body during ventricular systole to block blood from flowing from the left ventricle back into the left atrium. The body is sometimes referred to herein as a spacer because the body can fill a space between improperly functioning native mitral leaflets that do not naturally close completely. In some embodiments, the body can comprise a prosthetic valve structure positioned within an annular body.

The body can have various shapes. In some embodiments, the body can have an elongated cylindrical shape having a round cross-sectional shape. In other embodiments, the body can have an ovular cross-sectional shape, a crescent cross-sectional shape, or various other non-cylindrical shapes. The body can have an atrial or upper end positioned in or adjacent to the left atrium, a ventricular or lower end positioned in or adjacent to the left ventricle, and an annular side surface that extends between the native mitral leaflets.

The body can be solid or hollow, elastic or compressible or incompressible or flexible or a combination of thereof.

Anchors, barbs and/or support members can be configured to secure the prosthetic device embodiment to one and/or both of the native mitral leaflets and/or the annulus such that the prosthetic body is positioned between the two native leaflets. The anchor can attach to the body at the ventricular region, atrial region, annular region and/or at the leaflets of the body. The anchor can be configured to be positioned above and/or behind a native leaflet when implanted such that the leaflet is captured between the anchor and the body. Alternatively, the anchor can be configured to be positioned to constrain the device with some or no freedom to move between the native leaflets or annulus when implanted.

The prosthetic device can be configured to be implanted via a delivery sheath. The body and the anchor can be a solid or hollow, compressible or incompressible and rigid or flexible. The device can be configured to allow the anchor to self-expand radially or laterally away from the body initially to create a gap between the body and the anchor. The leaflet can then be positioned in the gap. The body can then be allowed to contact the leaflet, closing the gap between the body and the anchor and capturing the leaflet between the body and the anchor. The implantation methods for various embodiments can be different, and are more fully discussed below with respect to each embodiment. Potential delivery methods are described, for example, in U.S. Pat. No. 9,414,918 B2, which is incorporated by reference herein in its entirety.

Some embodiments disclosed herein are generally configured to be secured to only one of the native mitral leaflets. However, other embodiments comprise more than one anchor and can be configured to be secured to both mitral leaflets. Further, there are other embodiments with anchors that allow for retrieval of the implanted body at a later date. Unless otherwise stated, any of the embodiments disclosed herein that comprise a single anchor can optionally be secured to the anterior mitral leaflet or secured to the posterior mitral leaflet, or secured to both regardless of whether the particular embodiments are shown as being secured to a particular one of the leaflets.

Some embodiments disclosed herein are generally configured to be secured to the annulus. Some embodiments disclosed herein are generally configured to be secured and/or supported by the atrial wall or features. Some embodiments disclosed herein are generally configured to be secured and/or supported by the ventricular wall or features. Some embodiments disclosed herein are generally configured to be secured and/or supported by the atrial wall and/or ventricular wall and/or annulus and/or leaflets and/or chordae and/or other heart features.

Some embodiments disclosed herein are generally configured with a anchor or anchor-like support structures that have coatings or coverings to promote tissue incorporation over chronic conditions. However, other embodiments comprise of biocompatible coatings or coverings that promote minimal or no tissue ingrowth—so as to enable device retrieval/removal at a later date. Unless otherwise stated, any of the embodiments may be configured to a) fully incorporate tissue, b) partially incorporate tissue, or c) minimal to no incorporation of tissue or a combination of tissue incorporation at various sites of the device, regardless of whether the particular embodiments are shown as being covered or coated.

Furthermore, some embodiments can optionally also include one or more atrial and/or ventricle anchors, such as to provide additional stabilization. Unless otherwise stated, any of the embodiments disclosed herein can optionally include an atrial (and/or ventricle) anchor or not include an atrial (and/or ventricle) anchor, regardless of whether the particular embodiments are shown with an atrial (and/or ventricle) anchor or not.

Some of the disclosed prosthetic devices are prevented from atrial embolization by having the anchor hooked around a leaflet, utilizing the tension from native chordae tendineae to resist high systolic pressure urging the device toward the left atrium. During diastole, the devices can rely on the compressive forces exerted on the leaflet that is captured between the body and the anchor to resist embolization into the left ventricle.

Some of the disclosed prosthetic devices have anchors and/or coatings/covering that allow for robust tissue incorporation. While some of the disclosed prosthetic devices have anchors and/or coatings/coverings that are designed to have limited or no tissue incorporation and allow the implant device to be removed (explanted) at later time post implantation.

FIG. 1 shows an exemplary embodiment of a prosthetic device 10 that comprises a body 12 and an anchor 14. The device 10 is secured to the posterior mitral leaflet 8 with the free end of the leaflet 8 captured between the anchor 14 and the body 12. In FIG. 1, the anterior mitral leaflet 6 is shown separated from the body 12 during diastole as blood flows from the left atrium 2 into the left ventricle 4. As the mitral leaflets open apart from each other, the device 10 can move with the posterior leaflet 8, allowing the anterior leaflet 6 to open away from the body 12. During systole, the back pressure on the leaflets closes them together around the body 12 to prevent mitral regurgitation.

Figure 2:
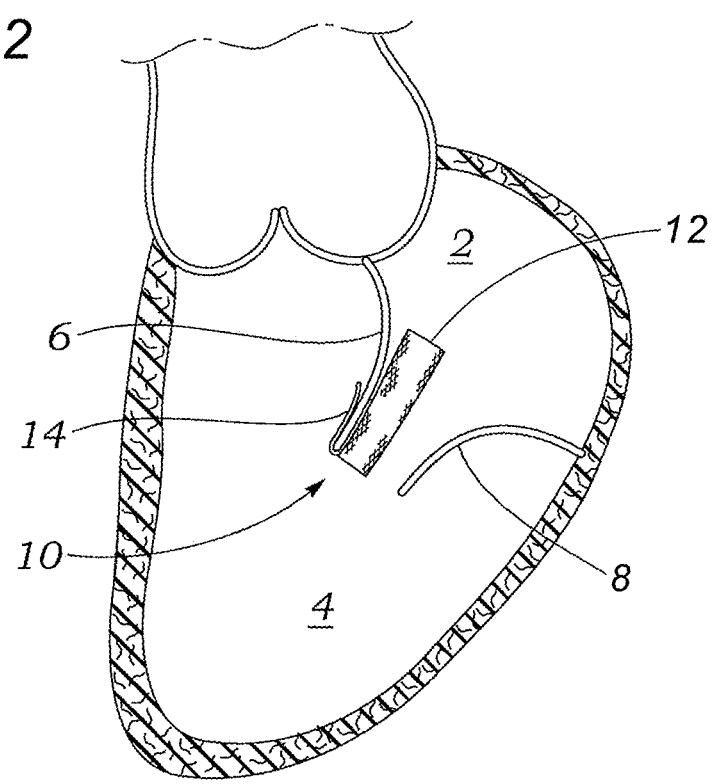
FIG. 2 shows a portion of a human heart with an exemplary embodiment of a sealing device attached to the native anterior mitral leaflet.

FIG. 2 shows the device 10 alternatively secured to the anterior mitral leaflet 6 with the posterior mitral leaflet 8 free to articulate toward and away from the device 10.

Figure 3:
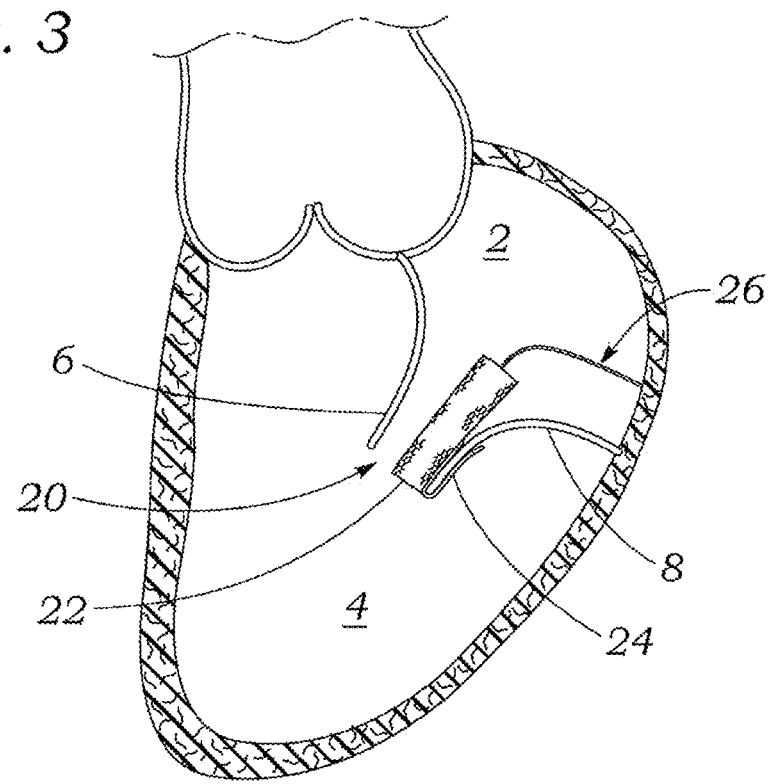
FIG. 3. shows a portion of a human heart with an exemplary embodiment of a sealing device attached to the native posterior mitral leaflet and having an atrial anchor.

FIG. 3 shows a prosthetic device 20 having a body 22, a ventricular anchor 24, and an atrial anchor 26. The device 20 is shown secured to the posterior leaflet 8 via the ventricular anchor 24. The atrial anchor 26 can extend laterally from adjacent the atrial end of the body 22 toward the mitral annulus or other lateral portions of the left atrium 2 adjacent to the posterior leaflet 8. The atrial anchor 26 can help stabilize the device. For example, the atrial anchor 26 can prevent the body 22 from tilting and keep it oriented longitudinally along the blood flow direction through the mitral orifice. The atrial anchor 26 can also help prevent the device 20 from embolizing into the left ventricle 4.

Figure 4:
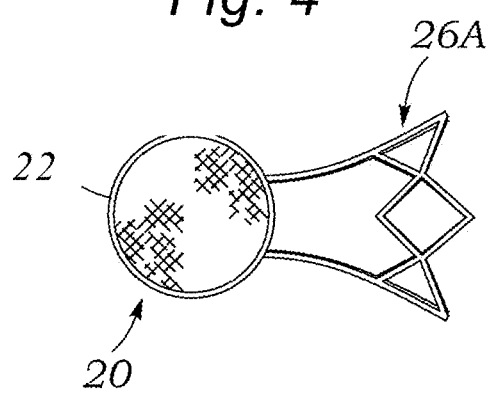
FIG. 4. is an atrial end view of one embodiment of the sealing device of FIG. 3 having a lattice-type atrial anchor.
Figure 5:
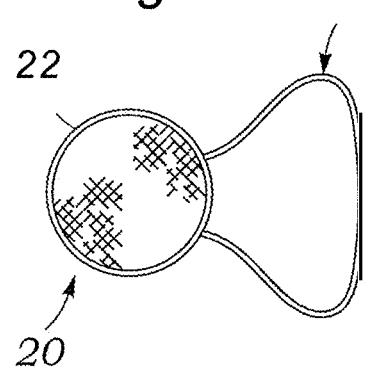
FIG. 5. is an atrial end view of another embodiment of the sealing device of FIG. 3 having a loop-type atrial anchor.
Figure 10A:
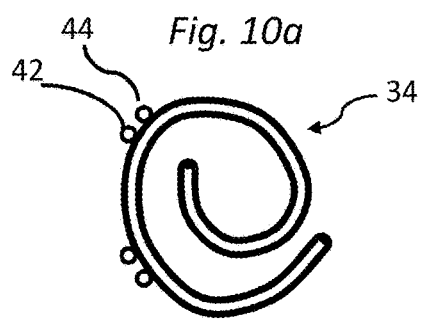
FIG. 10a-10d. show a crescent-shaped embodiment of a sealing device.
Figure 10B:
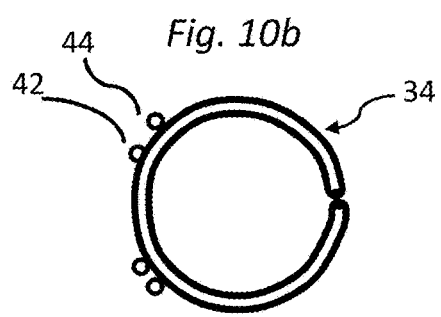
Figure 10C:
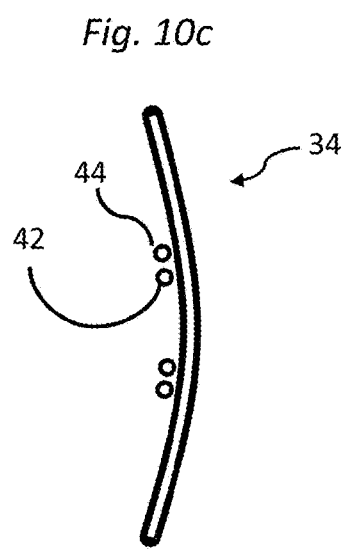
Figure 10D:
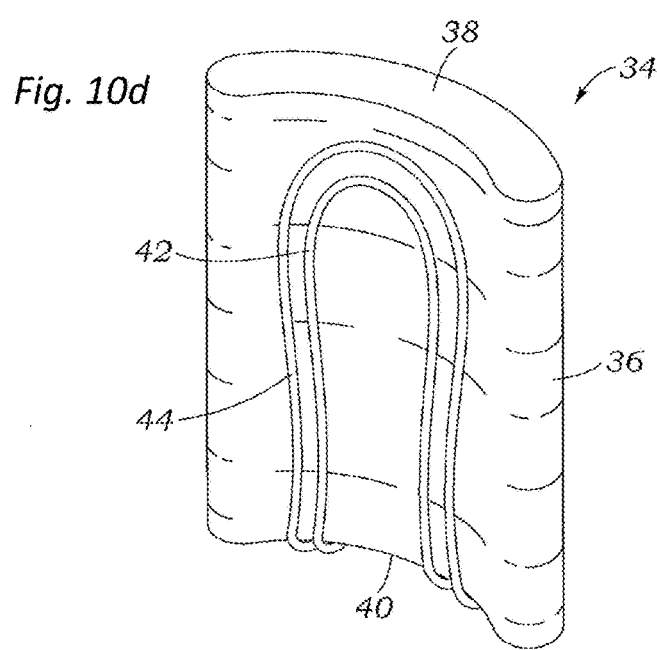

FIGS. 4 and 5 are atrial end views showing two alternative embodiments of atrial anchors for the device 20. FIG. 4 shows an atrial anchor 26A that comprises a lattice-type framework supported by two connections to the body 22, while FIG. 5 shows an atrial anchor 26B that comprises a single elongated member extending in a loop between two connections to the body 22. In both embodiments, the atrial anchor comprises a relatively broader or wider end portion configured to engage with the atrial tissue so as to spread out the engagement forces to avoid tissue damage and promote increased tissue ingrowth.

FIGS. 6-8 show three views of an exemplary embodiment of the prosthetic device 20 having a cylindrical body 22, a ventricular anchor 24, and an atrial anchor 26C. The ventricular anchor 24, as shown in FIGS. 6 and 7, comprises an elongated member that extends from two connection points adjacent the ventricular end of the body 22 and along one side of the body toward the atrial end of the body. The ventricular anchor is contoured around the generally cylindrical side surface of the body 22. The atrial anchor 26C comprises a lattice-type framework made up of several diamond-shaped segments 29 coupled side-by-side in an arc. The atrial anchor 26C further comprises three connecting members 27 coupling it to the body 22 adjacent the atrial end of the body. As shown in FIG. 6, the atrial member 26C extends generally laterally to the same side of the body 22 as the ventricular anchor 24. The radially outward end portion of the atrial anchor can have an upward curvature to conform to the curved geometry of the left atrium. Each of the diamond-shaped segments 29 comprises radially outwardly pointing tip 30 that can press into and/or penetrate adjacent tissue in some cases.

The device 20 is shown in final anchor configurations in FIGS. 3-9. In a delivery configuration, the atrial anchor 26 can be folded down against the side of the body 22 or extended upwardly away from the body 22. Furthermore, the atrial anchor 26 can be circumferentially compressed, especially embodiments having a lattice-type structure.

The body 22 can comprise an annular metal frame 32 covered with a blood-impervious fabric 28, as shown in FIGS. 6-9. One or both ends of the body can also be covered with the blood-impervious fabric 28 or film 28, as shown in FIG. 8. The fabric or film layer can comprise, for example, fluropolymers such as PTFE, FEP, ePTFE, Silicone, polyethylene terephthalate (PET) or polyurethane. Any of the spacers described herein (even if shown just as a frame) can include such a blood-impervious fabric layer covering the spacer, which can prevent blood from flowing through the spacer. The frame 32 can comprise a mesh-like structure comprising a plurality of interconnected metal struts. In other embodiments, the body can comprise a solid block of material, such as a rigid or flexible rod. In some embodiments, the body 22 can be hollow, tube-like or filled with material.

FIG. 9 is a view from the left atrium 2 of the device 20 of FIGS. 6-8 implanted at a mitral valve. The body 22 is positioned between the native leaflets 6, 8 in a sealed position with the atrial anchor 26C engaged with the atrial tissue adjacent the posterior mitral leaflet 8. The atrial end of the body 22 is open while the ventricular end of the body is covered with the impervious fabric 28.

The frame 22, 36 can be formed from a metal, polymer, or ceramic. When formed from a elastic material, the frame 22, 36 can be laterally compressed or flattened and/or folded to a delivery configuration and can be retained in the delivery configuration by placing the device in the sheath of a delivery apparatus, for example as shown in FIGS. 10a-10d. When deployed from the sheath, the frame 22, 36 can elastically recoil laterally or unfold to its functional size.

FIG. 11 shows an exemplary embodiment of a prosthetic device 50 having a body 52 and an anchor 54 that attaches to a first side of the body, extends around the ventricular end of the body, and extends along a second side of the body opposite the first side of the body. The device 50 is configured to capture a mitral leaflet between the anchor 54 and the second side of the body 52 to secure the body within the mitral orifice. The body 52 can comprise, for example, a solid rigid body or a solid flexible body or a laterally compressible and foldable metal stent covered by a blood impermeable fabric, as described above.

FIGS. 12-15 illustrate an exemplary method of deployment of the device 50 from a delivery catheter 56. In FIG. 12, the body 52 is shown within the catheter 56 with the anchor 54 extending distally from the ventricular end of the body in a straightened, or unfurled, state. A pusher member 59 can be used to push the device 50 distally relative to the catheter 56 or to hold the device 50 steady as the catheter is retracted. In FIG. 13, the catheter 56 is retracted proximally from the device 50 and/or the device 50 is advanced distally from the catheter 56 such that the elongated anchor 54 begins to extend out of the distal outlet 58 of the catheter. As the anchor 54 moves out of the outlet 58, the anchor begins to naturally return toward the shape of FIG. 11, curling gradually as it is freed from the confining forces of the catheter. In FIG. 14, the entire anchor 54 has moved out of the catheter 56 and has returned to its natural shape of FIG. 11. This curling action can be used to grab and position the mitral leaflet within the gap 60 while the device is in the configuration of FIG. 14. In FIG. 15, the ventricular end 62 of the body 52 begins to advance out of the outlet 58, allowing the ventricular end 62 of the body to come in contact with the mitral valve captured within the gap 60 and the anchor 54. In the fully advanced state shown in FIG. 11, the body is completely in contact with the mitral valve and gap is desirably sized such that a leaflet is engaged by the body and the anchor when placed in the gap.

In alternative embodiments, however, such a gap may not exist when the device is in its deployed state (i.e., the anchor 54 contacts the body 52 when a leaflet is not positioned between these two components). For example, this may be achieved by configuring the anchor 54 such that it is elastically biased towards the body 52. This allows a firm grip on the leaflet, when positioned in between the body 52 and the anchor 54. Additionally, the anchor 54 and/or the body 52 may have barbs to further constraint the leaflets.

Figure 16:
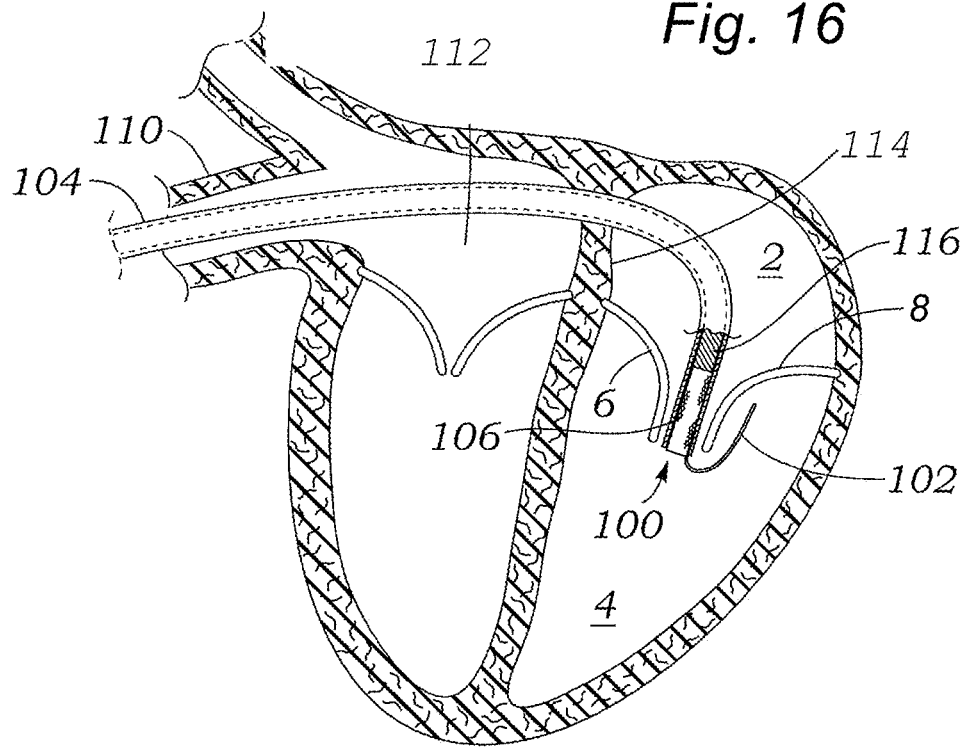
Figure 17:
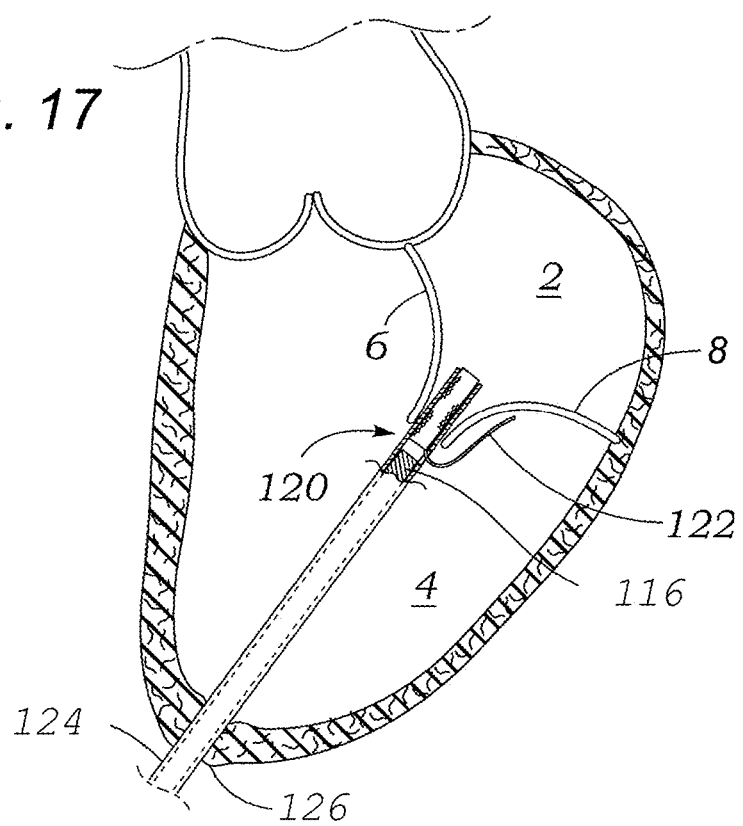
FIG. 17. shows a portion of a human heart with an exemplary sealing device being implanted at the mitral region in a transapical approach.

The exemplary prosthetic devices disclosed herein can be delivered to the mitral region via several different approaches. FIG. 16 shows an exemplary prosthetic device 100 having a single anchor 102, being delivered with a catheter 104 via an exemplary trans-septal atrial approach. In this approach, the catheter 104 passes through the inferior vena cava 110, the right atrium 112, and through an incision made in the septum 114, to reach the left atrium 2. The distal end portion 106 of the catheter 104 serves as a sheath for containing the prosthetic device 100 in a compressed state during delivery to the heart. The delivery apparatus can further include a pusher member 116 extending coaxially through the catheter 104. Once the catheter enters the left atrium 2, implantation of the device 100 can be performed similar to the methods described in relation to FIGS. 11-15 herein. The prosthetic devices described herein can be implanted via other exemplary approaches or methods common to those skilled in the field and/or for example as described in U.S. Pat. No. 9,414,918 B2, previously incorporated herein by reference. FIG. 17 shows an exemplary prosthetic device 120 having a single anchor 122, being delivered with a delivery device 124 through the apex 126 of the heart in an exemplary transapical approach. In the transapical approach shown in FIG. 17, the prosthetic device 120 is held within distal end of the delivery device 124. The delivery device 124 is inserted through an incision in the heart apex 126 and delivered through the left ventricle 4 to the mitral region. The delivery device 124 can have features that allow the anchor 122 to radially expand out of the delivery device 124 and away from the still-compressed body of the prosthetic device 120, as shown in FIG. 17, to capture one of the native mitral leaflets 6 or 8. For example, the delivery device 124 can have an outer sheath configured to release the anchor 122 while the body of the prosthetic device is held in an inner sheath, such as by providing a slot in the distal end portion of sheath 124 through which the anchor 122 can extend. In some embodiments, the delivery device 124 can be similar to the delivery device 2000 described in U.S. Pat. No. 9,414,918 B2, previously incorporated herein by reference. The delivery device 124 can also be similar to the delivery devices described in U.S. Pat. No. 9,439,763 B2, the full disclosure of which is incorporated herein by reference, and can be used to implant prosthetic devices via methods similar to those described therein.

Spacers Having Plural Anchors

In some embodiments, prosthetic devices can include a body and a plurality of anchors such that the body can be clipped to more than one leaflet. Such embodiments can be used to effectively couple two or more leaflets to one another. Thus, such a device can be used to bring native leaflets closer to one another and restrict their mobility in order help increase the chance of or extent of coaptation between the leaflets.

FIGS. 18-21 show a prosthetic spacer 600 having a body 602, a first anchor 604 and a second anchor 606. The body 602 and anchors 604, 606 can be fabricated from any of various suitable materials for delivery into a patient's heart within a delivery catheter. Alternatively, the body 602 can be foldable or laterally expandable (e.g., it can be fabricated from a frame comprising a self-expanding material such as Nitinol) such that the cross section of the body 602 can be reduced for delivery into a patient's heart and then expanded to a final, deployed configuration therein.

FIGS. 19 and 20 show that the anchors can have similar structures. Each anchor 604, 606 can be made from a single piece of relatively elastic metallic material (e.g., an elongated wire) which can include first and second inner portions 608, 610, first and second bottom portions 612, 614, and a main loop portion 616 extending between and connecting the upper ends of the bottom portions 612, 614. The inner portions 608, 610 can be mechanically coupled to the inside of the body 602. The inner portions 608, 610 can extend downwardly out of the lower end of body 602 to the respective bottom portions 612, 614, which can each curve upwardly around the lower end of the body 602 to meet the main loop portion 616.

FIGS. 20 and 21 show that the structure of the anchors 604, 606, and their connections to the body 602, biases the main loop portions 616 of the anchors 604, 606, into contact with the sides of the body 602. Thus, in use, the spacer 600 can be clipped to the anterior and posterior native leaflets 6, 8, with one of the leaflets 6, 8 clipped between the anchor 604 and the body 602, and the other of the leaflets 6, 8, clipped between the anchor 606 and the body 602. FIG. 21 shows that the anchors 604, 606 can be elastically splayed apart so that gaps exist between the anchors 604, 606, and the body 602. Thus, the spacer 600 can be introduced into the region of a patient's native mitral valve in a closed configuration with the anchors 604, 606 against the side of the body 602 (FIGS. 18-20). The anchors 604, 606 can then be splayed apart or expanded into an open configuration (FIG. 21) so the spacer can be positioned with the native leaflets 6, 8, in the gaps between the anchors 604, 606 and the body 602, after which the anchors 604, 606 can be allowed to return to the closed configuration under their own resiliency to capture the leaflets 6, 8, and clip the spacer 600 thereto. As mentioned earlier in previous embodiment, both the anchor 604, 606 and/or the body 602 may have protruding barbs for improved leaflet restraint.

Figure 22:
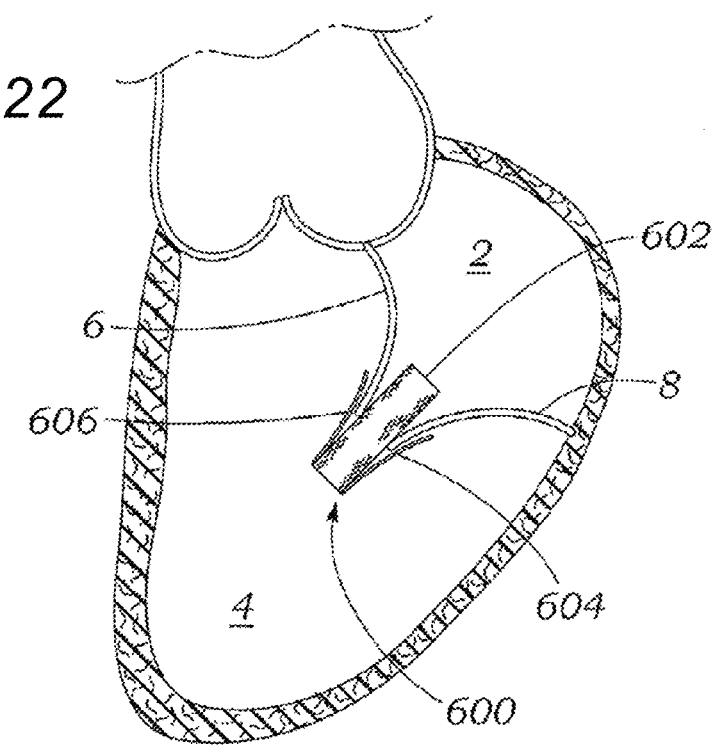
FIG. 22. shows an exemplary prosthetic device having two anchors, coupled to both of the native mitral valve leaflets.

The prosthetic spacer 600 can be clipped to the posterior native mitral valve leaflet 8 using the first anchor 604, as described with regard to prosthetic spacer 10 shown in FIG. 1, and can be clipped to the anterior native mitral valve leaflet 6 using the second anchor 606, as described above with regard to prosthetic spacer 10 shown in FIG. 2. FIG. 22, 23 show that when the prosthetic spacer 600 is clipped to both of the leaflets 6, 8, (e.g., at the A2 and P2 regions of the leaflets, as identified by Carpentier nomenclature) it brings them together, decreasing the overall area of the mitral valve orifice, and dividing the mitral valve orifice into two orifices 618, 620 during diastole. Thus, the area through which mitral regurgitation can occur is reduced, leaflet coaptation can be initiated at the location of the spacer 600, and the leaflets can fully coapt more easily, thereby preventing or minimizing mitral regurgitation.

Figure 24:
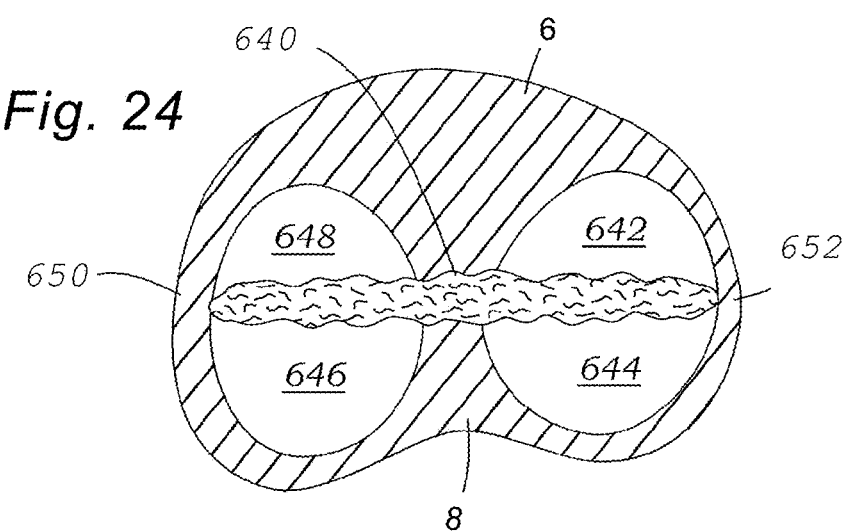
FIG. 24 shows an exemplary prosthetic device having an elongated body and two anchors, coupled to both of the native mitral valve leaflets, from an atrial view.

FIG. 24 shows alternative embodiments of dual anchor spacers clipped to the A2 and P2 regions of the anterior and posterior native leaflets 6, 8, as viewed from the left atrium.

Figure 23:
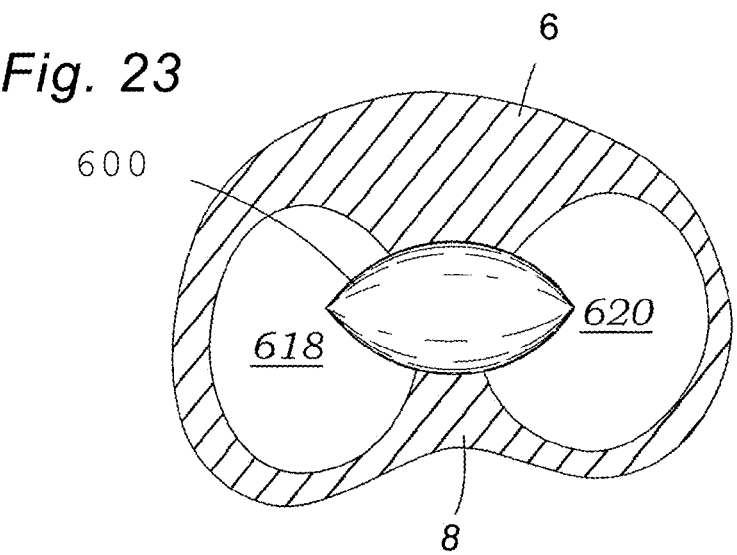
FIG. 23 shows an exemplary prosthetic device having two anchors, coupled to both of the native mitral valve leaflets, from an atrial view.
Figure 25:
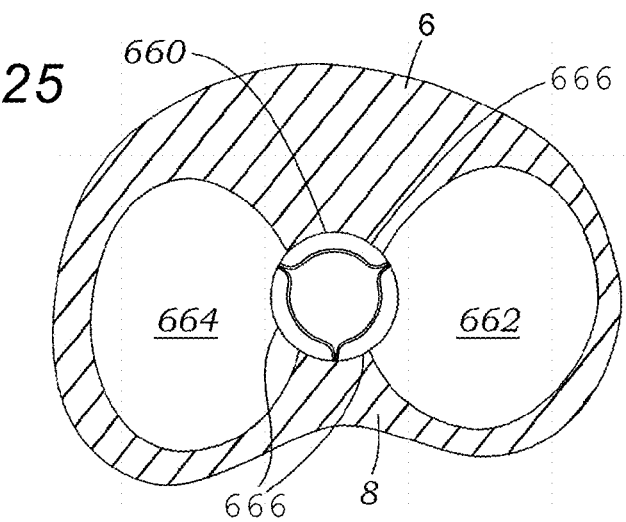
FIG. 25 shows an exemplary prosthetic device having a valve and two anchors, coupled to both of the native mitral valve leaflets, from an atrial view.

FIG. 25 shows an embodiment of a dual-anchor spacer 660 in which the body of the spacer 660 comprises a prosthetic valve having one or more flexible leaflets 666 that permit blood to flow into the left ventricle during diastole and block the back flow of blood into the left atrium during systole. In this embodiment, the native leaflets 6, 8 are brought closer to one another and the native mitral valve orifice is divided into two orifices 662, 664 during diastole. Because the body of the spacer 660 comprises a prosthetic valve, rather than a solid piece of material, the total effective open area between the leaflets during diastole (e.g., the area through which blood can flow) is greater in this embodiment than in the embodiment illustrated in FIG. 23.

Figure 26:
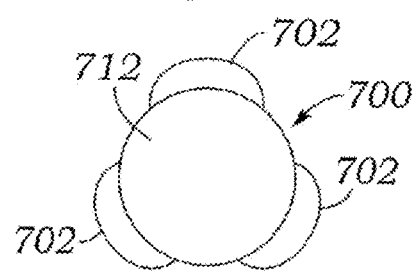
FIGS. 26-30 show exemplary prosthetic devices having three anchors.
Figure 27:
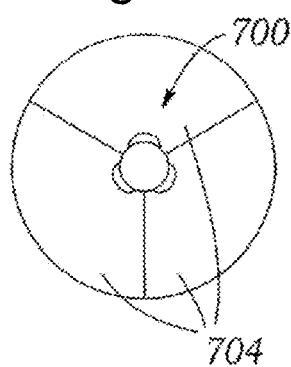
Figure 28:
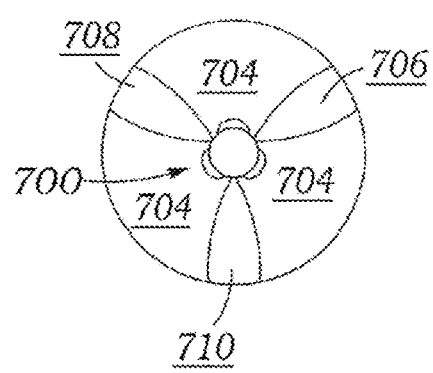
Figure 29:
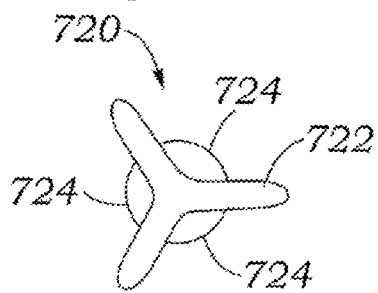
Figure 30:
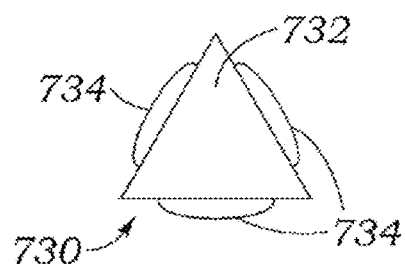

FIGS. 26-30 show embodiments of spacers having three anchors, which can be clipped to leaflets in the tricuspid valve of the human heart in a manner similar to that described above with regard to spacers in the mitral valve. FIG. 26 shows a tricuspid spacer 700 having a circular body 712 and three anchors 702. FIG. 27 shows the spacer 700 implanted in the tricuspid valve (as viewed from the right ventricle, as blood is being pumped out of the right ventricle), with each of the three anchors 702 clipped to a respective leaflet 704 of the tricuspid valve, and thereby coupling them to one another. FIG. 28 shows the spacer 700 clipped to the leaflets 704 of the tricuspid valve as blood is pumped from the right atrium to the right ventricle through orifices 706, 708, 710. FIG. 29 shows an alternative tricuspid spacer 720 having a body 722 and three clips 724. As shown, the body 722 can have a generally Y shape. FIG. 30 shows an alternative tricuspid spacer 730 having a body 732 and three clips 734. As shown, the body 732 can have a generally triangular shape.

Figure 31:
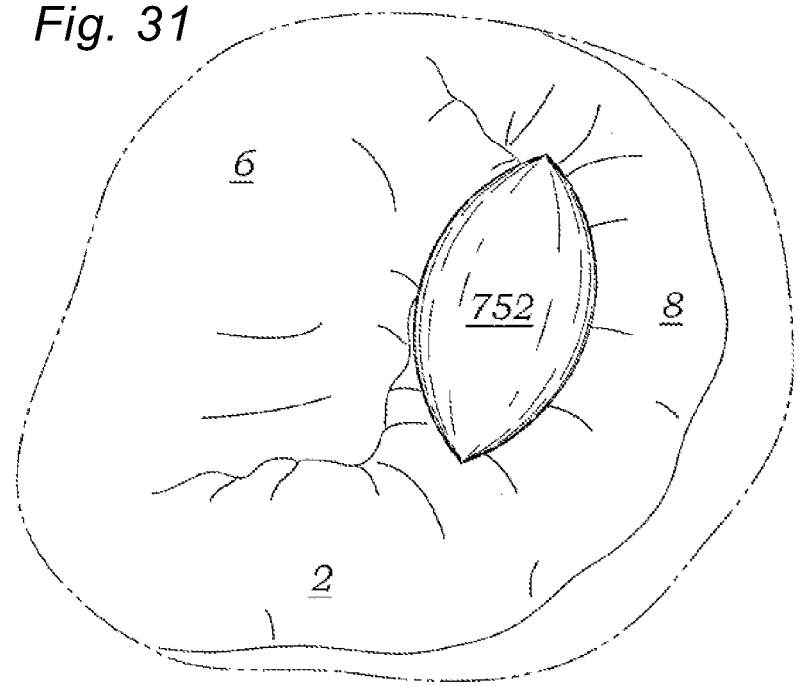
FIGS. 31-32 show the prosthetic device of FIGS. 18-21 implanted at a native mitral valve.
Figure 32:
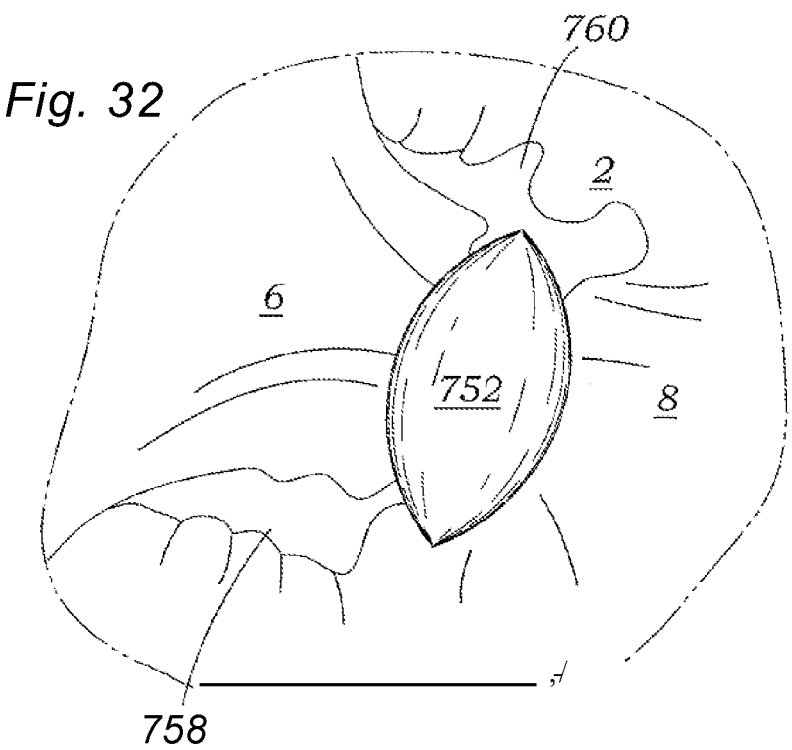

FIGS. 31-32 show an exemplary dual anchor spacer 750 having a body 752 and first and second anchors 754, 756, positioned within a native mitral valve. FIG. 31 shows the spacer 750 from the left atrium 2 during diastole. As can be seen in FIG. 31, no openings appear through which regurgitant flow can occur. In FIG. 32, two openings 758, 760 exist through which blood can flow from the left atrium 2 to the left ventricle 4 during diastole, as is desirable.

Figure 33:
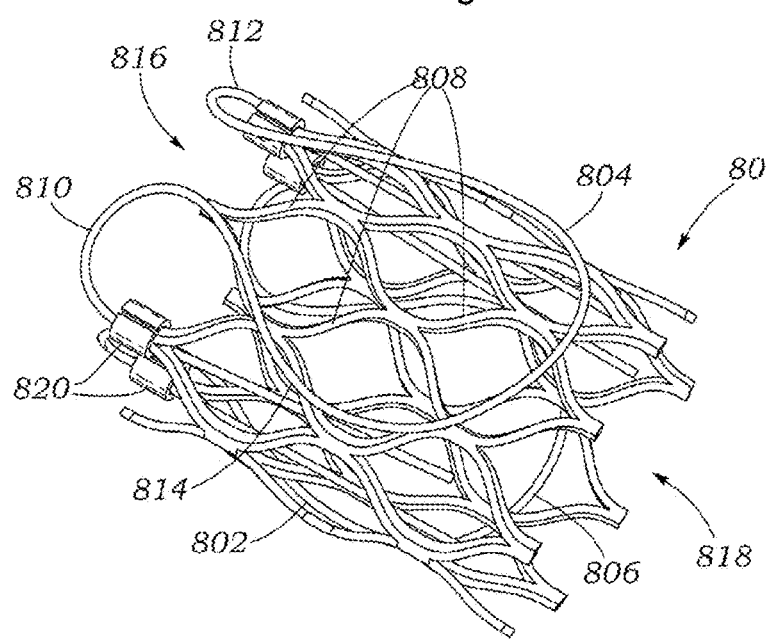
FIGS. 33 and 34 show another exemplary prosthetic device.
Figure 34:
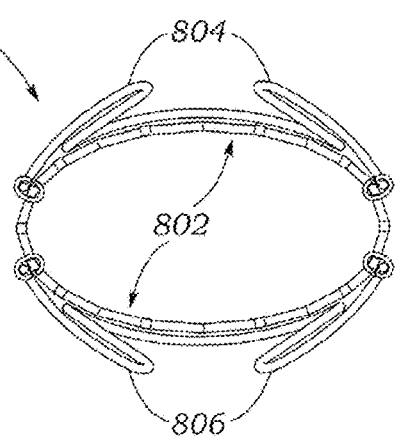

FIGS. 33 and 34 show an exemplary dual anchor spacer 800 comprising a main body 802 and first and second anchors 804, 806. The main body 802 can comprise a plurality of interconnected struts 808 which together form a plurality of open cells and are arranged to form a generally annular shape having first and second end portions 816, 818. The body 802 can be formed to be rigid, elastic or flexible. For example, the body 802 can be fabricated from a shape-memory material such as nickel titanium alloy (Nitinol®), or other common implant materials used in stents, such as titanium, PEEK, and/or PLGA.

The first anchor 804 can comprise first and second end portions 810, 812 which can be coupled to the first end portion 816 of the main body 802, and a loop portion 814 which can extend between the first and second end portions 810, 812. The first and second end portions 810, 812 can extend away from the first end portion 816 of the body 802, then curl back and extend toward the second end portion 818 of the main body 802. The loop portion 814 can be coupled to the first end portion 810, extend generally toward the second end portion 818 of the main body 802, curl back and extend toward the first end portion 816 of the main body 802, and be coupled to the second end portion 812.

Thus, the first anchor 804 can be coupled to the first end portion 816 of the main body 802 and extend along the side of the main body 802 toward its second end portion 818. The second anchor 806 can have a similar structure, and can be coupled to the main body 802 such that it extends along an opposing side of the main body 802. In this embodiment, the spacer 800 can be clipped to native tissues by pinching the native tissues between the anchors 804, 806 and the respective sides of the main body 802. The anchors 804, 806 can be made from various suitable materials, and in one exemplary embodiment can be fabricated from the shape-memory material Nitinol. The anchors 804, 806 in the illustrated embodiment are fabricated from separate pieces of material from the main body 802, and are coupled to the main body 802 using coupling mechanisms 820. The coupling mechanisms 820 can be, for example, crimping rings that extend around a strut at the first end 816 of the main body 802 and an adjacent portion of an anchor. In alternative embodiments, however, the anchors 804, 806 and the main body 802 can be fabricated integrally with one another (i.e., from a single piece of material). As best shown in FIG. 34, the main body 802 can have a generally elliptical or oval shape when viewed on end, but in alternative embodiments, the main body can be formed to have any of various suitable shapes when viewed on end, such as a circle.

Figure 35:
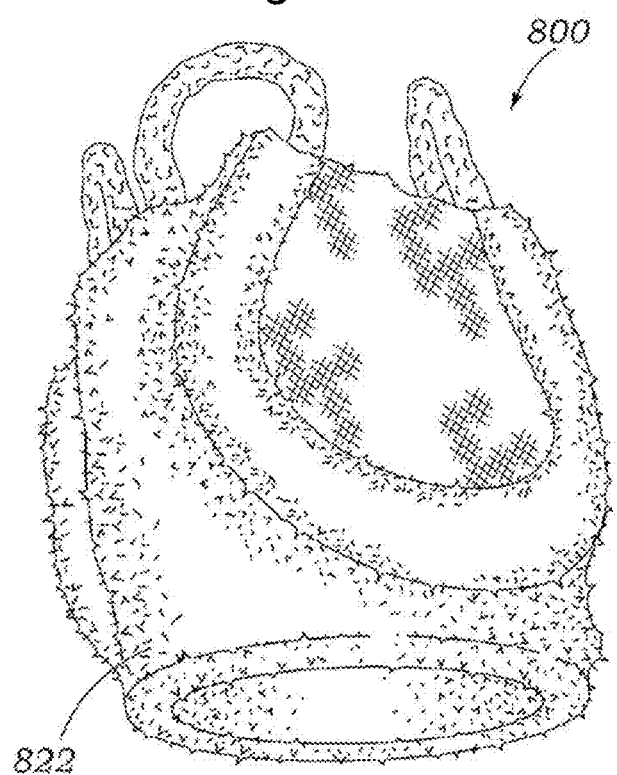
FIGS. 35 and 36 show the prosthetic device of FIGS. 33 and 34 with a fabric layer.
Figure 36:
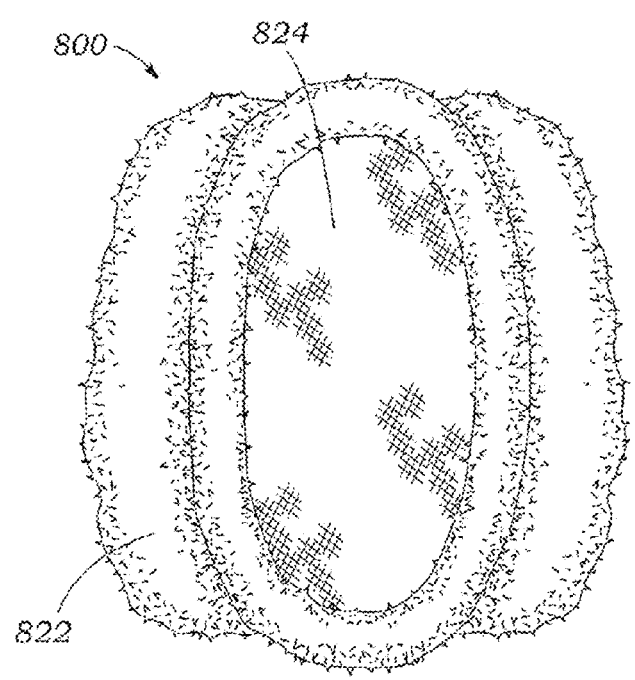

FIGS. 35 and 36 show the spacer 800 covered in a blood impermeable fabric material 822, such as made of polyester, polyethylene terephthalate (PET), fluoropolymers such as PTFE or polyurethane. The fabric material 822 can be relatively thick, strong, and soft, such as a knitted lofty cloth. The fabric material 822 can be selected to provide a softer surface for contact with the native tissue, thus reducing trauma caused to the native tissues by the implantation of the spacer 800, can be selected to promote native tissue ingrowth into the spacer 800, and/or can be selected to improve the seal formed between native tissues and the portions of the spacer 800 they come into contact with. Additionally, FIG. 36 shows that a fabric layer 824 can be disposed to cover all or substantially all of the opening at the center of the main body 802. The layer 824 can be blood impermeable, thereby blocking the flow of blood through the spacer 800. The layer 824 can be formed from the same material as fabric 822, and together the fabric 822 and layer 824 can work to prevent the regurgitant flow of blood through a heart valve when the spacer has been implanted therein.

Figure 37:
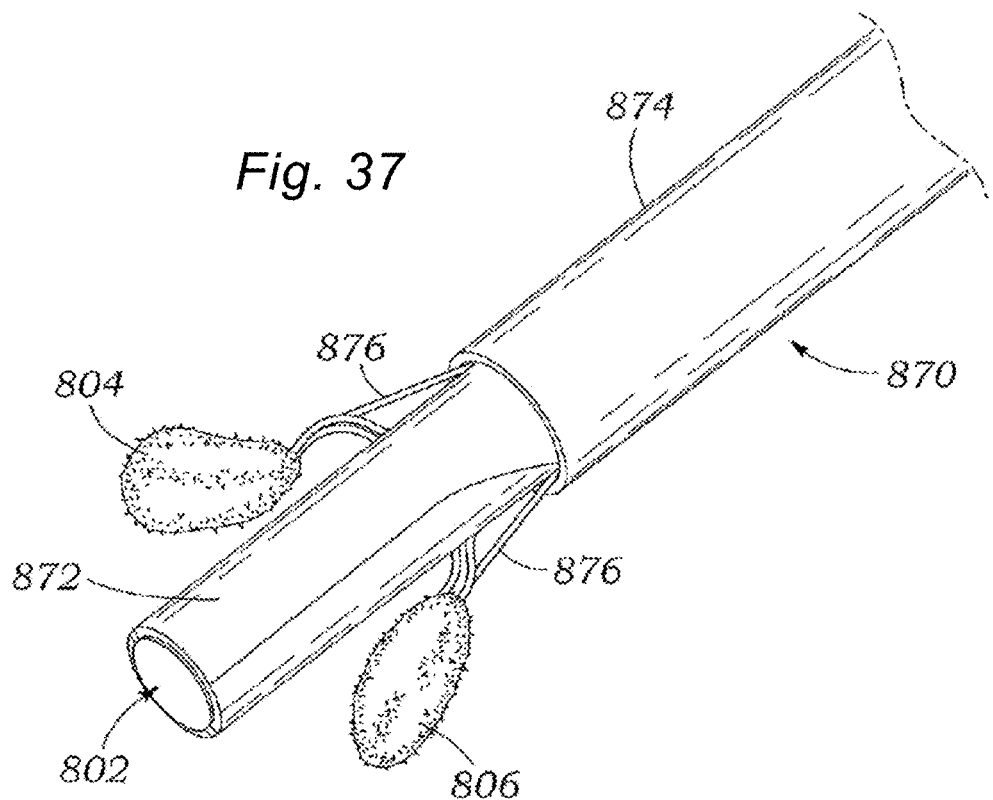
FIGS. 37-38 show an exemplary prosthetic device with an exemplary delivery system, in various configurations.
Figure 38:
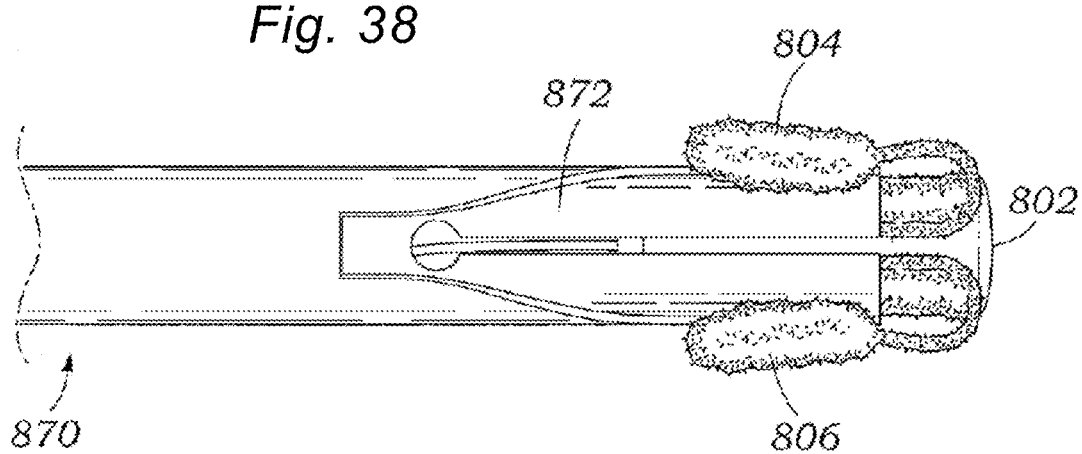

FIGS. 37 and 38 show a spacer 800 covered in fabric as described above and situated within a delivery device 870 in two different configurations. FIG. 37 shows the spacer 800 having its main body portion 802 situated within an inner sheath 872 of the delivery device 870 such that the anchors 804, 806 extend toward a distal end portion of the delivery device 870. In this embodiment, an outer sheath 874 can be extended distally to retain and secure the anchors 804, 806 against the sides of the inner sheath 872. Such a configuration can be used to deliver the spacer transapically, as described below. In some embodiments, retraction of the outer sheath 874 can allow the anchors 804, 806 to self-expand to a splayed-apart configuration.

FIG. 37 also shows that forcible expanders, or levers, 876 can be used to force the anchors 804, 806 to splay apart. The forcible expanders 876 can be radially self-expanding levers which radially self-expand when the outer sheath 874 is retracted or are otherwise configured to radially expand away from the inner sheath when they are actuated by a physician (such as by actuating a control knob on a handle that is operatively connected to the expanders 876). The expanders 876 can alternatively be sutures or other mechanisms which can be actuated by a physician to force the anchors 804, 806 to splay apart. In some embodiments, retraction of the outer sheath 874 can allow the anchors 804, 806 to self-expand to a first splayed-apart configuration, and forcible expanders 876 can be actuated to force the anchors 804, 806 to further radially expand to a second splayed-apart configuration. In such an embodiment, the expanders 876 can be actuated to cause the anchors 804, 806 to radially expand to the second splayed apart configuration, and can then be actuated to allow the anchors 804, 806 to move radially inward and return to the first splayed-apart configuration.

FIGS. 37 and 38 illustrate the spacer 800 situated within the delivery system 870 such that the anchors 804, 806 extend generally along the outside of the body 802 toward the second end portion 818 of the spacer 800. In alternative embodiments, however, the configuration of the body 802 and anchors 804, 806 within the delivery system 870, and the deployment of the spacer 800 from the delivery system 870, can be similar to that illustrated in FIGS. 12-15 with respect to device 50 and delivery catheter 56.

FIG. 38 shows the spacer 800 having its main body portion 802 situated within the inner sheath 872 of the delivery device 870 such that the anchors 804, 806 extend toward a proximal end portion of the delivery device 870. In this embodiment, the outer sheath 874 can be extended distally to retain and secure the anchors 804, 806 against the sides of the inner sheath 872. Such a configuration can be used to deliver the spacer transatrially, as described below.

Prosthetic spacers described herein can be delivered using minimally invasive approaches. FIGS. 39-42 show various approaches by which a prosthetic spacer 800 can be delivered to the region of a patient's mitral valve using a delivery system 920. For example, a prosthetic spacer can be delivered via a transapical approach (FIG. 39), via a transeptal approach (FIG. 40), via a transatrial approach (FIG. 41), or via a transfemoral artery approach (FIG. 42). FIGS. 39-42 show that the delivery system 920 can comprise an outer sheath 922, an inner sheath 924, and a guidewire 930 which can extend through the outer sheath 922 and inner sheath 924. The delivery system 920 can also include a pusher element (not illustrated in FIGS. 39-42, but similar to those described above), which can be actuated to move the spacer 800 within the inner sheath 924. The outer sheath 922, inner sheath 924, guidewire 930, and pusher element can each be retracted proximally or extended distally with respect to one another. The guidewire 930 can be used to guide the delivery of the other components of the system 920 to an appropriate location within a patient's vasculature. The guidewire 930 can extend through a small opening or pore in the spacer 800, for example in the fabric layer 824, the small opening or pore being small enough that substantial blood cannot flow therethrough.

Figure 39:
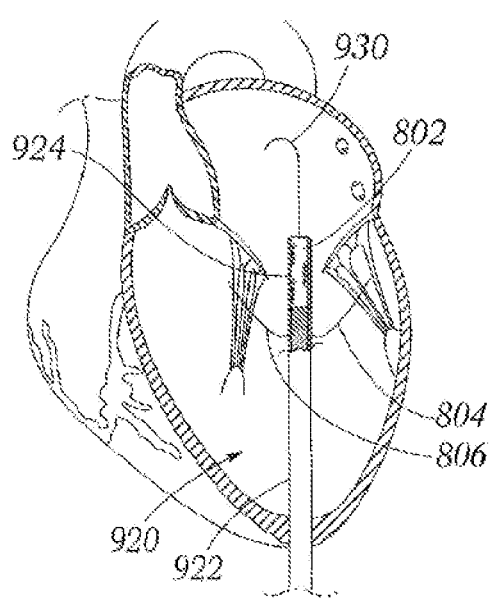
FIGS. 39-42 show various exemplary delivery approaches for delivering a prosthetic device to a native mitral valve.

FIGS. 39 and 42 show that the deployment of the spacer 800 to a native mitral valve via the transapical approach can be similar to the deployment of the valve 800 via the transfemoral approach, at least because in both cases the valve is delivered to the mitral valve from the left ventricle. In preparing the delivery system 920 for delivery of the spacer 800 via the transapical or the transfemoral artery approach, the spacer 800 can be situated within the system 920 with the second end portion 818 of the spacer 800 disposed at the distal end of the system 920 (such as shown in FIG. 37). In the transapical and the transfemoral artery approaches, the delivery system 920 can be used to first deliver the spacer 800 to the region of the native mitral valve from the left ventricle. In the transapical approach, the delivery device 920 is inserted into the left ventricle via an opening in the chest and the apex of the heart. In the transfemoral approach, the delivery device 920 can be inserted into a femoral artery and advanced through the aorta in a retrograde direction until the distal end of the delivery device is in the left ventricle. The outer sheath 922 can then be retracted proximally such that the anchors 804, 806 are no longer confined within the outer sheath 922. In some embodiments, the anchors 804, 806 can be configured to self-expand to a splayed apart configuration shown in FIGS. 39 and 42. In other embodiments, as described above, the delivery system 920 can include a mechanism for forcing the anchors 804, 806 to splay apart to the splayed-apart configuration (such as described above with respect to the embodiment of FIG. 37). The device 920 can then be distally advanced so that the native mitral valve leaflets are positioned between the splayed apart anchors 804, 806, and the body 802. The inner sheath 924 can then be retracted so that the body 802 is no longer confined within the inner sheath 924 and can radially expand to an expanded configuration between the native mitral valve leaflets. In some embodiments, the body 802 can expand such that the native leaflets are pinched between the body 802 and the anchors 804, 806. In alternative embodiments, as described above, the mechanism for forcing the anchors 804, 806 to splay apart can be actuated to allow the anchors 804, 806 to move radially inward toward the main body 802, thereby pinching the native leaflets between the main body 802 and the anchors 804, 806.

Figure 40:
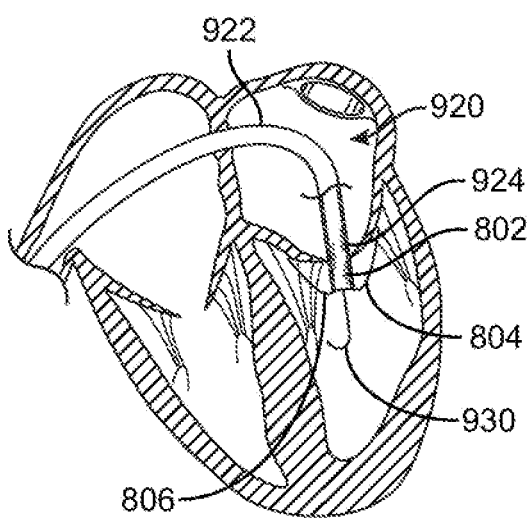
Figure 41:
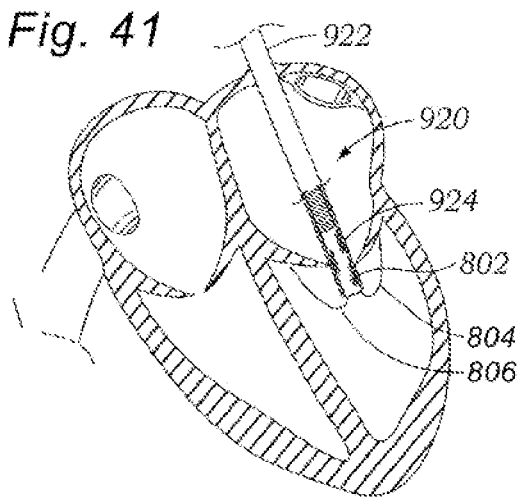
Figure 42:
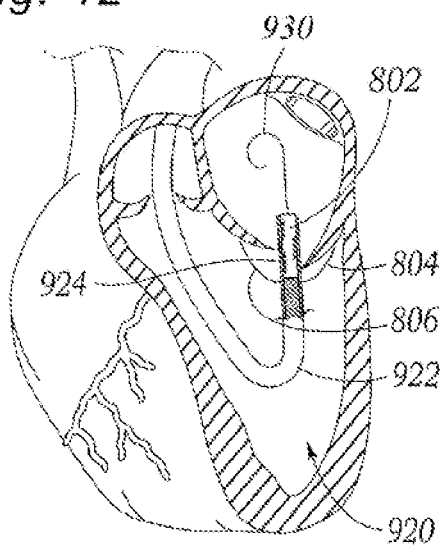

FIGS. 40 and 41 show that the deployment of the spacer 800 to a native mitral valve via the transseptal approach can be similar to the deployment of the valve 800 via the transatrial approach, at least because in both cases the valve is delivered to the mitral valve from the left atrium. In preparing the delivery system 920 for delivery of the spacer 800 via the transseptal or the transatrial approach, the spacer 800 can be situated within the system 920 with the first end portion 816 of the spacer 800 disposed at the distal end of the system 920 (such as shown in FIG. 38). In these approaches, the delivery system 920 can be used to first deliver the spacer 800 to the region of the native mitral valve from the left atrium. The outer sheath 922 can then be retracted proximally such that the anchors 804, 806 are no longer confined within the outer sheath 922. In some embodiments, the anchors 804, 806 can be configured to self-expand to a splayed apart configuration shown in FIGS. 40 and 41. In other embodiments, as described above, the delivery system 920 can include a mechanism for forcing the anchors 804, 806 to splay apart to the splayed-apart configuration.

The system 920 can then be proximally retracted so that the native mitral valve leaflets are positioned between the splayed apart anchors 804, 806, and the body 802. The inner sheath 924 can then be retracted so that the body 802 is no longer confined within the inner sheath 924 and can expand to an expanded configuration between the native mitral valve leaflets. In some embodiments, the body 802 can expand laterally such that the native leaflets are pinched between the body 802 and the anchors 804, 806. In alternative embodiments, as described above, the mechanism for forcing the anchors 804, 806 to splay apart can be actuated to allow the anchors 804, 806 to move radially inward toward the main body 802, thereby pinching the native leaflets between the main body 802 and the anchors 804, 806.

In any of the four approaches described above, once the native leaflets have been captured by the spacer 800, the delivery system 920 can be retracted and removed from the patient's vasculature. The spacer 800 can remain in the native mitral valve region, with the main body 802 being situated between the two native leaflets, thereby helping to reduce or prevent mitral regurgitation. It will be understood that similar techniques can be used to deliver a spacer to the native aortic, tricuspid, or pulmonary valves, depending on the needs of the patient.

Figure 43:
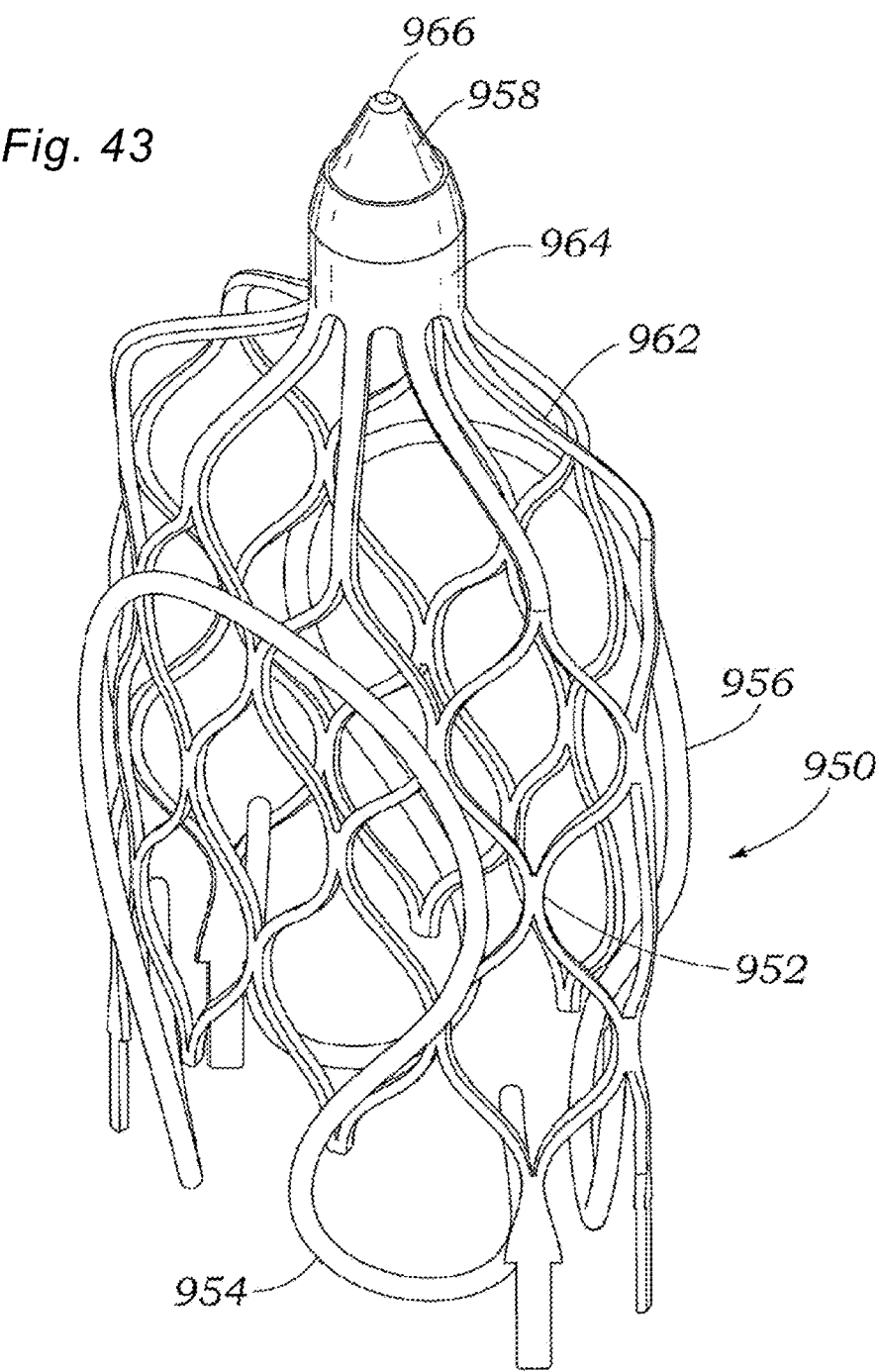
FIG. 43 shows an exemplary variation of the prosthetic device. While not show, the body of the prosthetic device can have barbs to better grip on the leaflets.

FIG. 43 shows an exemplary dual anchor spacer 950 which can be delivered to the region of the native mitral valve via any suitable delivery method, for example, using the transapical, transseptal, transatrial, or transfemoral techniques described above. The spacer 950 can include a main body 952, a first anchor 954, a second anchor 956, and a nosecone 958. The spacer 950 can also include a tapered portion 962, which can couple the main body portion 952 to a neck portion 964. The taperer portion 962 can have a variable width which can taper from the width of the main body 952 to the width of the neck portion 964. The neck portion 964 can be configured to receive a portion of the nosecone 958 therein, and can be coupled to the nosecone 958. The main body 952 and anchors 954, 956 can be fabricated from various materials, as described above with regard to other embodiments, and the nosecone 958 can be fabricated from various suitable materials such as a long term implantable silicone or other suitable elastomers.

The nosecone 958 can have a small pore, or opening, or slit, 966, which can extend through and along the length of the nosecone 958. In accordance with suitable delivery methods making use of a guidewire such as guidewire 930, the guidewire can extend through the opening 966, thus eliminating the need for an opening or pore in a fabric layer. The spacer 950 can facilitate crossing of a native heart valve due to its tapered tip, which can also provide improvements in hydrodynamics during diastolic blood flow. When a guidewire is removed from the opening 966, the opening can close under its own resiliency and/or blood pressure, thus leaving a sealed spacer implanted at a native heart valve. Alternatively, or in addition, the opening 966 can be sufficiently small to prevent significant amounts of blood from travelling through the nosecone 958.

FIGS. 44-55 show exemplary prosthetic devices having various anchor configurations that allow for constrained location within the valve region and/or free floating and/or removability or combination of thereof. The body 1009 can be rigid, flexible, elastic, hollow (such as inflatable balloon) and/or solid. As mentioned with previous device embodiments, these prosthetic devices can be made from metal, polymer and/or ceramic with or without coatings or coverings.

Figure 44:
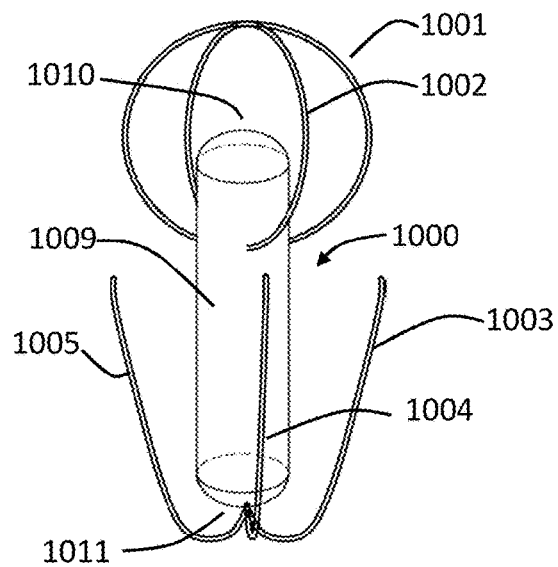

FIG. 44 shows looped atrial support structures 1001, 1002 that can be made from elastic polymer such as PEEK or super elastic metal such as nitinol. At the ventricular end 1011 of the device 1000, ventricular support structures 1005, 1004 and 1005 cantilever out of the tip of the body 1009. These structures can be loaded inside a deliver catheter in a stretched configuration and can resiliently assume the deployment configuration as shown in the FIGS. 44-45.

Figure 45:
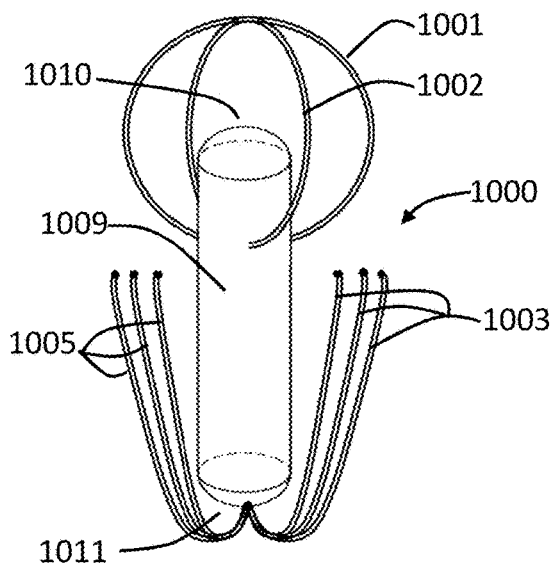
Figure 46:
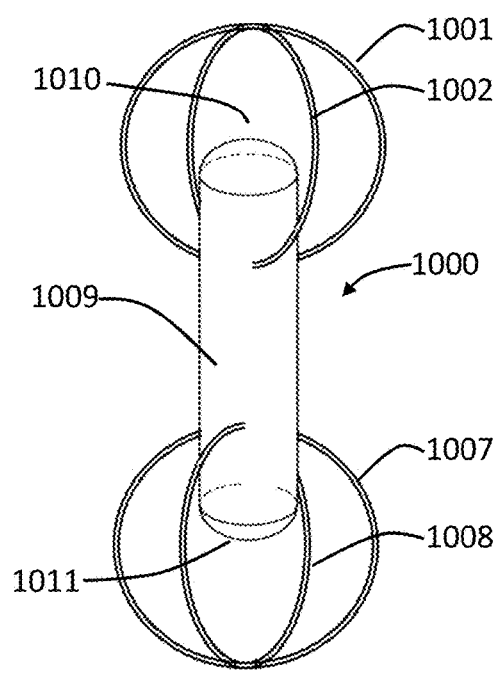
Figure 47:
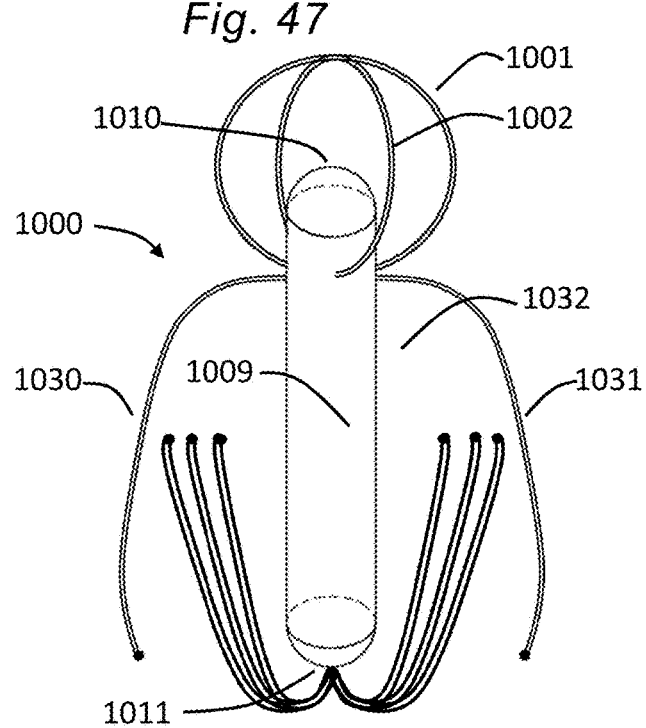
Figure 51:
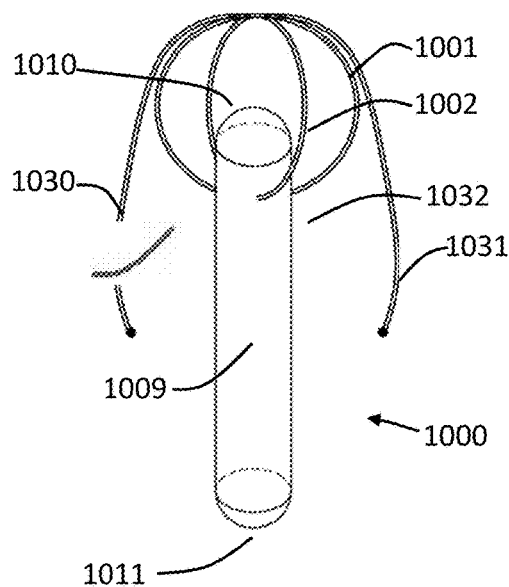

Both atrial and ventricular support structures are configured to allow for retrieval of the device post implantation from the atrial side, by grasping the atrial loops and retracting the entire device into the catheter. FIG. 45 shows a variation of embodiment shown in FIG. 44, wherein, a plurality of ventricular support structures 1003, 1005 are configured to be aligned with anterior and posterior mitral valves aspects. FIG. 46 shows an embodiment that has looped support structures at both atrial 1010 and ventricular 1011 sides of the body 1009. FIG. 47 shows an embodiment based off the embodiment shown in FIG. 45, with an additional support structures 1030, 1031 that cantilevers from the atrial side 1010 of the body 1009 and straddles across the annulus, with free ends terminating in the ventricular side 1011. These support structures 1030, 1031 are configured to be aligned with the inter-commissure structure of the mitral valve. The preferred location of the annulus along the length of the body 1009 is shown by 1032. FIGS. 48-54 show different configurations of the support structures described earlier in FIGS. 44-47. In these embodiments, the support structured 1015-1018 originate from the body 1009 of the device 1000 in FIG. 48, while 1012, 1014, 1003, 1005 originate from the tip the body 1009 FIG. 50. FIGS. 49, 51 show a embodiments where the support structures 1001, 1002, 1012, 1014, 1021-1026, 1030, 1031 originate from various staggered locations of the body 1009. FIGS. 52-54 show support structures that straddle across the annulus with a indent like feature to better conform to the annulus location 1032. FIG. 55 shows an embodiment where the support structure that straddles across the annulus forms a closed loop 1037, 1038.

Figure 48:
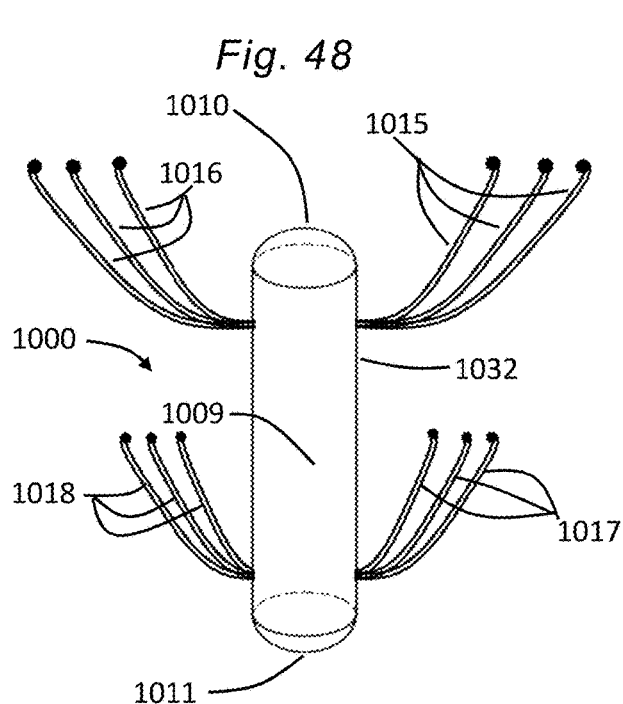
Figure 49:
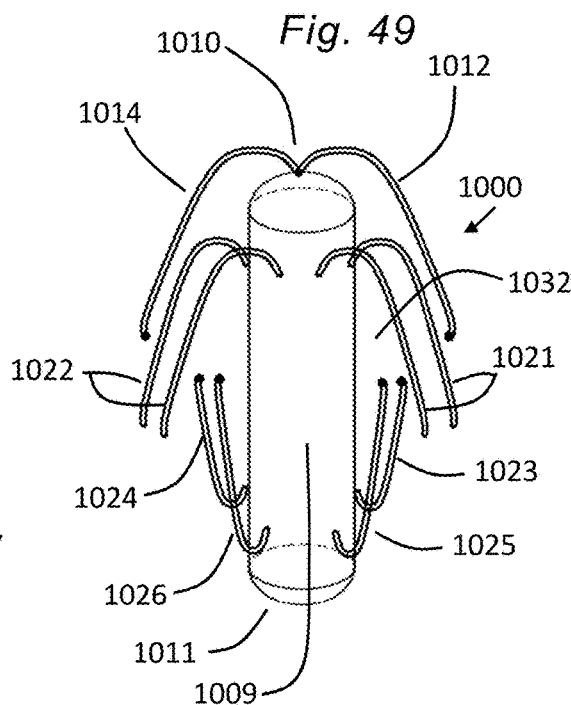
Figure 50:
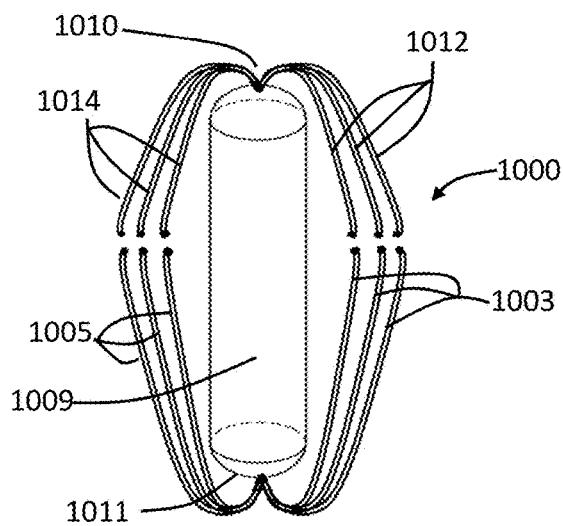
Figure 56:
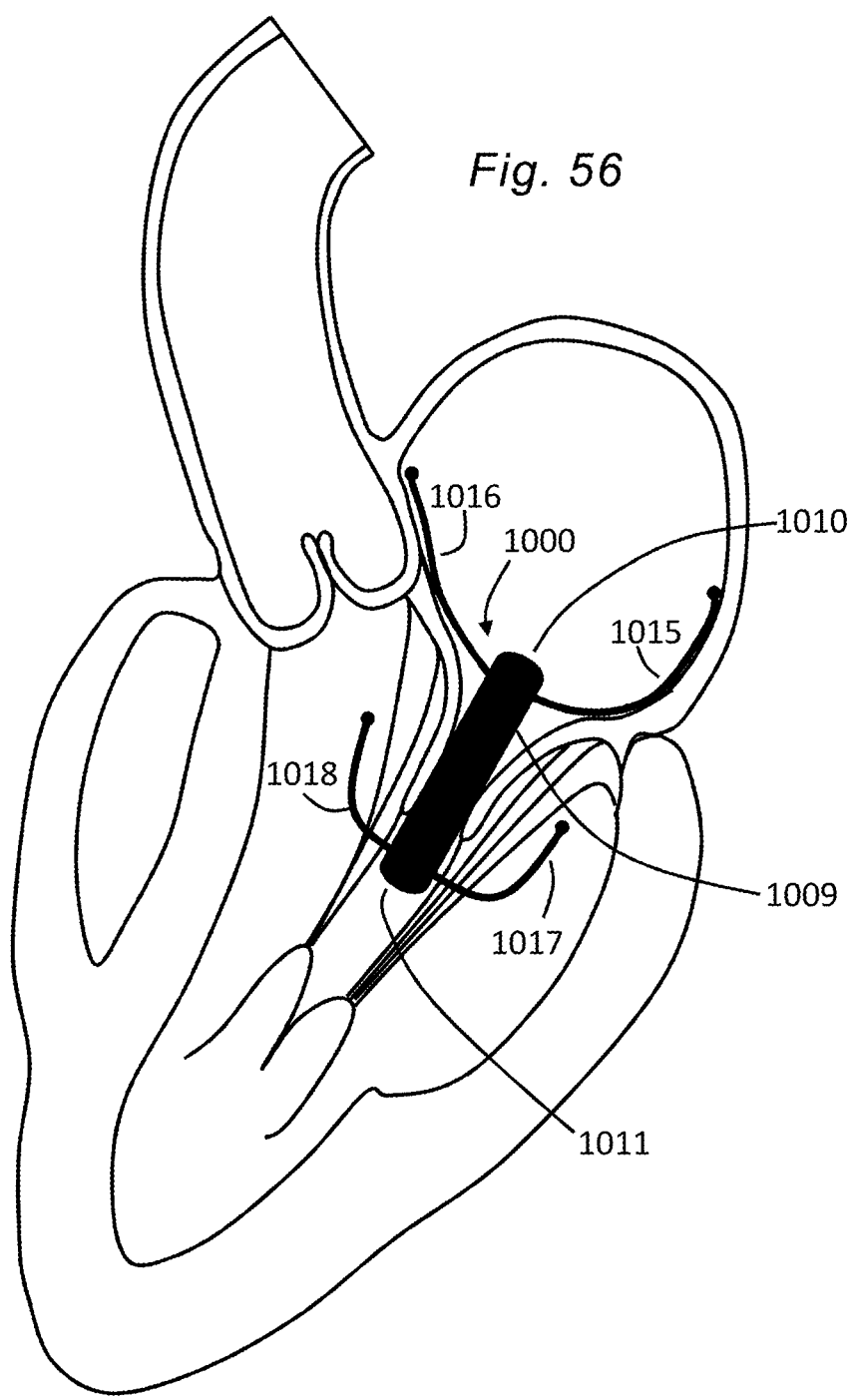
FIG. 56 shows a portion of a human heart with an exemplary embodiment of a sealing device similar to one as shown in FIG. 48 placed in the native mitral leaflet.

FIG. 56 shows a portion of human heart wherein an exemplary of device similar to that shown in FIG. 48 is deployed in the mitral valve.

Figure 57:
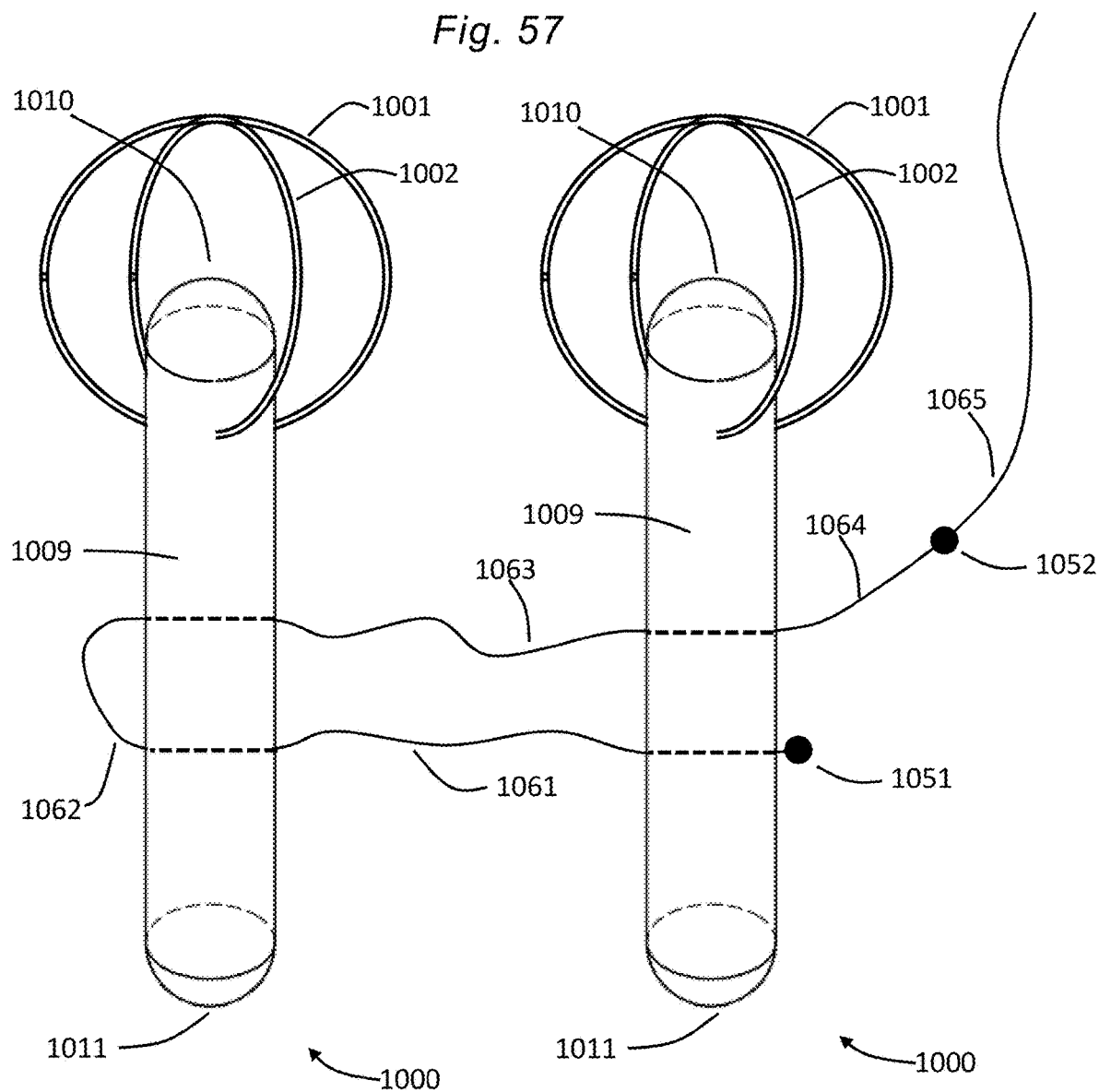
FIG. 57 shows two embodiments of the prosthetic device held together by strings and crimps

FIG. 57 shows an example of embodiment where two embodiments 1000 are stringed together using crimps 1051 and 1052. As can be seen, the string terminates at 1051 at the distal end and passes through both the bodies 1009, such that in the delivery catheter, they can be loaded in tandem. During deployment, the proximal crimp can be slid over to cinch the two bodies together and excess string cut off. FIGS. 58 and 59 show an alternate embodiment where the body 1079 is non-circular and the strings enter and exit from the atrial tip 1010 of the device. FIG. 59 shows the cinched configuration just prior to locking the proximal crimp and cutting the excess string 1074. It may be understood that while only a single string has been used to explain the concepts in FIGS. 57-59 to cinch the two bodies together, any combination of multiple strings or simple mechanical features may be used to reversibly or irreversibly assemble and lock the two bodies together.

Figure 60:
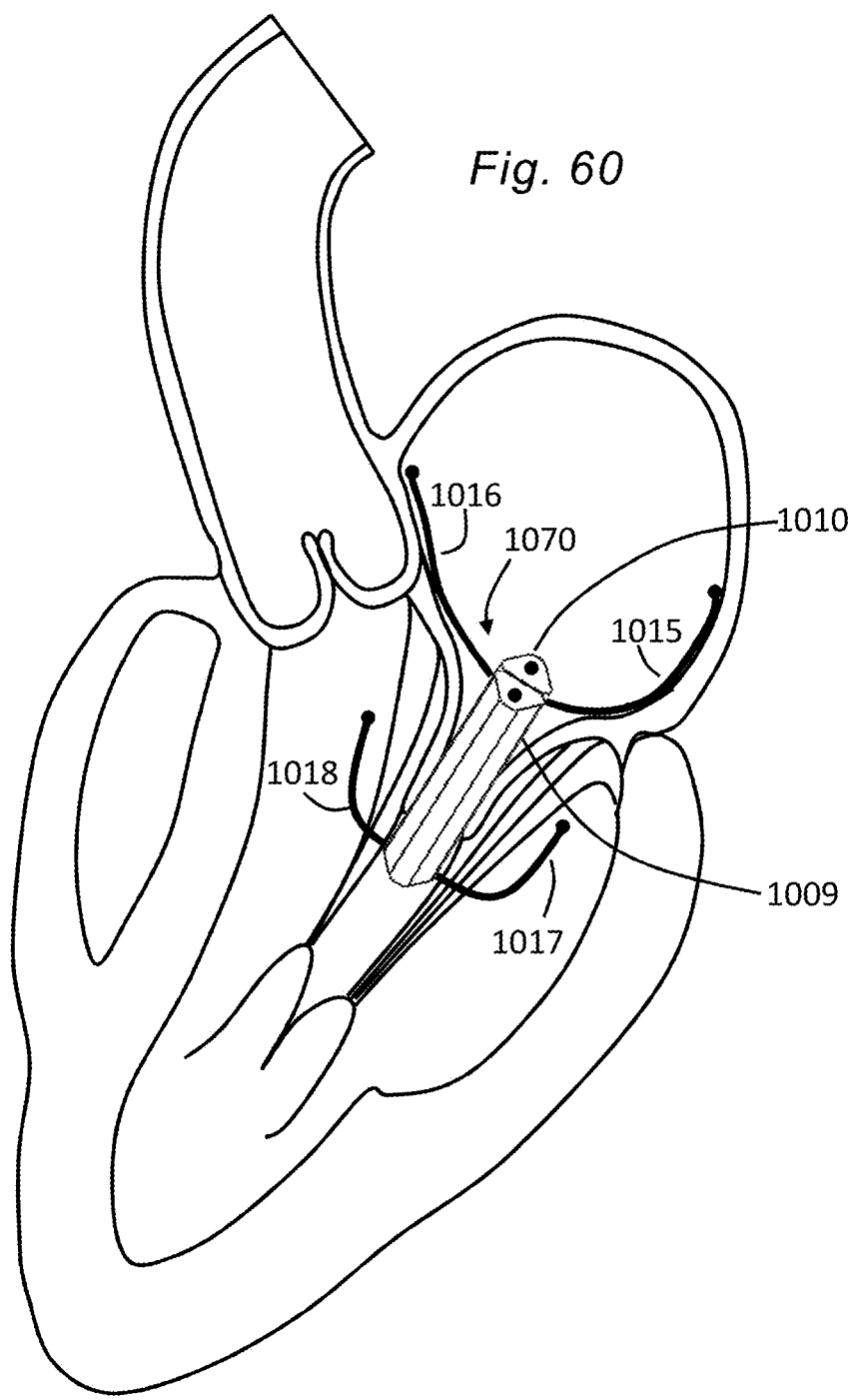
FIG. 60 shows a portion of a human heart with the alternate embodiment of the device from FIG. 59 with additional supporting members in the mitral valve

FIG. 60 shows a portion of human heart wherein an exemplary of device embodiment similar to that shown in FIG. 59 with additional atrial 1015, 1016 and ventricular 1017, 1018 supporting members, deployed in the mitral valve.

Any of the four approaches described in FIGS. 39-42 and deployment method described in FIGS. 12-15 can be applied to the device embodiments shown in FIGS. 44-55 and FIGS. 57-60 and/or their combinations.

Figure 61:
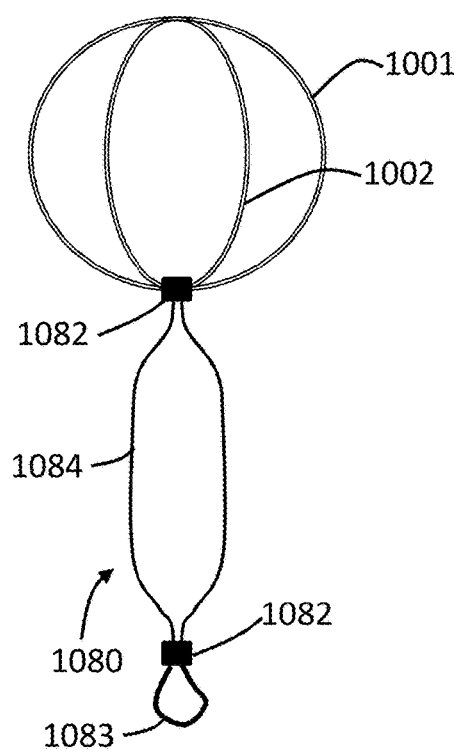
Figure 62:
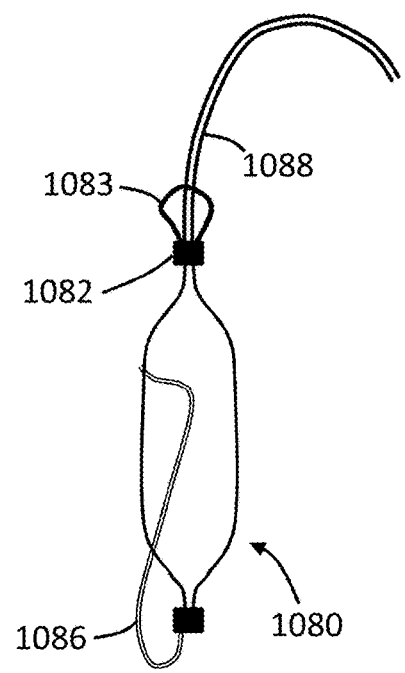

FIGS. 61-67 show exemplary embodiments based on balloons as spacers. FIG. 61 show an exemplary embodiment 1080 that has atrial stabilizers 1001, 1002. Additionally, it contains self-sealing ends 1082 with a loop 1083 that can be used for the purposes of retrieval of the implant at a later date post implantation. The retrieval loop contains radio-opaque pigments or markers. Although not shown for simplicity, the retrieval loop can be configured at either or both ends of the balloon across the exemplary embodiments depicted in FIGS. 61-67. In addition to aiding retrieval, the loops may be used to stabilize the balloon during inflation or deflation of the balloon using a detachable inflation shaft as shown in FIG. 62. Any obvious detachable interface common to catheter industry may be used. For example, interface 1082 can be configured with self-sealing elastomers such as polyurethane or silicone with durometer between 20 and 60 and an ejectable needle-based catheter similar to that explained in U.S. Pat. No. 9,351,862 B2, the full disclosure of which is incorporated herein by reference.

Figure 63:
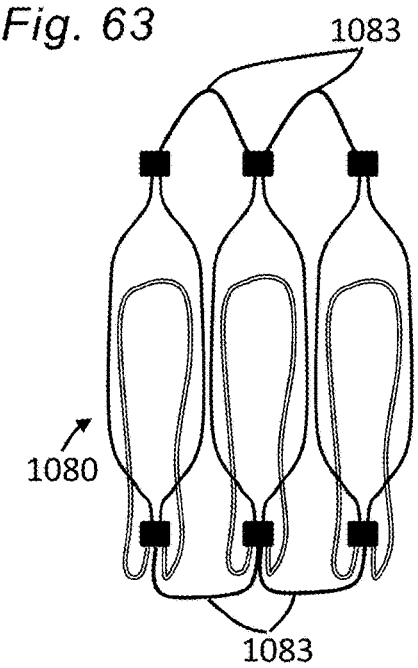

FIG. 63 shows an exemplary embodiment consisting of a side-by-side stack of 3 balloons. All 3 balloons may be configured to be inflated simultaneously or individually. Although not shown, these balloons may be covered individually or in a single hemocompatible sheet. This, to cover gaps and other features to provide a smooth enclosure that may or may not be configured to promote tissue in-growth.

Figure 64:
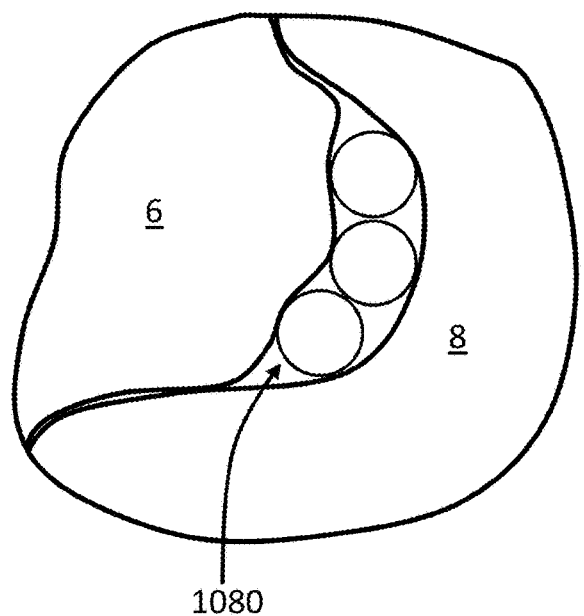

FIG. 64 shows show an exemplary 3 balloon spacer 1080 positioned within a native mitral valve.

FIGS. 65-67 show an alternate exemplary configuration of a single balloon design with a wide body shape 1094. FIG. 65 shows front view while FIG. 66 shows side view. However, the shape of the balloon may be configured as appropriate (for example in a crescent shape). Alternatively, the balloon may be configured to be flexible (and/or compliant) to auto conform to the shape of the gap in the mitral valve, for example, as shown in FIG. 67.

Retrieval of the implanted device 1080, 1090 may be performed using common interventional techniques. For example, a guide shaft is inserted to close proximity of the spacer device 1080 and a grasper can be then used to grasp a typical retrieval loop 1083 which can be used to cinch support structures 1001, 1002 and/or approximate the balloon end 1082 with the catheter shaft. A needle catheter can then be used to pierce into the balloon end 1082 and deflate the balloon. Once the body of the balloon 1084, 1094 is deflated, the entire device can then be retracted into the catheter shaft and retrieved out of the body.

Figure 68:
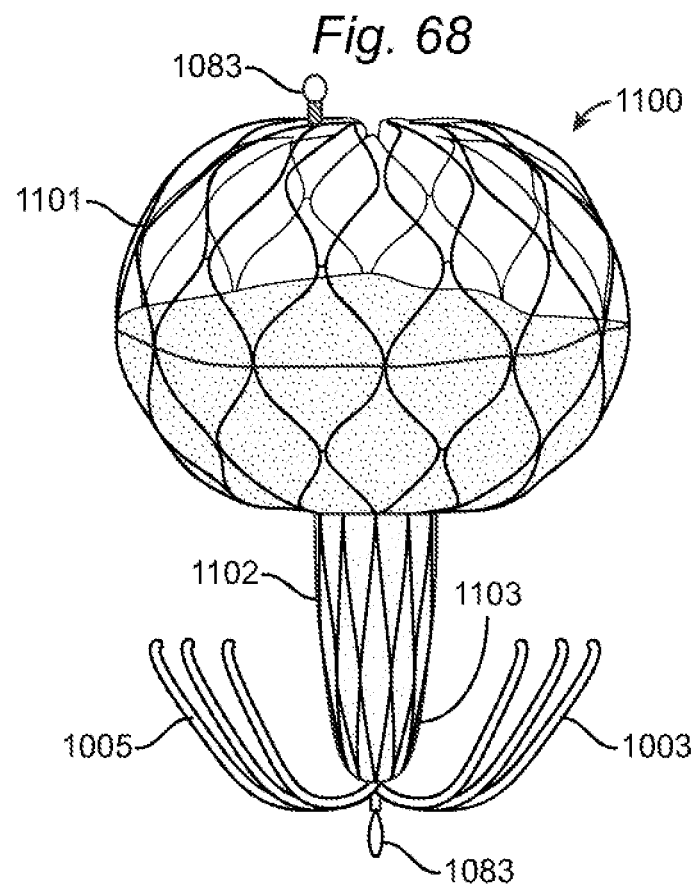
FIGS. 68-72 show exemplary embodiments showing a version of FIGS. 44-47 with stent-like configuration.
Figure 69:
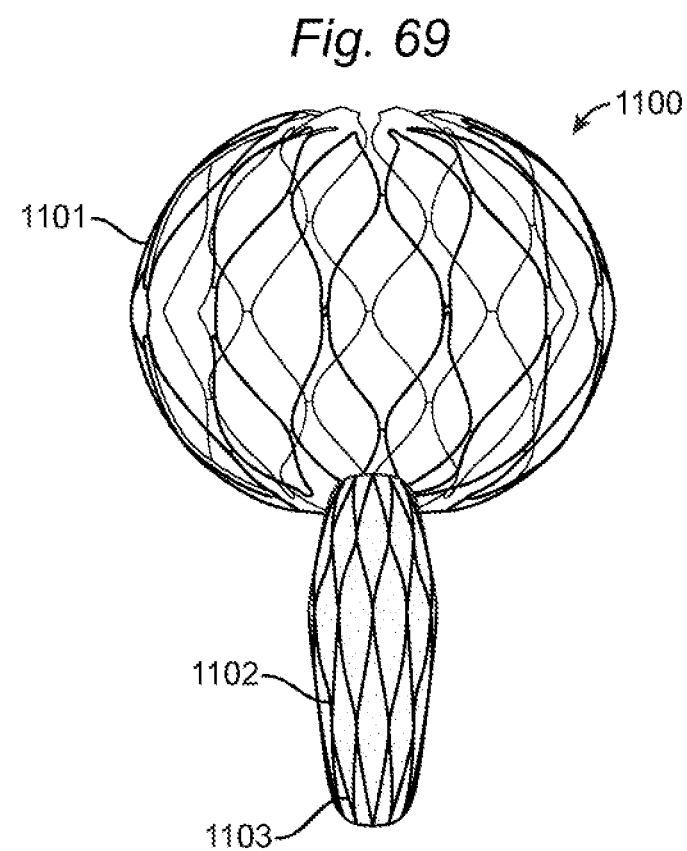
Figure 70:
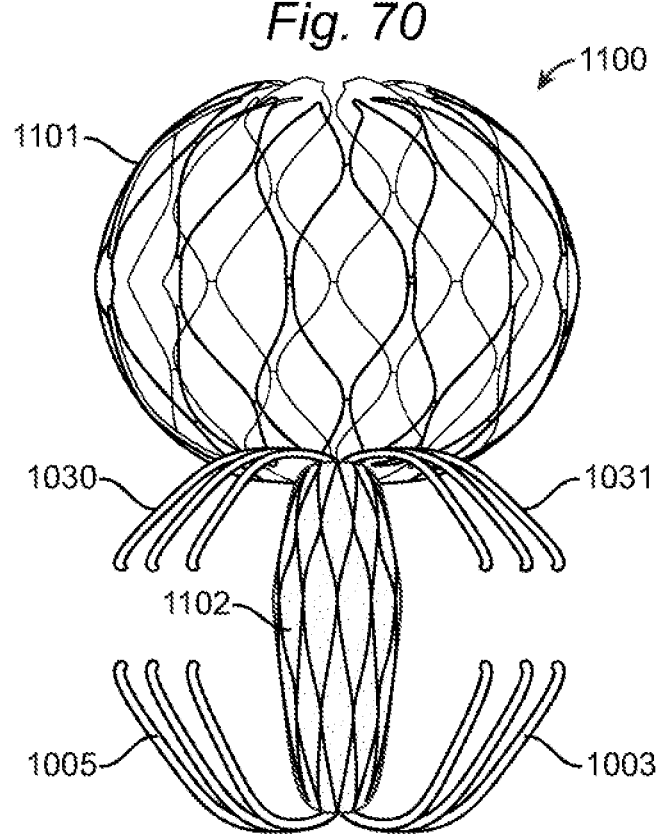
Figure 71:
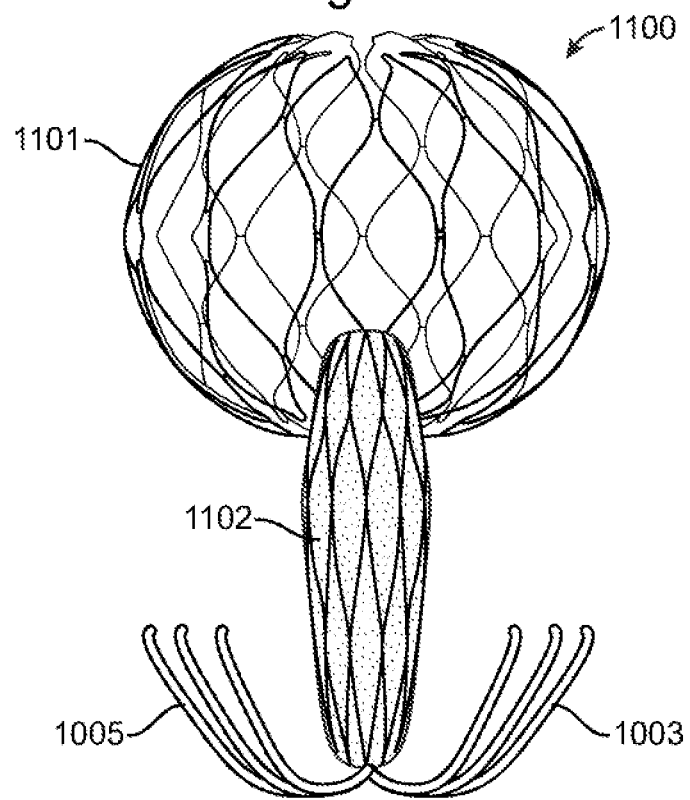
Figure 72:
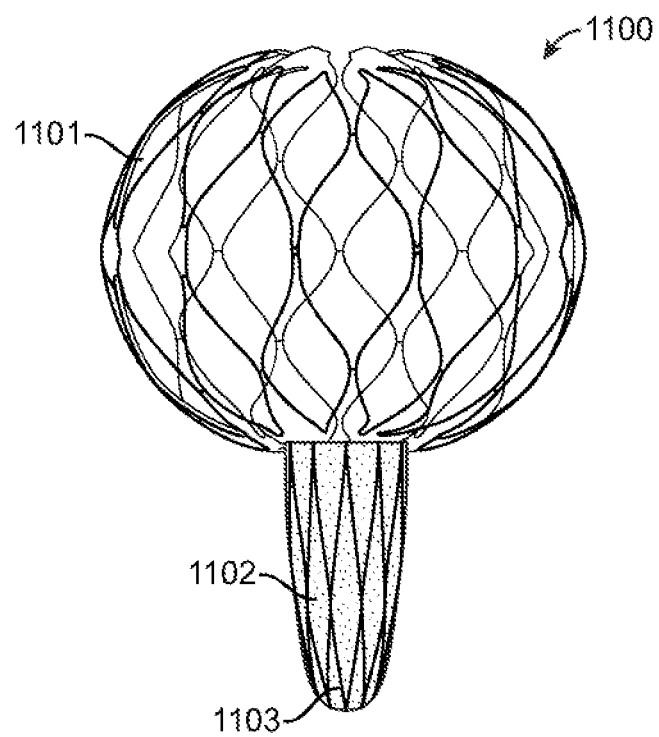
Figure 73:
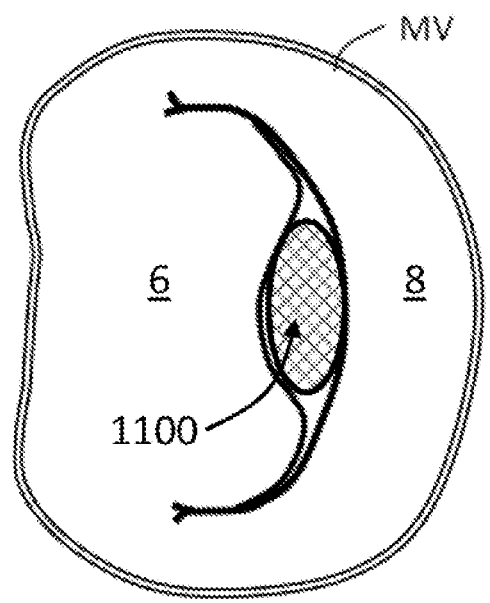
FIG. 73 shows atrial view of the mitral valve with this version of the embodiment.

FIGS. 68-73 show an alternate exemplary configuration 1100 that is similar to spacer device 1080, however, instead of a balloon, the spacer body 1102 is based on an expandable covered stent. FIG. 68 shows an exemplary embodiment with atrial support structure 1101 that is partially covered with a fabric. FIG. 69 shows an alternate exemplary embodiment with bare atrial stent based support structure 1101 and covered stent based spacer 1102. FIG. 70. Shows the embodiment shown earlier in FIG. 69 with atrial 1030, 1031 and ventricular 1003, 1005 support structures/anchors. FIG. 71 shows an alternate embodiment with spherical atrial support structure 1101 and ventricular support structures 1003, 1005.

Retrieval of the implanted device 1100 may be performed using common interventional techniques. For example, a typical guide shaft is inserted to close proximity of the spacer device 1100 and a grasper can be then used to grasp a typical retrieval loop 1083 (as shown in FIG. 68) with typical cinch cable that can be used to cinch support structures 1001, 1003, 1005, 1030, 1031 and/or the body 1102 into the shaft. The entire device 1100 can then be retracted into the catheter shaft and retrieved out of the body.

Leaf-Spring

Grasping will preferably be atraumatic, which provides a number of benefits. By atraumatic, it is meant that the devices and methods of the invention may be applied to the valve leaflets and then removed without causing any significant clinical impairment of leaflet structure or function. The leaflets and valve continue to function substantially the same as before the invention was applied. Thus, some minor penetration or denting of the leaflets may occur using the invention while still meeting the definition of "atraumatic". This enables the devices of the invention to be applied to a diseased valve and, if desired, removed or repositioned without having negatively affected valve function. In addition, it will be understood that in some cases it may be necessary or desirable to pierce or otherwise permanently affect the leaflets during either grasping, fixing or both. In some of these cases, grasping and fixation may be accomplished by a single device. Although a number of embodiments are provided to achieve these results, a general overview of the basic features will be presented herein. Such features are not intended to limit the scope of the invention and are presented with the aim of providing a basis for descriptions of individual embodiments presented later in the application.

The devices and methods of the invention rely upon the use of an interventional tool that is positioned near a desired treatment site and used to grasp the target tissue. In endovascular applications, the interventional tool is typically an interventional catheter. In surgical applications, the interventional tool is typically an interventional instrument. In preferred embodiments, fixation of the grasped tissue is accomplished by maintaining grasping with a portion of the interventional tool which is left behind as an implant. While the invention may have a variety of applications for tissue approximation and fixation throughout the body, it is particularly well adapted for the repair of valves, especially cardiac valves such as the mitral valve and tricuspid valve.

The prosthetic device can be configured to be implanted via a delivery sheath. The body and the anchor can be a solid or hollow, compressible or incompressible and rigid or flexible. In some embodiments, the body and anchor comprise of leaf-springs. The device can be configured to allow the anchor to self-expand radially or laterally away from the body initially in order to create a gap between the body and the anchor. The leaflet can then be positioned in the gap. The body can then be allowed to contact the leaflet, closing the gap between the body and the anchor and capturing the leaflet between the body and the anchor. The implantation methods for various embodiments can be different, and are more fully discussed below with respect to each embodiment.

Some embodiments disclosed herein are generally configured to be secured to only one of the native mitral leaflets. However, other embodiments comprise more than one anchor and can be configured to be secured to both mitral leaflets. Further, there are other embodiments with anchors that allow for retrieval of the implanted body at a later date. Unless otherwise stated, any of the embodiments disclosed herein that comprise a single anchor can optionally be secured to the anterior mitral leaflet or secured to the posterior mitral leaflet, or secured to both regardless of whether the particular embodiments are shown as being secured to a particular one of the leaflets.

Some embodiments disclosed herein are generally configured with an anchor or anchor-like support structures that have coatings or coverings to promote tissue incorporation over chronic conditions. However, other embodiments comprise of biocompatible coatings or coverings that promote minimal or no tissue ingrowth—so as to enable device retrieval/removal at a later date. Unless otherwise stated, any of the embodiments may be configured to a) fully incorporate tissue, b) partially incorporate tissue, or c) minimal to no incorporation of tissue or a combination of tissue incorporation at various sites of the device, regardless of whether the particular embodiments are shown as being covered or coated.

Furthermore, some embodiments can optionally also include one or more atrial and/or ventricle anchors, such as to provide additional stabilization. Unless otherwise stated, any of the embodiments disclosed herein can optionally include an atrial (and/or ventricle) anchor or not include an atrial (and/or ventricle) anchor, regardless of whether the particular embodiments are shown with an atrial (and/or ventricle) anchor or not.

Figure 74:
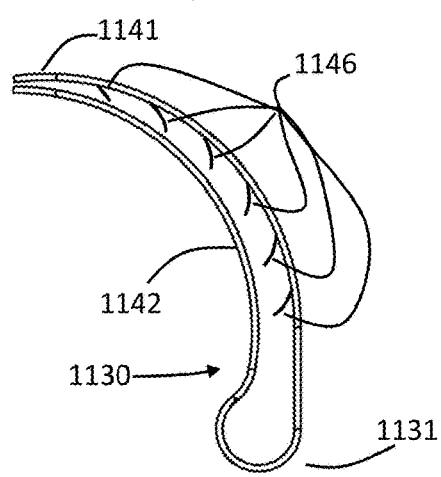
FIG. 74 shows an exemplary embodiment of a device configured to capture any one of the anterior or posterior leaflets.
Figure 75:
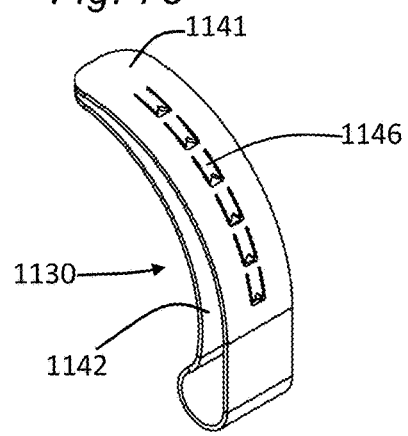
FIG. 75 shows 3D view of the exemplary embodiment shown in FIG. 74.

FIG. 74 shows an exemplary embodiment of a prosthetic device 1130 that comprises of an atrial leaf-spring segment 1141 and a ventricular leaf-spring segment 1142 that are continuous with a third leaf-spring at the base 1131. Either atrial and/or ventricular leaf-springs 1141, 1142 can have anchors or barbs or frictional elements (exemplary atrial frictional elements 1146 are shown in FIGS. 74 and 75. These anchors can be configured to be atraumatic and designed to release or restrain the tissue depending on the gap between the two leaf-springs 1141, 1142. The gap between the leaf-springs 1141 and 1142 can be manipulated using prevalent intervention catheter technology such as pulling the atrial leaf-spring 1141 using a sutures or wires while restraining the ventricular leaf-spring 1142 using catheter shaft and/or sutures/wires and/or custom delivery mechanisms.

FIG. 75 shows the 3D view of the exemplary embodiment shown in FIG. 74. In this as well as subsequent similar views, the barbs are shown in a straightened configuration for ease of illustration.

Figure 76:
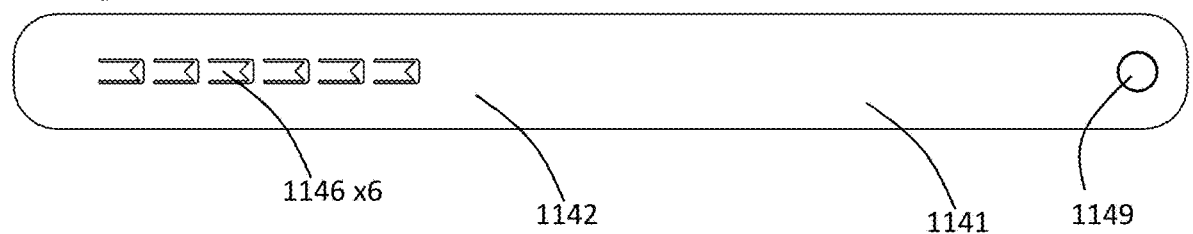
FIG. 76 shows the (sheet metal) laser-cut flat pattern of the exemplary embodiment shown in FIG. 74.

While FIG. 76 shows one exemplary manufacturing method of making the device embodiment 1130 using laser-cut sheet metal of drawn strip. In one embodiment, the device 1130 can be made of superelastic nitinol. In other embodiments, the device 1130 can be made of elastic polymers, metals, ceramics of the combinations of thereof.

Figure 77:
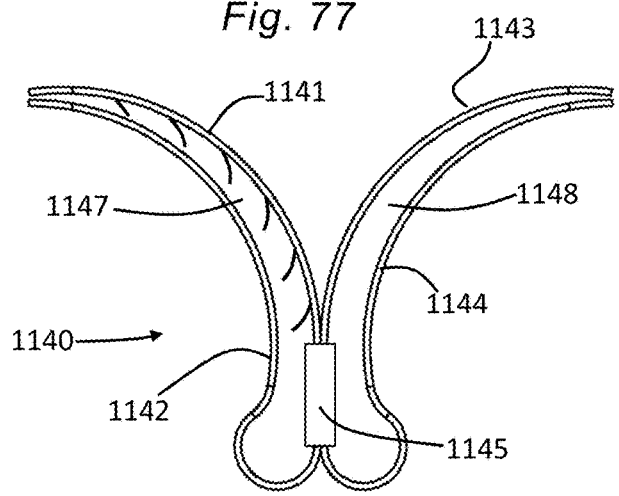
FIG. 77 shows an exemplary embodiment of a device that is formed by combining two of the exemplary embodiment shown in FIG. 74. This, to capture each of the anterior and posterior leaflets.

FIG. 77 shows an exemplary embodiment of device 1140, which is formed using two devices 1130 (as shown previously in FIG. 74), which are fastened/bonded/welded/crimped together at the base, in this case using a tubular member 1145. Each sheet metal component as has an atrial side 1141 (or 1143) and a ventricular side 1142 (or 1144). The atrial (and or ventricle) side may have barbs 1146 (or frictional elements) to hold on to the leaflets in the spaces 1147 and 1148.

Figure 78:
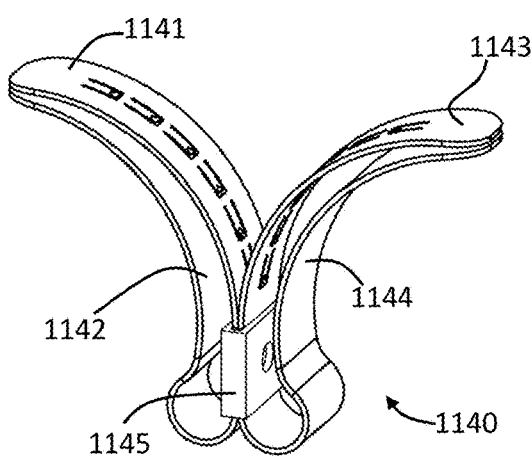
FIG. 78 shows 3D view of the exemplary embodiment of shown in FIG. 77.

FIG. 78 shows 3D view of the exemplary embodiment 1140 as shown in FIG. 77.

FIGS. 79-81 illustrate an exemplary method of deployment of the device 1140 from a delivery catheter 1150. In FIG. 79, the device 1140 is shown partially within the catheter 1150 with the atrial leaf-springs 1141, 1143 extending proximally while ventricular leaf-springs 1142, 1144 are extended distally, in a straightened, or unfurled, state. A pusher member 1151 can be used to push the device 1140 distally relative to the catheter 1150 or to hold the device 1140 steady as the catheter is retracted. In FIG. 80, the catheter 1150 is retracted proximally from the device 1140 and/or the device 1140 is advanced distally from the catheter 1150 such that the ventricular leaf-springs 1142, 1144 begin to extend out of the distal end 1156 of the catheter. As the leaf-springs 1142, 1144 move out of the distal edge 1156, the leaf-springs 1142, 1144 begins to elastically rebound to its predetermined shape. This elastic rebounding action can be used to grab and position the mitral leaflet within the gap 1153, 1154 while the device is in the configuration. In FIG. 81, the entire device 1140 has moved out of the catheter 1150 and the all leaf springs 1141, 1142, 1143 and 1144 have returned to their natural shape of FIG. 77, while, the leaflets remain captured/anchored within the gaps 1147 and 1148.

FIGS. 82-84 illustrate an exemplary method of deployment of the device 1140 from a delivery catheter 1157, wherein, the user can sequentially grab and/or constrain one leaflet at a time. This method is slightly modified method as illustrated and described earlier in FIGS. 79-81, wherein, all components except the distal end of the catheter shaft 1157 is stepped that is, there is a leading distal edge 1156 and a trailing edge 1155 as shown in FIG. 85. In FIG. 82, the device 1140 is shown mostly within the catheter 1157 with the atrial leaf-springs 1141, 1143 extending proximally while ventricular leaf-springs 1142, 1144 are extended distally, in a straightened, or unfurled, state. A pusher member 1151 can be used to push the device 1140 distally relative to the catheter 1157 or to hold the device 1140 steady as the catheter is retracted. In FIG. 83, the catheter 1157 is retracted proximally from the device 1140 and/or the device 1140 is advanced distally from the catheter 1150 such that owing to the offset 1155, leaf spring 1144 elastically rebounds first, while leaf spring 1140 is still constrained in a straight position by distal segment 1156 of the shaft 1157. Thus, allowing the user to selectively grab and/or restrain one leaflet in the space 1153. In FIG. 84, the user then retracts and/or pushes the device 1140 further out to the catheter 1157 such that the $2^{nd}$ ventricular leaf-springs 1142 too elastically rebounds to allow the user to now grab and/or constrain the $2^{nd}$ leaflet. Once both leaflets are grabbed and/or constrained, the user can then fully deploy the device 1140, wherein, the leaflets are constrained within the spaces 1147 and 1148 of the device. In some embodiments, the free ends of the leaf-springs can be manipulated using levers or suture. For example, the free ends of atrial leaf-springs 1141 and 1143 can be manipulated using sutures to lift the leaf-springs 1141 and 1143 either sequentially or simultaneously off the leaflets, to allow for repositioning and/or recapture of the leaflets. In the same lines, a retrieval suture loop with radio-opaque markers may be attached across the two free ends of the leaf-springs 1141, 1143.

Figure 86:
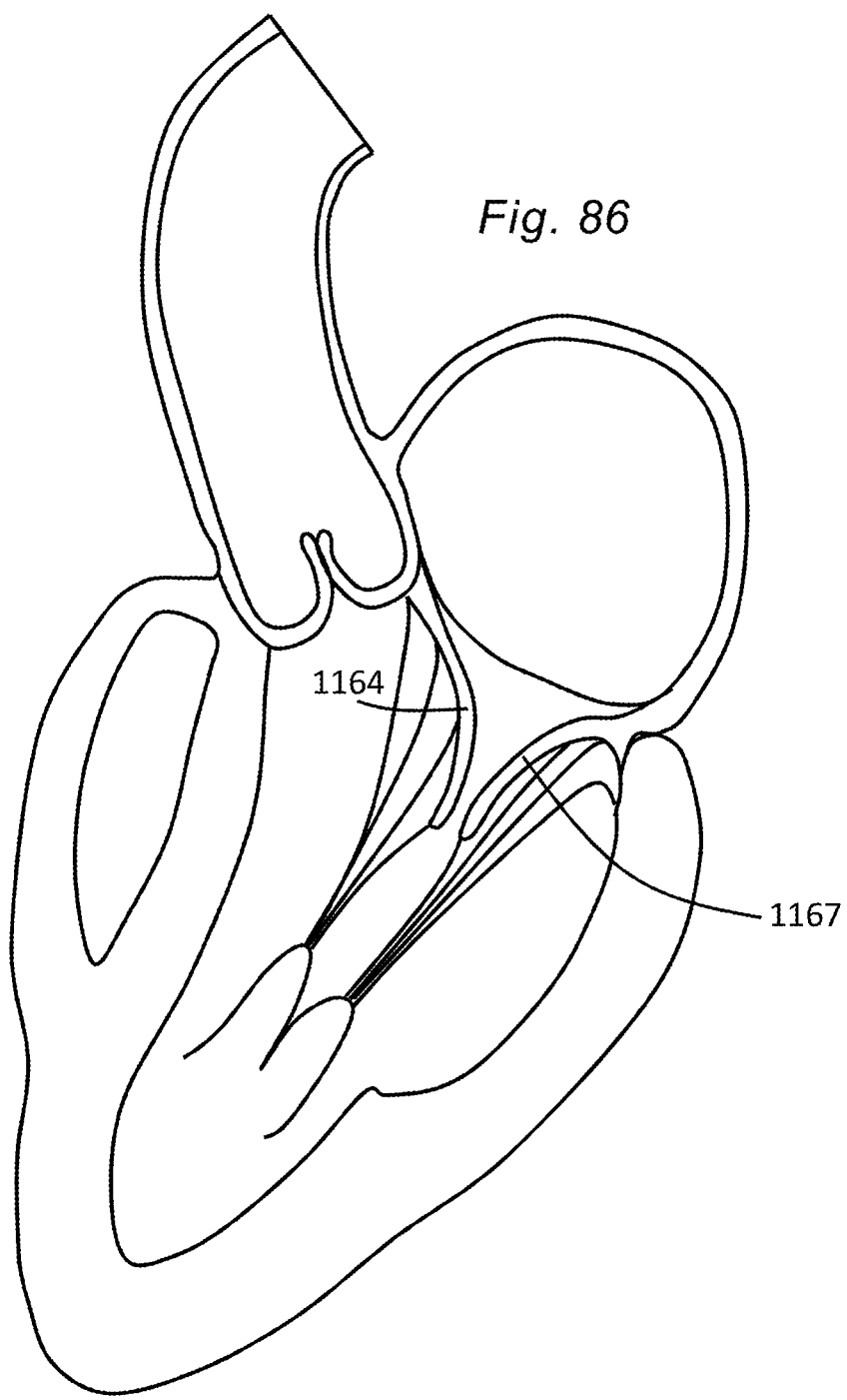
FIG. 86 shows a portion of human heart cross-section schematic, showing left atrium, left ventricle and mitral valve.
Figure 87:
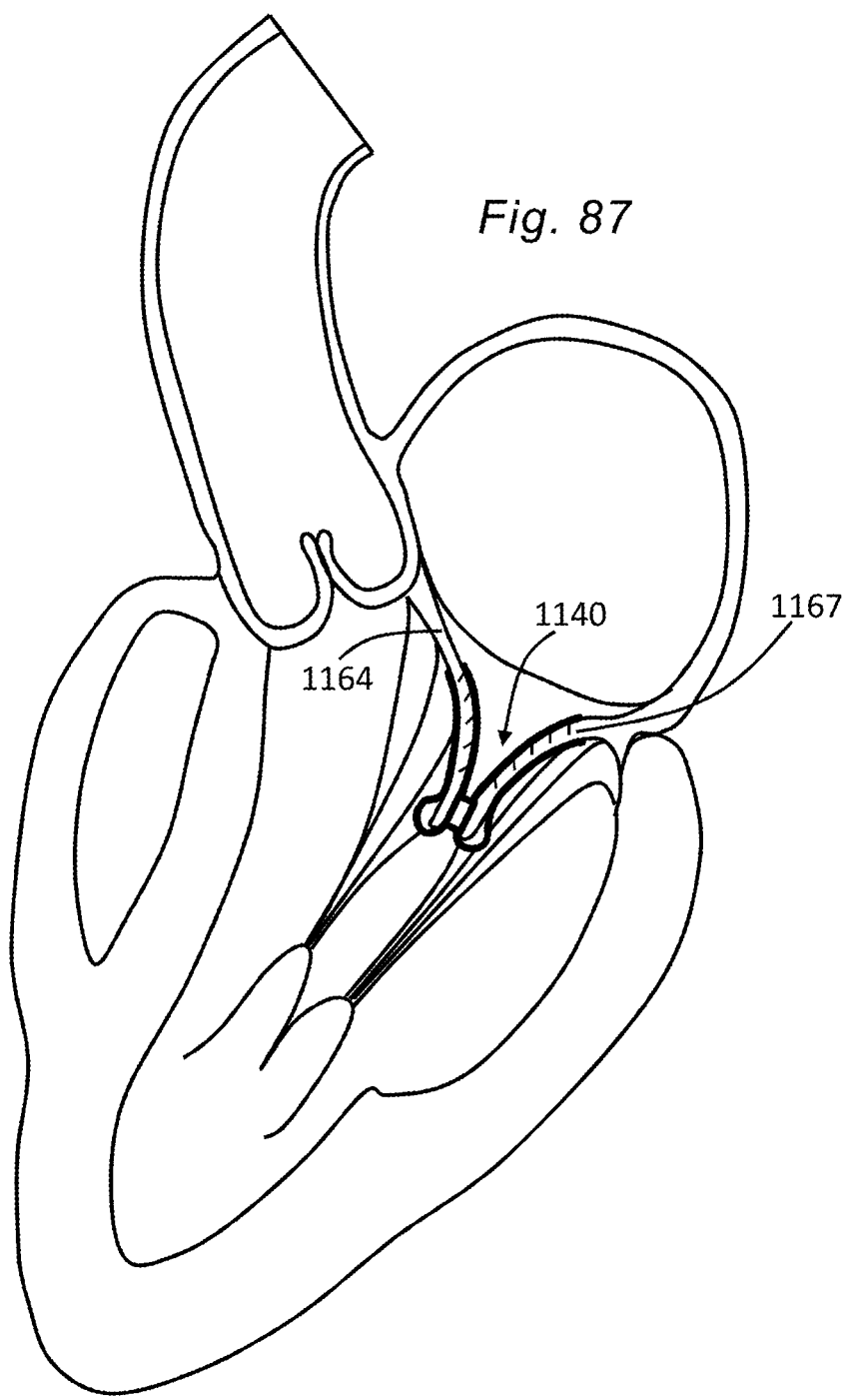
FIG. 87 shows a portion of a human heart with an exemplary embodiment of the device shown in FIG. 77 placed in the native mitral leaflet.

FIG. 86 shows a schematic cross-section of heart with anterior 1164 and posterior 1167 mitral valve leaflets. FIG. 87 shows an example of the device 1140 deployed within mitral valve leaflets.

Figure 88:
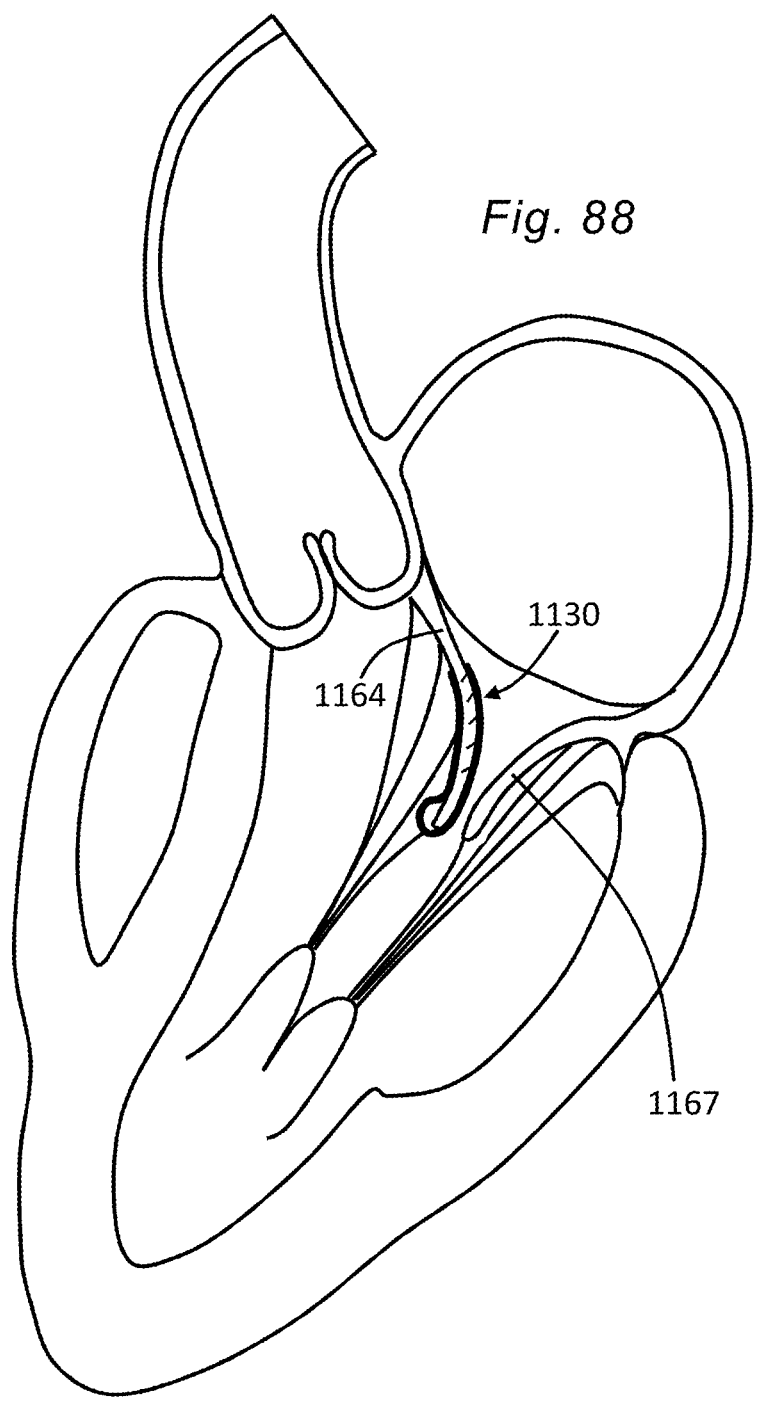
FIG. 88 shows a portion of a human heart with an exemplary embodiment of the device shown in FIG. 74 placed in the native mitral leaflet.

FIG. 88 shows an example of the device 1130 (as in FIG. 74) deployed in one of the mitral valve leaflets.

Figure 89:
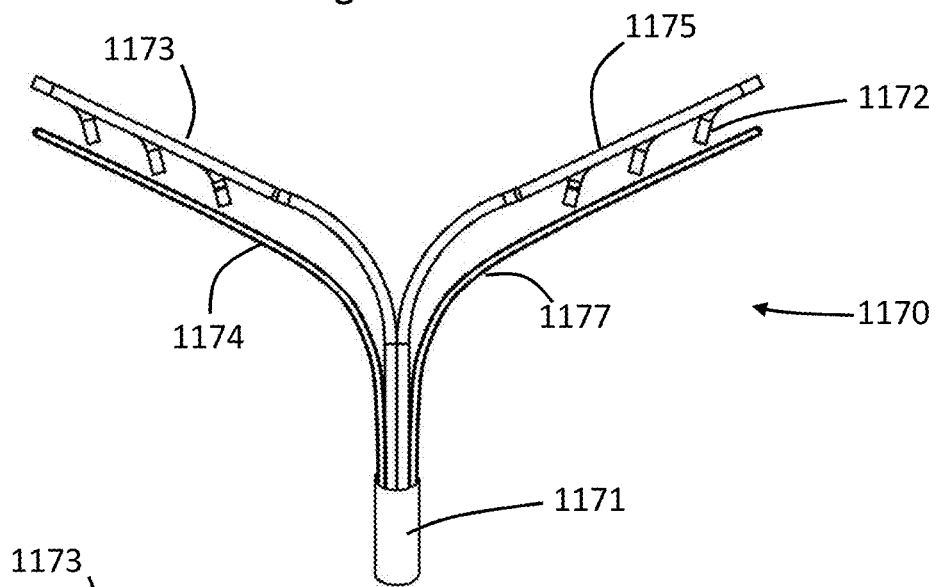
FIG. 89 shows and exemplary embodiment of a device made of sheet metal and wire.
Figure 90:
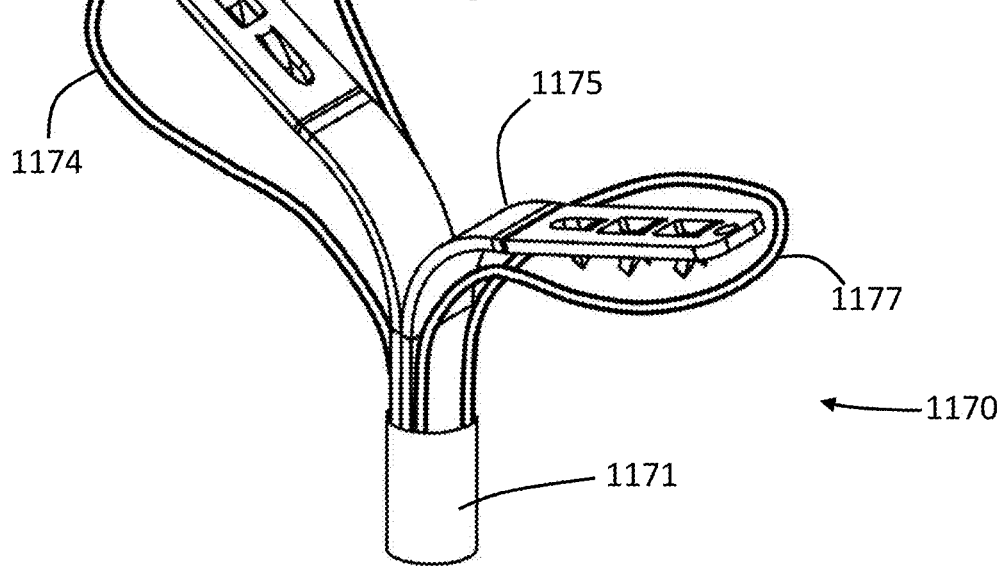
FIG. 90 shows 3D view of the embodiment shown in FIG. 89.
Figure 91:
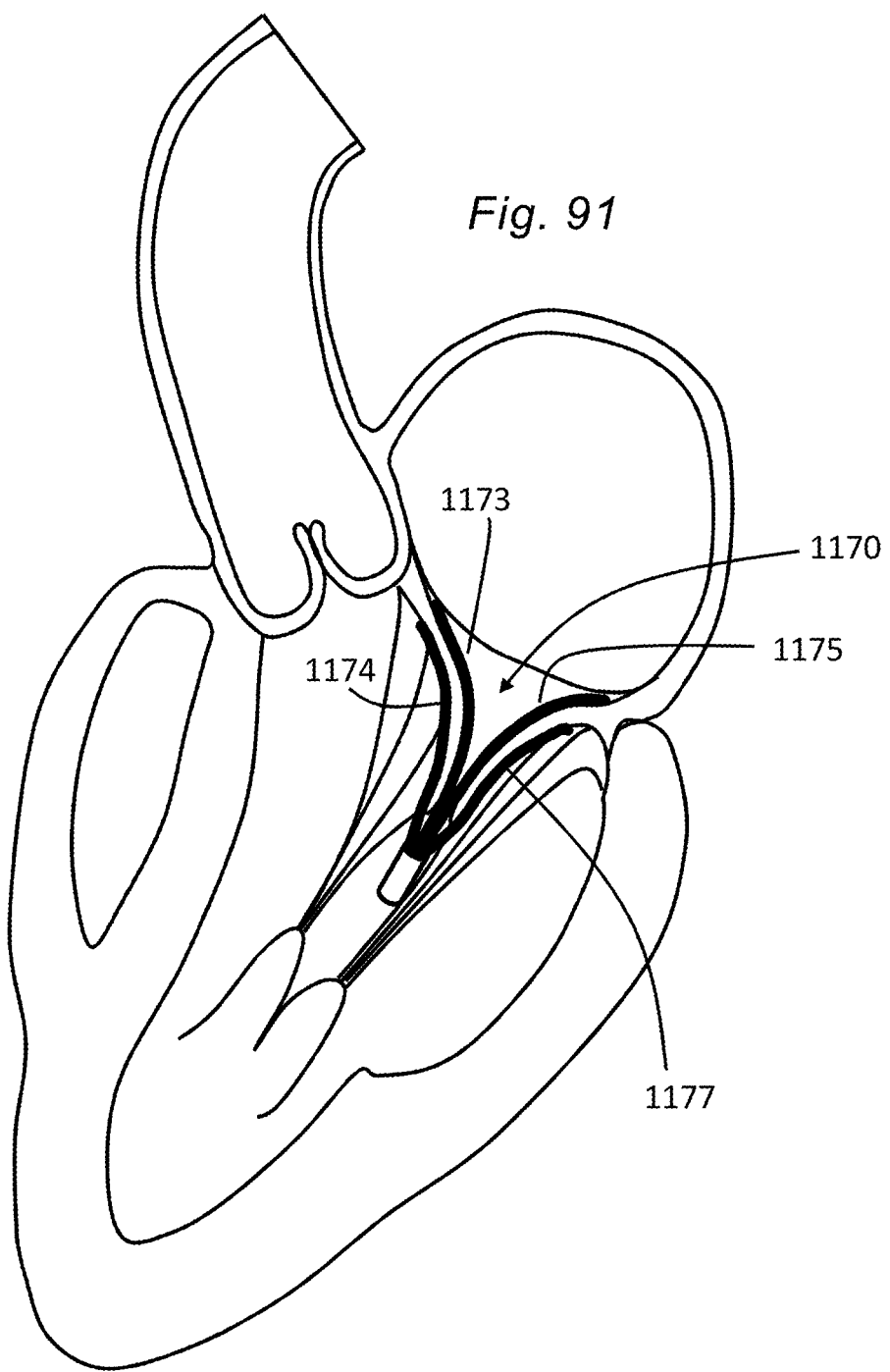
FIG. 91 shows a portion of a human heart with an exemplary embodiment of the device shown in FIG. 89 placed in the native mitral leaflet.

FIG. 89 shows and exemplary device 1170 that is a combination of leaf springs 1173, 1175 and wire loops 1174, 1177. FIG. 90 shows 3D view of device 1170. The advantages of this design are: a) the wire loop can be loaded in a compress state while inside catheter and expand laterally on deployment which in effect increases the area of leaflet restraint, b) The leaf springs add structural stability to the device, complementing the wire loops, and c) the frictional elements or barbs 1172 on the leaf springs can be configured to atraumatically grasp, secure and/or restraint the leaflets. While the exemplary device 1170 is shown with leaf springs to grasp the leaflets from the atrial side and wire loops in the ventricular side of the leaflets as shown in FIG. 91, in some embodiments, the leaf spring may be on the ventricular side and wire loops on the atrial side, and/or a combination of thereof.

Commonly known interventional and minimally invasive techniques may be used to deploy any of the devices described herein. For example, some of the approaches may be trans-septal, trans-apical, trans-atrial, and trans-aortic valve.

Spacer Leaf-Spring

In some embodiments, a prosthetic device comprises a body and an anchor. The body is configured to be positioned within the native mitral valve orifice to help create a more effective seal between the native leaflets to prevent or minimize mitral regurgitation. The body can comprise a structure that is impervious to blood and that allows the native leaflets to close around the sides of the body during ventricular systole to block blood from flowing from the left ventricle back into the left atrium. The body is sometimes referred to herein as a spacer because the body can fill a space between improperly functioning native mitral leaflets that do not naturally close completely.

The body can be elastic or inelastic or compressible or incompressible or flexible or a combination of thereof.

The body can be make of leaf spring or have leaf spring like features and can be made of sheet, strip, wire, and/or fibers.

Anchors and/or support members can be configured to secure the device to one or both of the native mitral leaflets and/or the annulus such that the body is positioned between the two native leaflets. The anchor can attach to the body at a location adjacent the ventricular end, atrial end, and/or the annulus of the body. The anchor can be configured to be positioned above and/or behind a native leaflet when implanted such that the leaflet is captured between the anchor and the body. Alternatively, the anchor can be configured to be positioned to constrain the device with some freedom to move between the native leaflets or annulus when implanted.

The anchors can be contiguous or extension of the body and/or separately attached to the body. Either or both the anchors and body can have leaf spring like features.

The prosthetic device can be configured to be implanted via a delivery sheath. The body and the anchor can be a solid or hollow, compressible or incompressible and rigid or flexible. The device can be configured to allow the anchor to self-expand radially or laterally away from the body initially to create a gap between the body and the anchor. The leaflet can then be positioned in the gap. The body can then be allowed to contact the leaflet, closing the gap between the body and the anchor and capturing the leaflet between the body and the anchor. The implantation methods for various embodiments can be different, and are more fully discussed below with respect to each embodiment. Additional information regarding these and other delivery methods can be found in U.S. Pat. No. 9,414,918 B2, previously incorporated herein by reference.

Some embodiments disclosed herein are generally configured to be secured to only one of the native mitral leaflets. However, other embodiments comprise more than one anchor and can be configured to be secured to both mitral leaflets. Further, there are other embodiments with anchors that allow for retrieval of the implanted body at a later date. Unless otherwise stated, any of the embodiments disclosed herein that comprise a single anchor can optionally be secured to the anterior mitral leaflet or secured to the posterior mitral leaflet, or secured to both regardless of whether the particular embodiments are shown as being secured to a particular one of the leaflets.

Some embodiments disclosed herein are generally configured to be secured to the annulus. Some embodiments disclosed herein are generally configured to be secured and/or supported by the atrial wall or features. Some embodiments disclosed herein are generally configured to be secured and/or supported by the ventricular wall or features. Some embodiments disclosed herein are generally configured to be secured and/or supported by the atrial wall and/or ventricular wall and/or annulus and/or leaflets and/or chordae and/or other heart features.

Some embodiments disclosed herein are generally configured with a leaf spring or anchor or anchor-like support structures that have coatings or coverings to promote tissue incorporation over chronic conditions. However, other embodiments comprise of biocompatible coatings or coverings that promote minimal or no tissue ingrowth—so as to enable device retrieval/removal at a later date. Unless otherwise stated, any of the embodiments may be configured to a) fully incorporate tissue, b) partially incorporate tissue, or c) minimal to no incorporation of tissue or a combination of tissue incorporation at various sites of the device, regardless of whether the particular embodiments are shown as being covered or coated.

Some embodiments can optionally also include one or more atrial and/or ventricle anchors, so as to provide additional stabilization. Unless otherwise stated, any of the embodiments disclosed herein can optionally include an atrial (and/or ventricle) anchor or not include an atrial (and/or ventricle) anchor, regardless of whether the particular embodiments are shown with an atrial (and/or ventricle) anchor or not.

Some of the disclosed prosthetic devices are prevented from atrial embolization by having the anchor hooked around a leaflet, utilizing the tension from native chordae tendinae to resist high systolic pressure urging the device toward the left atrium. During diastole, the devices can rely on the compressive forces exerted on the leaflet that is captured between the body and the anchor to resist embolization into the left ventricle.

Figure 92:
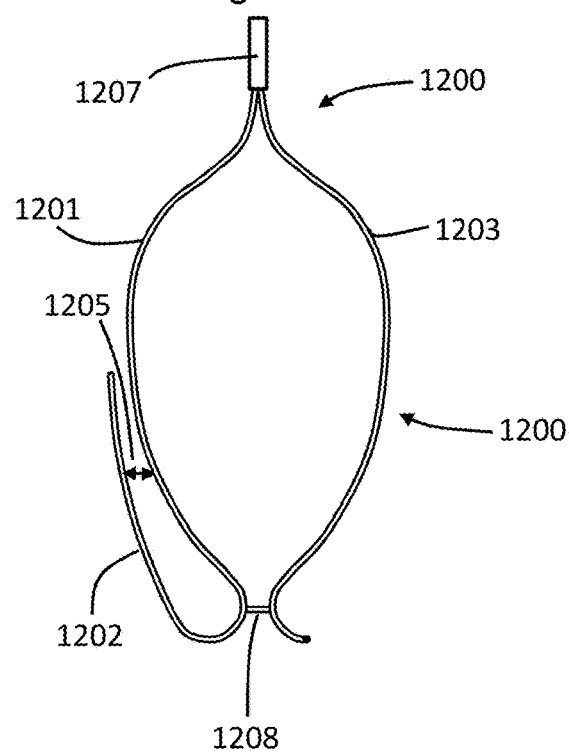
FIG. 92 shows an embodiment 1200 that is configured to engage with only one leaflet (for example, either anterior or posterior mitral valve leaflet).

FIG. 92 shows an exemplary embodiment of a prosthetic device 1200 that comprises a body made of leaf springs 1201, 1202, 1203. The body leaf springs are made of two continuous leaf springs attached together using a fastener, weld or tubular structure 1207. The area or volume within the body leaf springs can be covered with blood impermeable structure or fabric. Further, the body can be open cell (without locking structure 1208) or closed cell as shown in FIG. 92. The device 1200 is secured to the posterior mitral leaflet with the free end of the leaflet captured between the anchor 1202 and the body 1201 as shown by the gap 1205. As the mitral leaflets open apart from each other, the device 1200 can move with the posterior leaflet, allowing the anterior leaflet to open away from the device 1200. During systole, the back pressure on the leaflets closes them together around the device 1200 to prevent mitral regurgitation.

Figure 93:
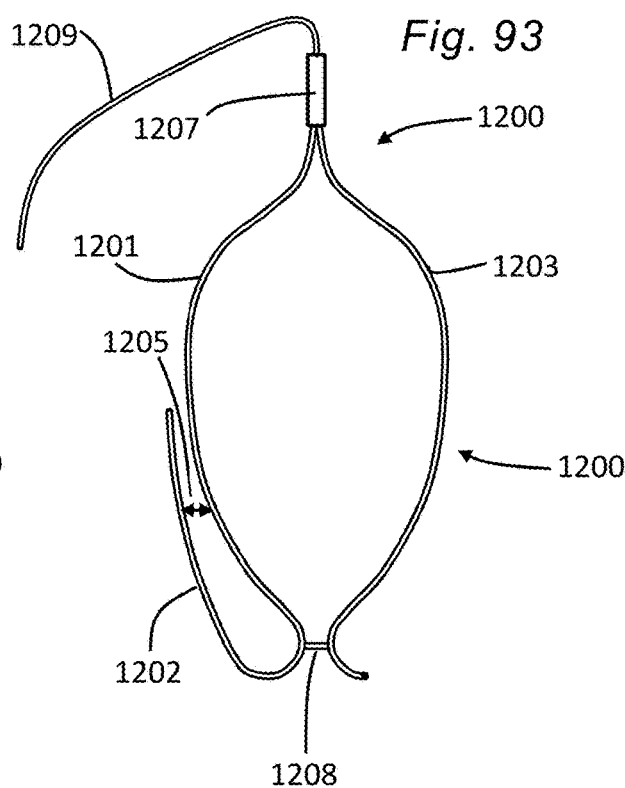
FIG. 93 shows an embodiment 1200 that is configured to engage with only one leaflet (for example, either anterior or posterior mitral valve leaflet) and additionally configured with an atrial support structure that prevents embolization as well as provides spatial constraint.

FIG. 93 shows device 1200 with an atrial support structure 1209. The atrial support structure 1209 can also help prevent the device 1200 from releasing (embolizing) into the left ventricle. The atrial support structure 1209 can comprise frictional elements and/or barbs.

Figure 94:
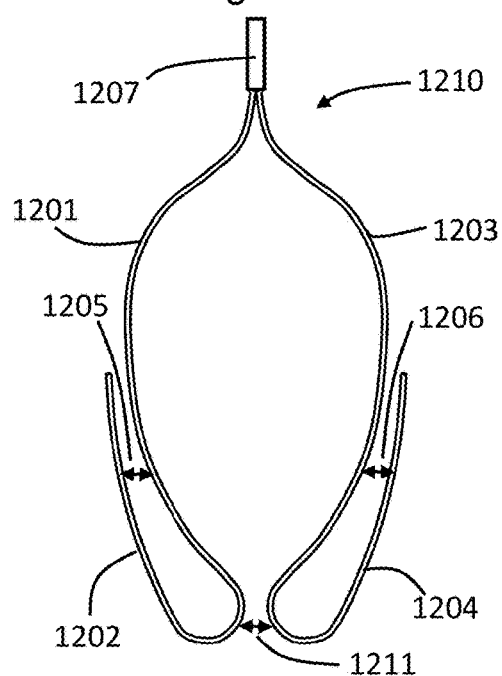
FIG. 94 shows an exemplary embodiment 1210 of a leaf spring spacer that is configured to capture two leaflets.

FIG. 94 shows a prosthetic device 1210 and is made of two continuous body leaf springs 1201, 1203 and anchor leaf springs 1202, 1204 that are attached together using a fastener, weld or tubular structure 1207. The area or volume within the body leaf springs can be covered with blood impermeable structure or fabric. Further, the body can be open cell (without locking structure 1208) or closed cell as shown in FIG. 92. The device 1210 is secured to both posterior and anterior leaflets. For example, the posterior mitral leaflet can be captured between the anchor 1202 and the body 1201 as shown by the gap 1205. While, the anterior mitral leaflet can be captured between the anchor 1204 and the body 1203 as shown by the gap 1206. As the mitral leaflets open apart from each other during diastole, there is a portion of leaflet still secured in the gaps 1205 and 1206, thus forming a combination of Alfieri edge to edge technique and a spacer to prevent mitral regurgitation. In case of open cell structure (without 1208), the gap 1211 can be configured to increase during diastole and/or decrease during systole and vice-versa.

Figure 95:
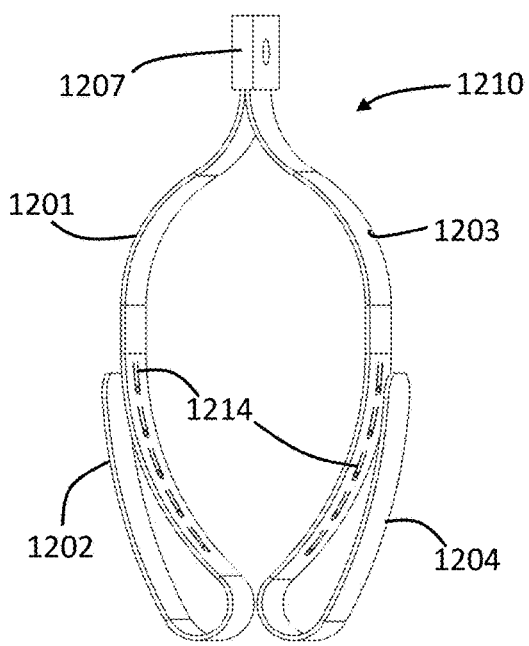
FIG. 95 shows 3D view of the embodiment of FIG. 94

FIG. 95 shows 3D view of prosthetic device 1210. Frictional elements or barbs 1214 may be used to further secure the leaflets. Note that the barbs 1214 are shown in preformed shape instead of bent shape due to drawing software limitations.

Figure 96:
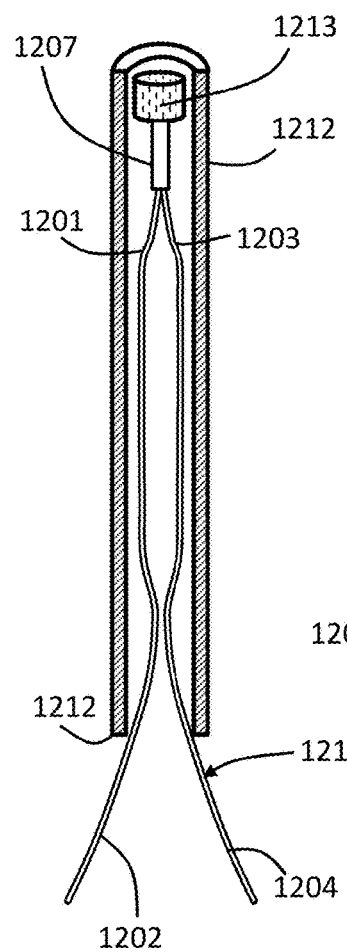
FIGS. 96-98 show a method of deploying the sealing device 1210 from a delivery catheter
Figure 97:
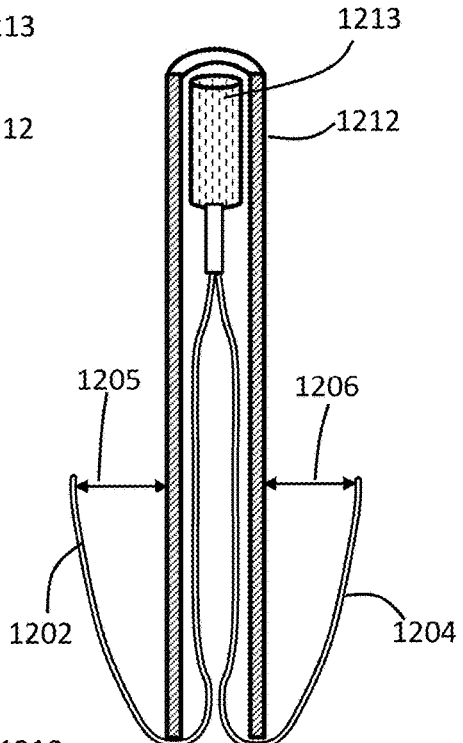
Figure 98:
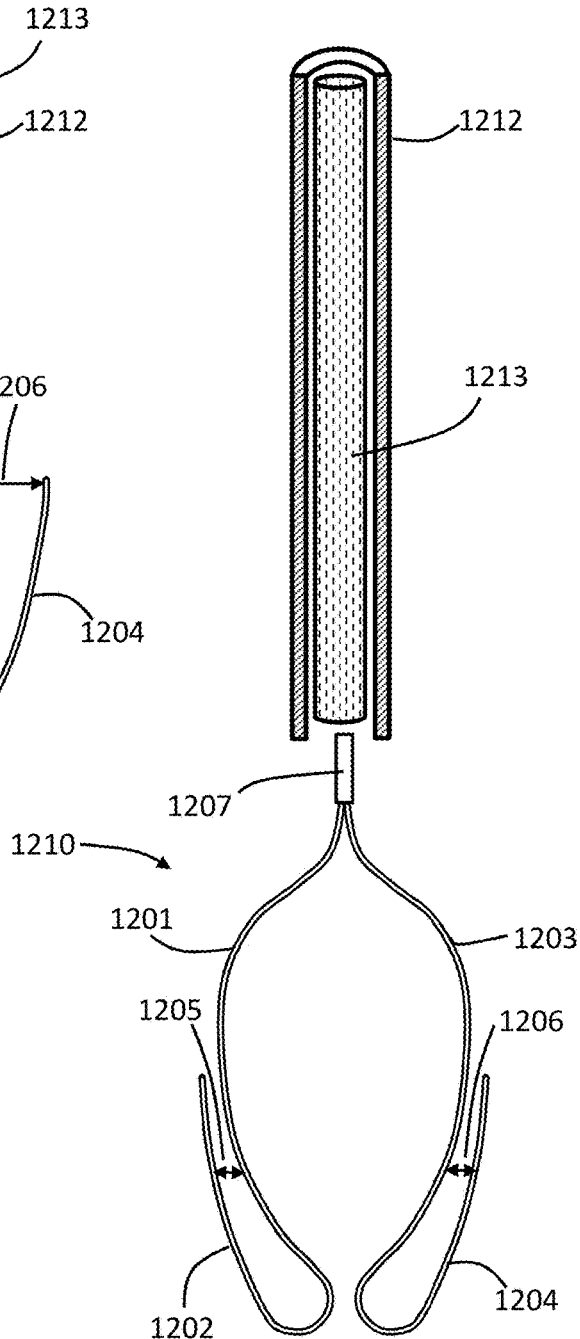

FIGS. 96-98 illustrate an exemplary method of deployment of the device 1210 from a delivery catheter 1212. In FIG. 96, the device 1210 is shown within the catheter 1212 with the anchor leaf springs 1202, 1204 extending distally from the ventricular end of the body leaf springs 1201, 1203 in a straightened or compressed and/or unfurled, state. A pusher member 1213 can be used to push the device 1210 distally relative to the catheter 1212 or to hold the device 1210 steady as the catheter is retracted. In FIG. 97, the catheter 1212 is retracted proximally from the device 1210 and/or the device 1210 is advanced distally from the catheter 1212 such that the elongated anchor leaf springs 1202, 1204 begin to extend out of the distal outlet 1212 of the catheter. As the anchor leaf springs 1202, 1204 move out of the outlet 1212, the anchors begin to naturally return toward the shape of FIG. 94, curling gradually as it is freed from the confining forces of the catheter. Thus, creating gaps 1205, 1206 that can be used to capture leaflets. In FIG. 98, the entire device 1210 has moved out of the catheter 1212 and has returned to its natural shape of FIG. 95. As the device 1210 moves out of the catheter 1212, the body leaf springs 1201, 1203 expand while the anchor leaf spring 1202, 1204 further curl, in attempt to return to the pre-configured device shape as in FIG. 92. This expanding and curling action can be used to grab and position the mitral leaflets within the gaps 1205, 1206. In a preferred embodiment, the gaps 1205, 1206 are configured such that the captured leaflets are securely and atraumatically engaged by the body and anchor leaf springs.

If the user is not satisfied by the position of the captured leaflets in the device, he may disengage the leaflets from the device 1210 and try again. This can be achieved by using methods common to interventional catheters. For example, the device 1210 may be temporally secured to the pusher 1213 (using mechanical locks, sutures or release pins for example). Therefore, by retracting the pusher 1213 inside the catheter, the user can retract the device 1210 back into the catheter which in turn, compresses the body leaf springs 1201, 1203 and uncurls the anchor leaf springs 1202, 1204, thereby, disengaging the leaflets. If the device and leaflet capture are acceptable, the user may completely deploy the device by disengaging the device 1210 from the pusher 1213.

Figure 99:
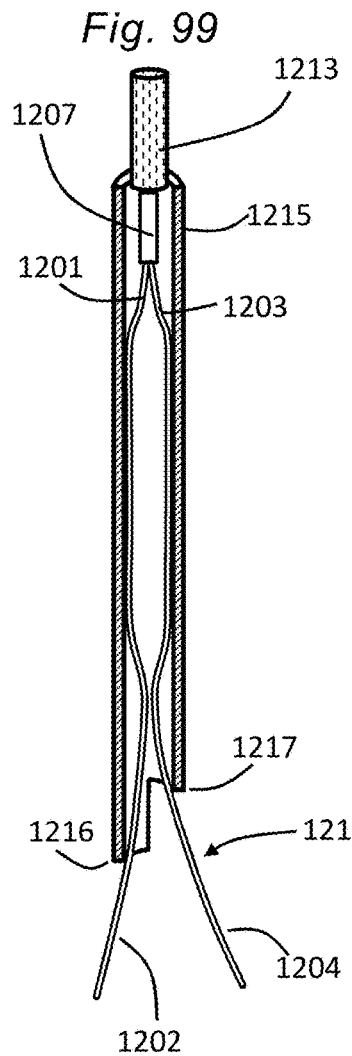
FIGS. 99-103 show a method of deploying the sealing device 1210 from a delivery sheath that allows for sequential grasping of the leaflets.
Figure 100:
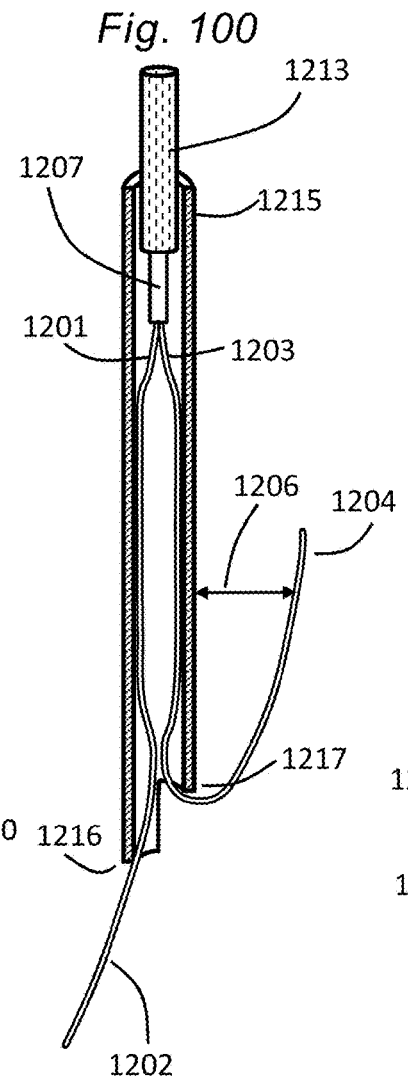
Figure 101:
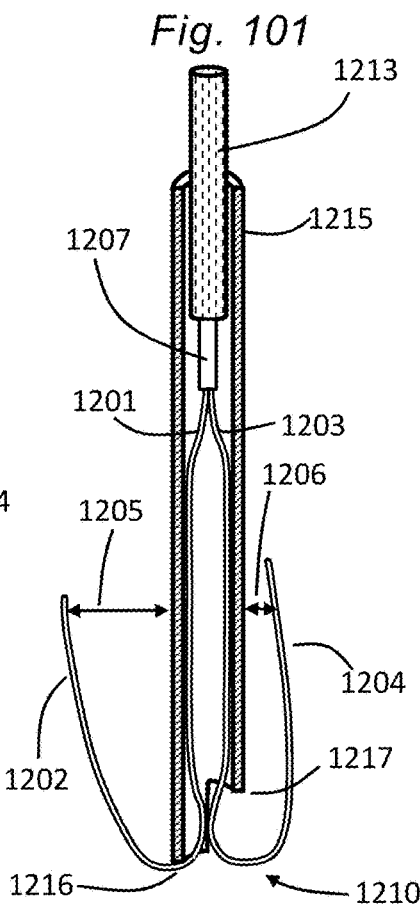
Figure 102:
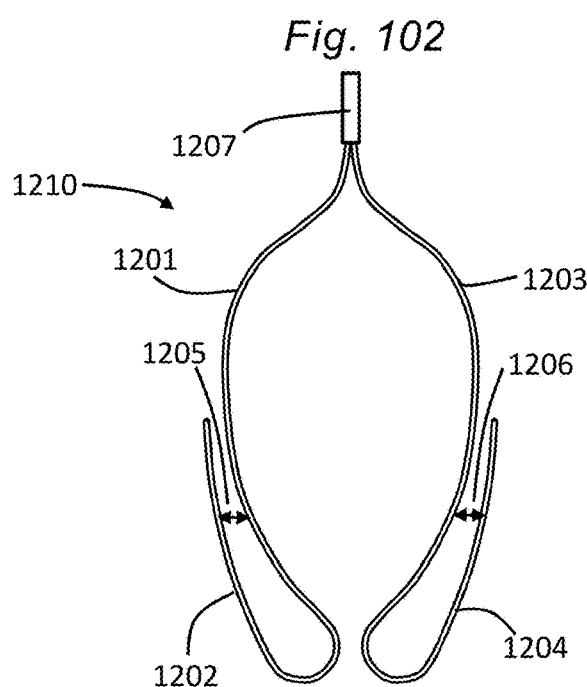
Figure 103:
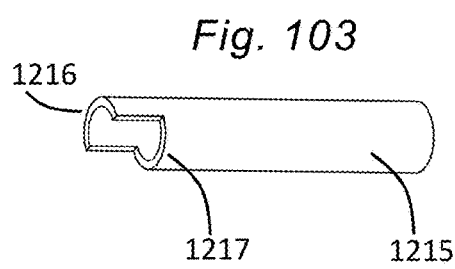
Figure 104:
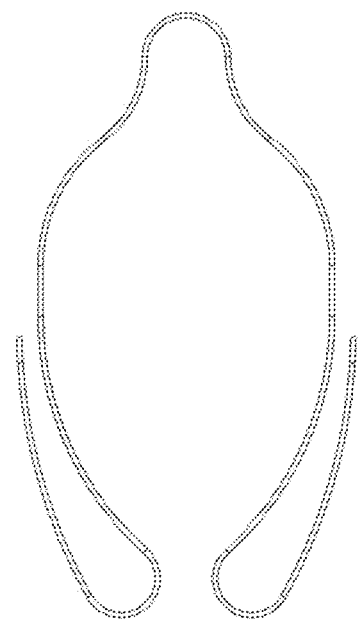
FIG. 104-111 shows a various exemplary embodiment of the leaf-spring based spacers.
Figure 105:
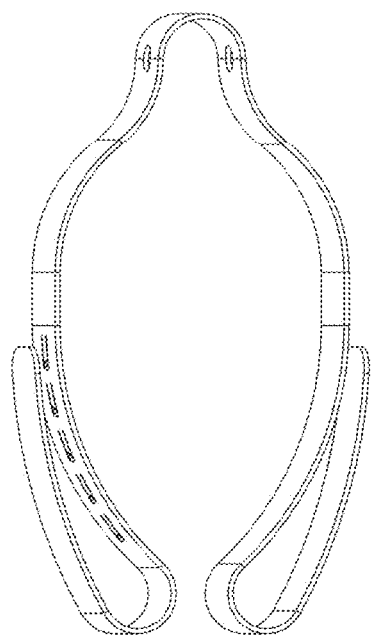
Figure 106:
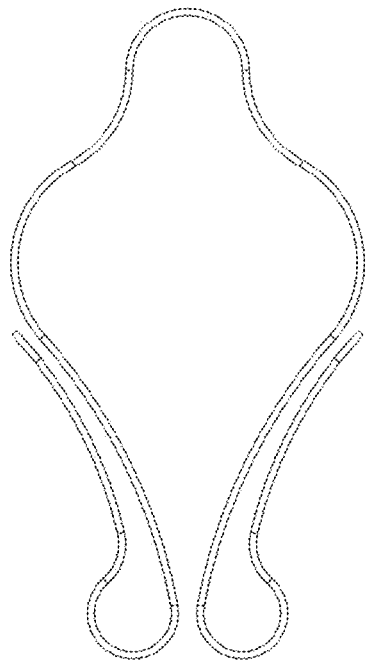
Figure 107:
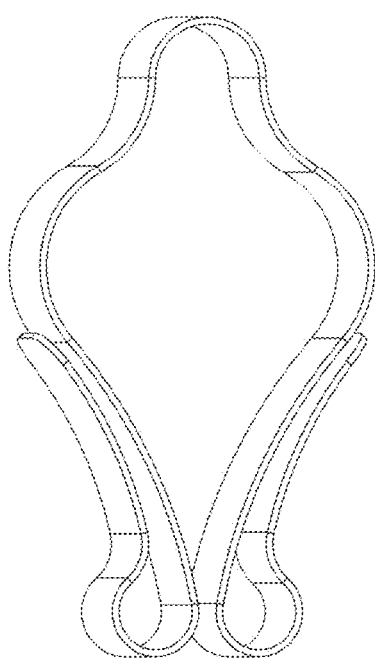
Figure 108:
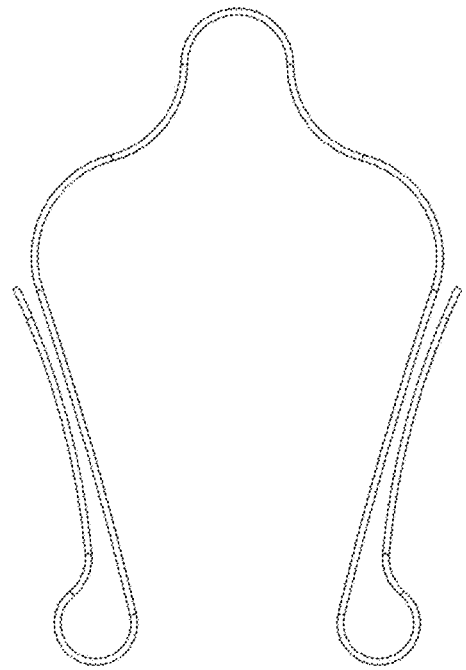
Figure 109:
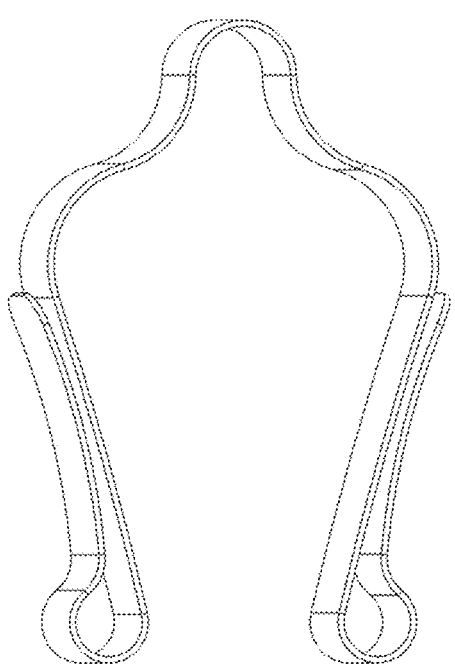
Figure 110:
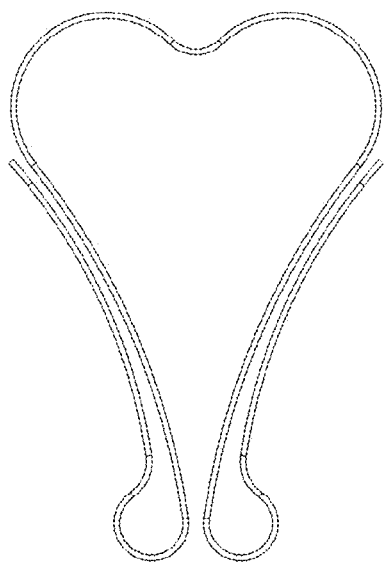
Figure 111:
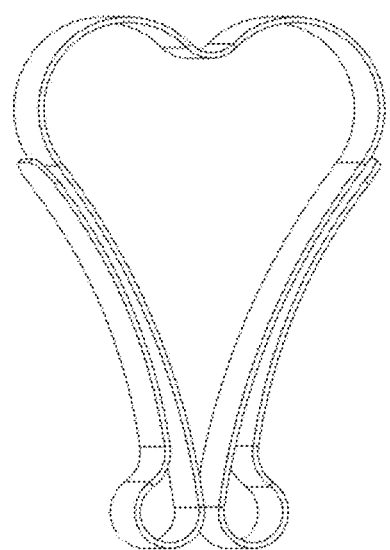

FIGS. 99-103 illustrate an exemplary method of deployment of the device 1210 from a delivery catheter 1215, wherein, the user can sequentially grab and/or constrain one leaflet at a time. This method is slightly modified method as illustrated and described earlier in FIGS. 96-98, wherein, all components except the distal end of the catheter shaft 1215 is stepped that is, there is a leading distal edge 1216 and a trailing edge 1217 as shown in FIG. 103. In FIG. 99, the device 1210 is shown within the catheter 1212 with the anchor leaf springs 1202, 1204 extending distally from the ventricular end of the body leaf springs 1201, 1203 in a straightened or compressed and/or unfurled, state. A pusher member 1213 can be used to push the device 1210 distally relative to the catheter 1215 or to hold the device 1210 steady as the catheter 1215 is retracted. In FIG. 100, the catheter 1215 is retracted proximally from the device 1210 and/or the device 1210 is advanced distally from the catheter such that the elongated anchor leaf spring 1204 first begins to extend out of the distal outlet 1216 of the catheter. This, while the anchor leaf spring 1202 is still constrained in a straightened position by the stepped distal catheter tip 1212. As the anchor leaf springs 1204, moves out of the recessed outlet 1217, the anchor leaf spring begins to naturally return toward the shape of FIG. 102, curling gradually as it is freed from the confining forces of the catheter. Thus, creating gap 1206 that can be used to capture a single leaflet. In FIG. 101, the user then retracts and/or pushes the device 1210 further out to the catheter 1215 such that the $2^{nd}$ anchor leaf-spring 1202 too elastically rebounds to allow the user to now grab and/or constrain the $2^{nd}$ leaflet. Once both leaflets are grabbed and/or constrained, the user can then fully deploy the device 1210, while the leaflets are constrained within the spaces 1205 and 1206 of the device.

FIGS. 104-111 show various exemplary shapes of the leaf spring based spacer embodiments. Further, these embodiments are built using a single contiguous sheet metal. However, these shapes may be achieved using more than one structural segments such as sheet metals, strips, wires, braids, tubes, and other stent like structures.

Figure 112:
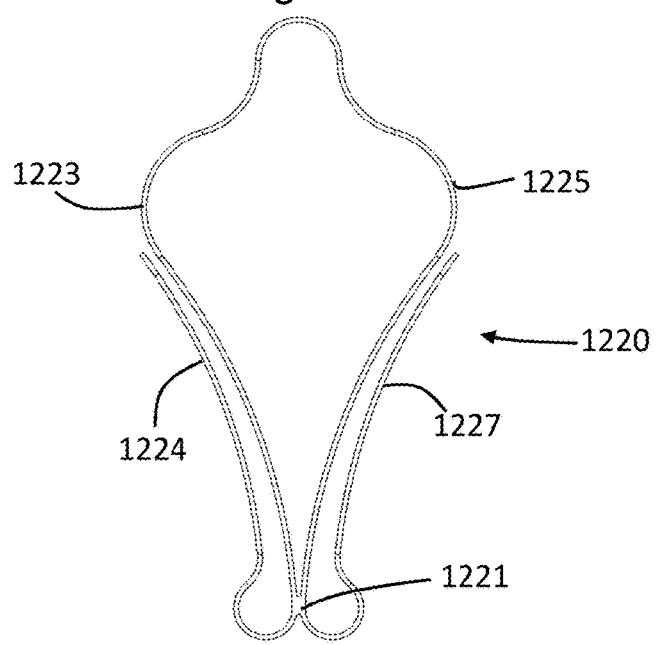
FIGS. 112-113 show a closed cell exemplary embodiment of a leaf-spring based spacer.
Figure 113:
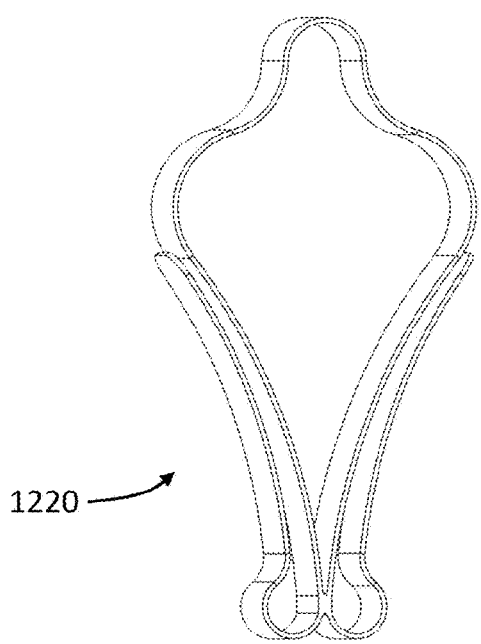

FIG. 112 shows an example of a closed cell body of the leaf spring spacer 1220. This is achieved by joining the body anchor leaf springs 1223 and 1225 at bottom 1221 too. A closed cell body offers higher structural strength in comparison to open cell structure. FIG. 113 shows 3D view of the embodiment shown in FIG. 111.

Figure 114:
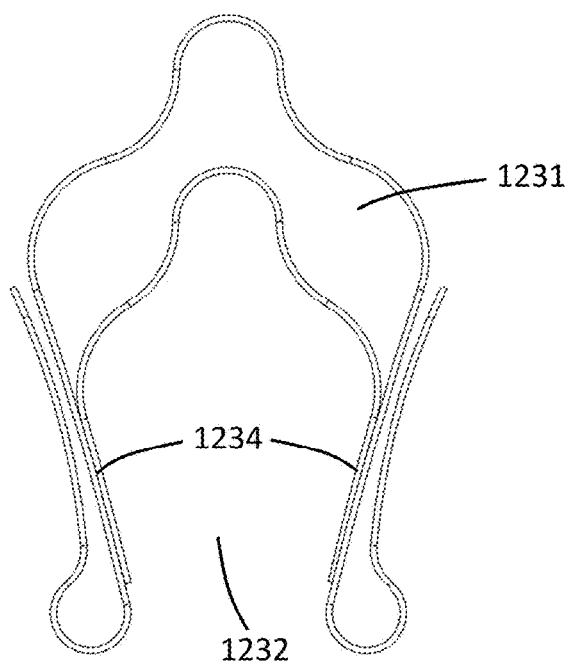
FIGS. 114-115 show a in plane nested exemplary embodiment of a leaf-spring based spacer.
Figure 115:
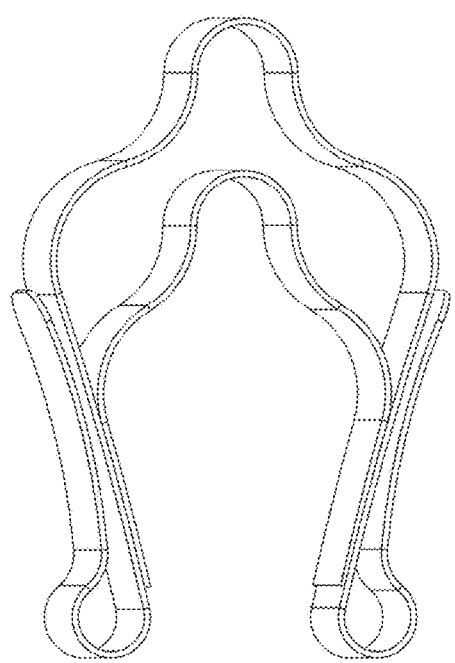

FIG. 114 shows an example of in-plane nested embodiment. In this specific example, the leaf springs are bonded or fastened and/or welded along the location 1234. Thereby, combines the benefits of a closed 1231 and open 1232 cell leaf spring spacer. FIG. 115 shows 3D view of the exemplary embodiment shown in FIG. 114.

Figure 116:
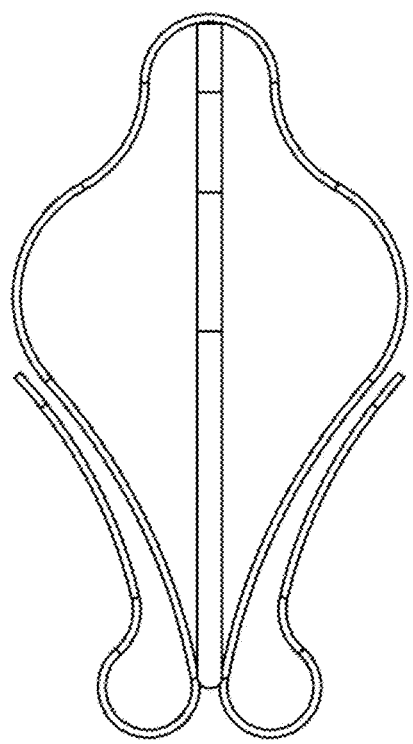
FIGS. 116-118 show an orthogonal plane nested exemplary embodiment of a leaf-spring based spacer.
Figure 117:
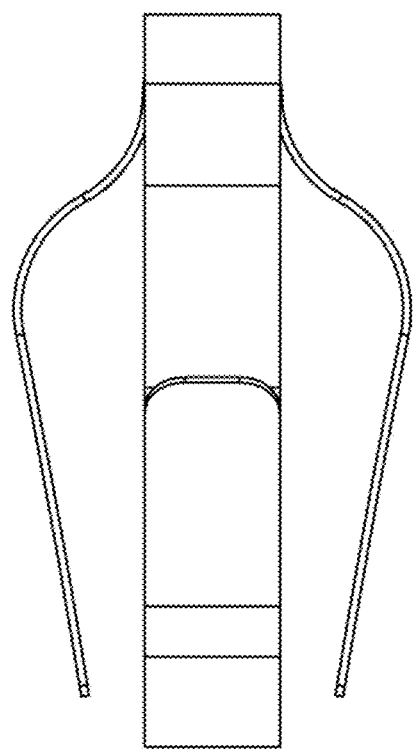
Figure 118:
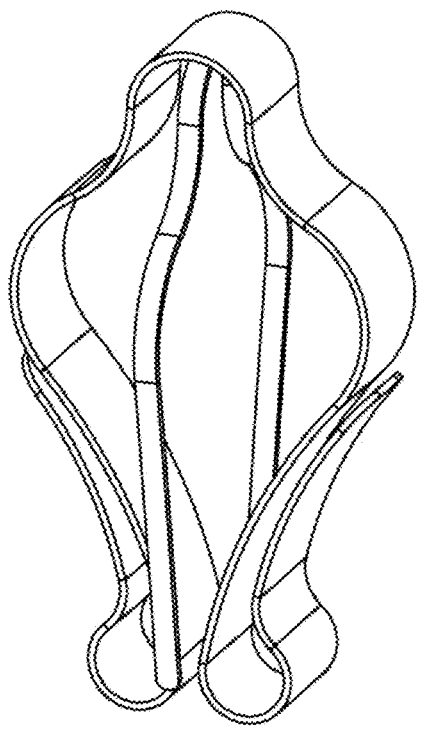
Figure 119:
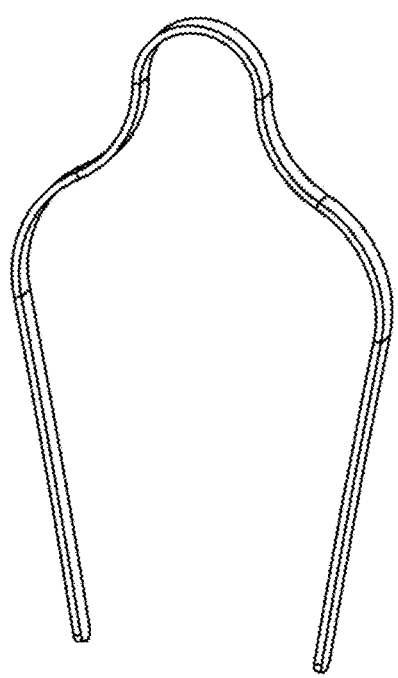
FIG. 119 shows an exemplary orthogonal insert of the embodiment shown in FIGS. 116-118.

FIGS. 116-118 show front, side and 3D view of an exemplary out-of-plane nested embodiment. FIG. 119 shows 3D view of the exemplary insert shown in FIG. 118.

Figure 120:
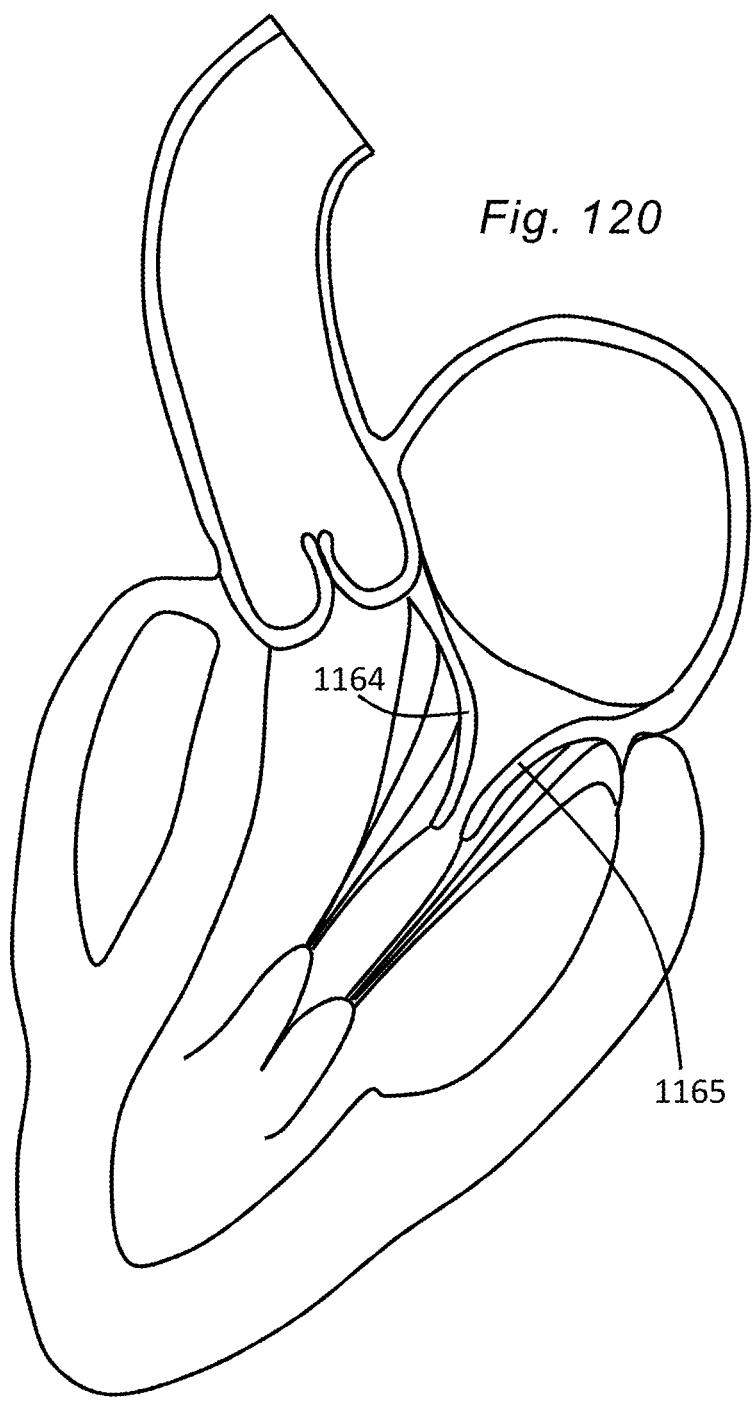
FIG. 120 shows schematic cross-section of a portion of a human heart.
Figure 121:
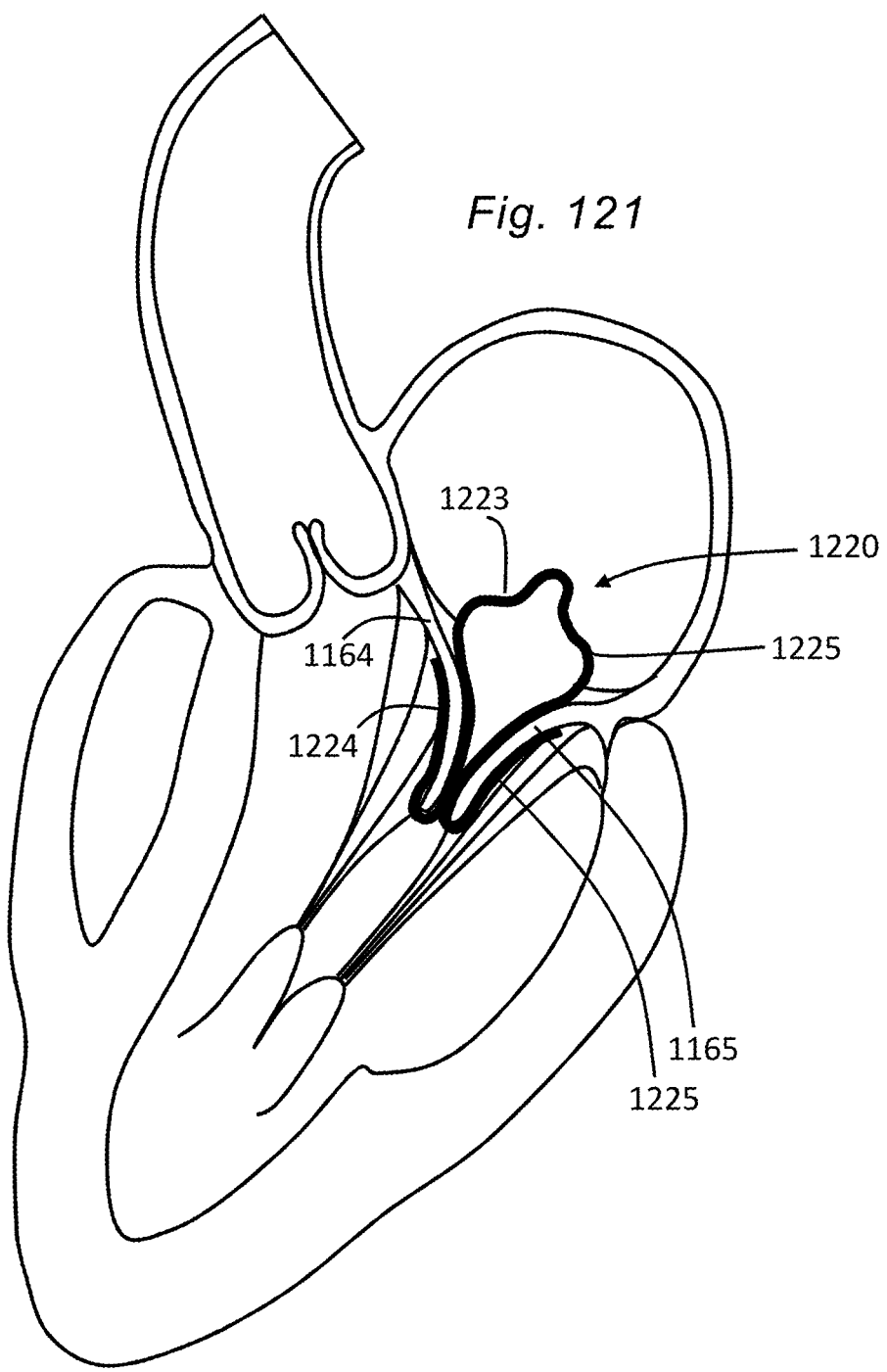
FIG. 121 shows the exemplary embodiment 1220 implanted in a desired configuration in the mitral valve.

FIG. 120 shows a schematic cross-section of the heart. FIG. 121 shows the exemplary embodiment 1220 implanted in a desired configuration in the mitral valve.

Any combination of in-plane and out-of-plane nested leaf spring based spacers may be used. This, in combination with or without blood impervious coverings or barriers may be used to configure an embodiment to address valve regurgitation. Additionally, a plurality of atrial and/or ventricular support structures of various shapes and designs such as 1209 may be used.

Spacer Sheet

Figure 122:
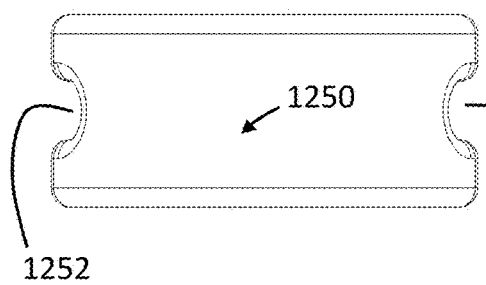
FIG. 122 shows an embodiment of a crescent shaped spacer body 1250 from the convex side.
Figure 123:
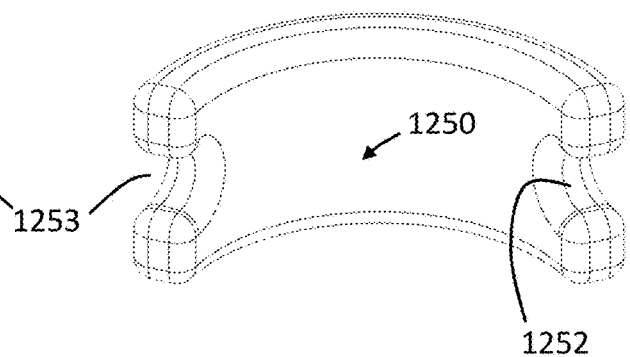
FIG. 123 shows the exemplary embodiment of a sealing device 1250 embodiment from the concave side.
Figure 124:
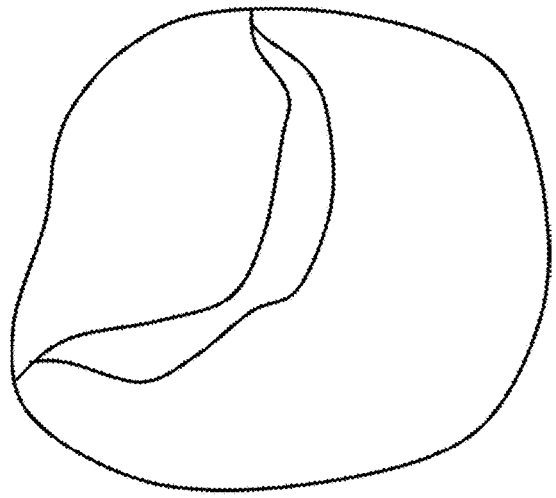
FIG. 124 shows a portion of a human heart mitral valve from top.
Figure 125:
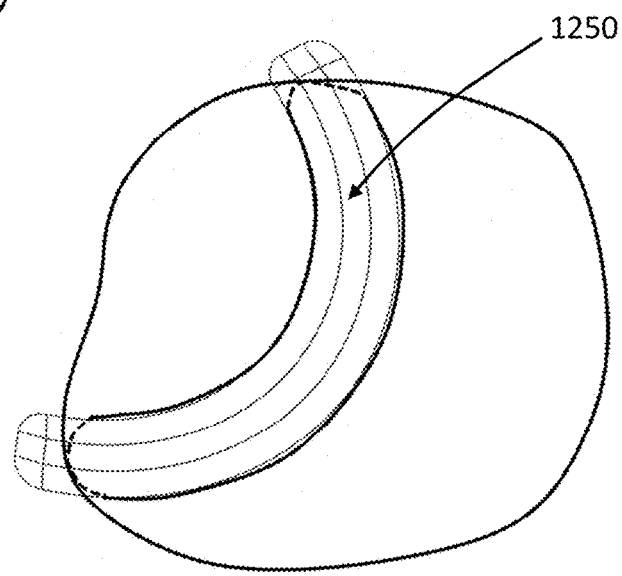
FIG. 125 shows a portion of a human heart mitral valve with an exemplary embodiment of a sealing device 1250 shown previously in FIG. 122 attached to the native annulus and/or mitral leaflet and having an atrial anchor.

FIGS. 122 and 123 show a crescent shaped spacer embodiment 1250 with a notch 1252, 1253 on either sides. FIG. 124 shows a schematic of top view of a mitral valve cross-section and FIG. 125 shows schematic of the device 1250 seated inside the mitral valve. Note that the device 1250 can be any combination of flexible, elastic, rigid, solid, hollow and/or compressible. For example, in one embodiment the device 1250 can be straightened along the length and compressed along the height to allow for smaller diameter catheters.

Further, the device 1250 may be paired with atrial anchors or support members as shown in FIGS. 126-131 as an exemplary. Note that while only atrial anchors or support members are shown in FIGS. 126-131, a variation or combination of these anchors or support members may be used in atrial side, ventricular side and/or annulus.

Figure 126:
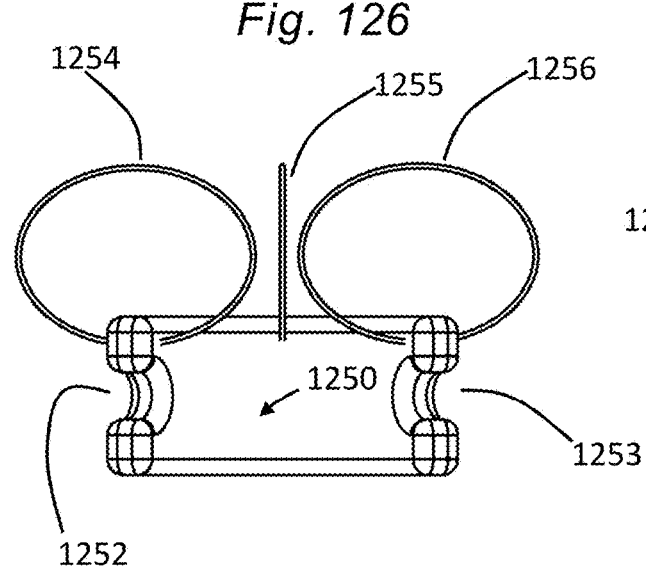
FIG. 126 shows an exemplary embodiment of a sealing device 1250 with looped atrial side anchors and/or support members 1254-1256 from concave side.
Figure 127:
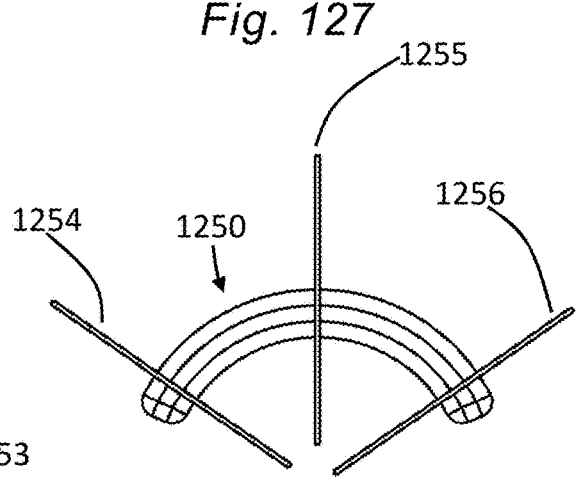
FIG. 127 shows an exemplary embodiment of a sealing device 1250 with looped atrial side anchors and/or support members 1254-1256 from the top/atrial view.
Figure 128:
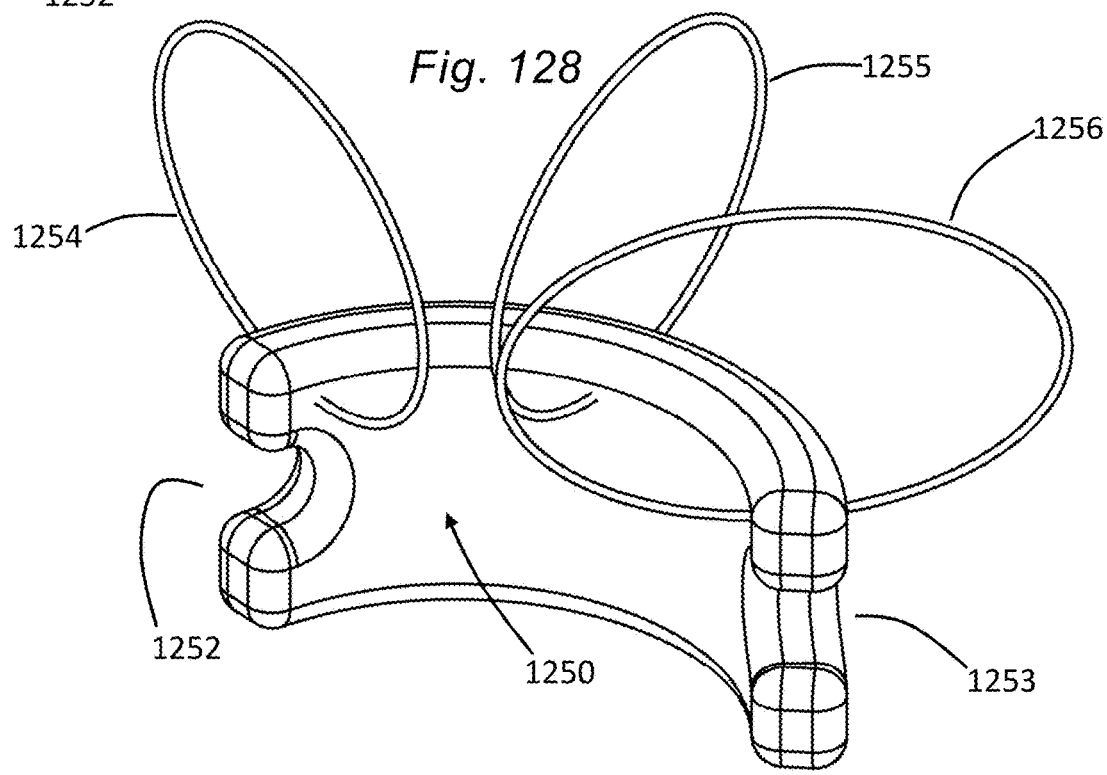
FIG. 128 shows isometric view an exemplary embodiment of a sealing device 1250 with looped atrial side anchors and/or support members 1254-1256.
Figure 129:
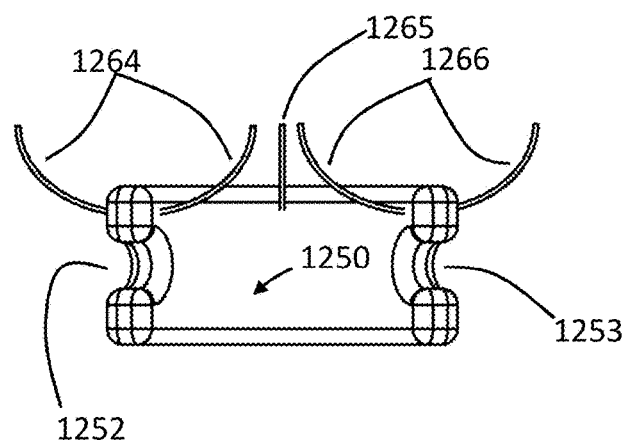
FIG. 129 shows an exemplary embodiment of a sealing device 1250 with free ended atrial side anchors and/or support members 1264-1266 from concave side.
Figure 130:
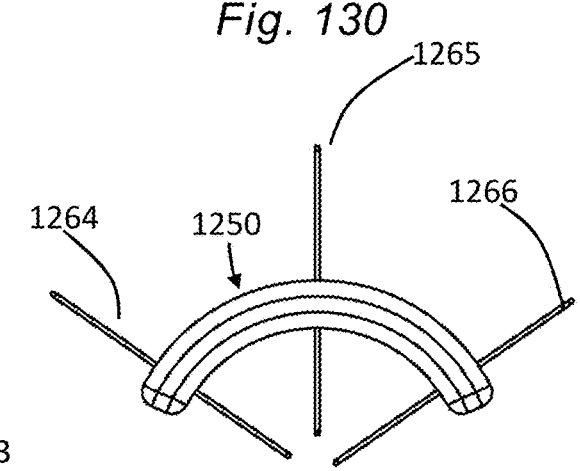
FIG. 130 shows an exemplary embodiment of a sealing device 1250 with free ended atrial side anchors and/or support members 1264-1266 from the top/atrial view.
Figure 131:
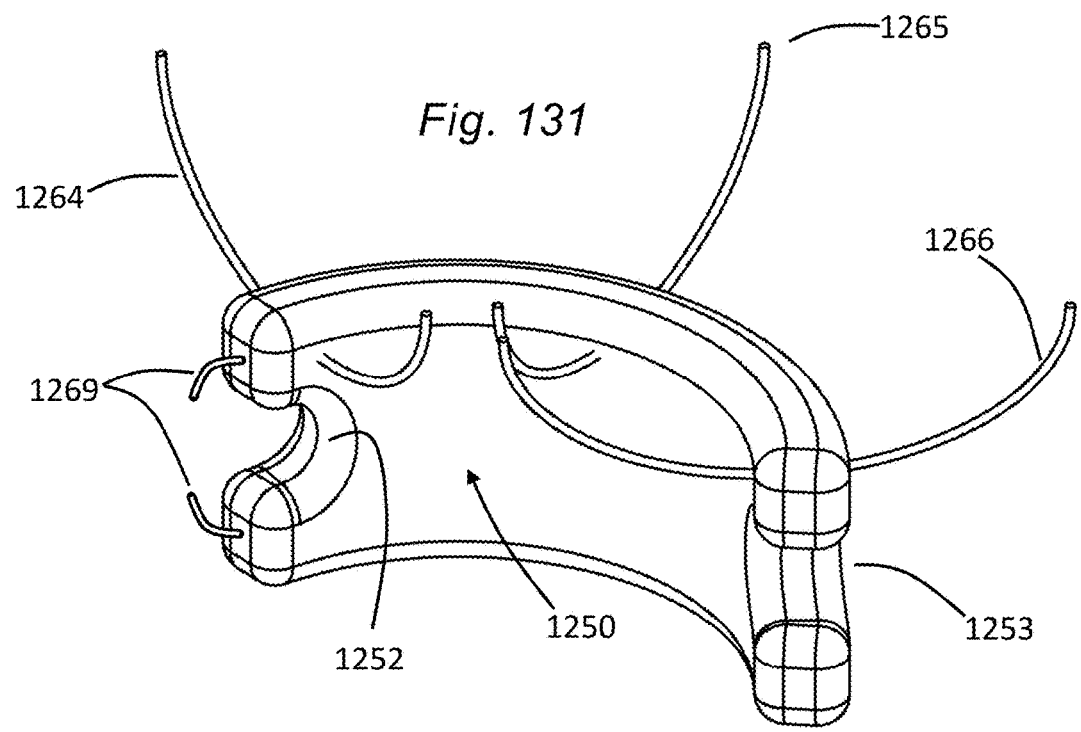
FIG. 131 shows isometric view an exemplary embodiment of a sealing device 1250 with free ended atrial side anchors and/or support members 1264-1266.

FIGS. 126 to 128 show looped anchors or support members on the atrial side. These can be made of metal, polymer, or ceramic. For example, they can be superelastic such as nitinol metal or made of structure polymer such as PEEK. Further, these can be straightened or stretched while loaded in catheter and can reversibly resume their deployed shape as shown in the figures. FIGS. 129 to 131 show anchors or support members on the atrial side that emerge from the body of the device 1250 with a free end as in a cantilever. Additionally, FIG. 131 shows annulus anchors 1269. All of these anchors or support members can be made of metal, polymer, or ceramic. For example, they can be superelastic such as nitinol metal or made of structure polymer such as PEEK. Further, these can be straightened or stretched while loaded in catheter and can reversibly resume their deployed shape as shown in the figures.

FIG. 132 shows an embodiment of spacer that is made of several segments that can be assembled within the cavities of the heart, preferably in the left atrium. The segments may be linked, tied, hinged, wrapped in fabric or any other obvious methods can be used to join in a constrained and yet movable configuration. Each of the segments is loaded into a catheter in stretched/elongated configuration. As the segments are pushed out of the catheter, a string, wire, or suture 1273 is used to pull them together in a configuration of increasing thickness, as can be further seen in 3D schematic of the device in FIG. 133. One way to achieve this is by having a ball like anchor 1276 on the distal most termination of the suture 1273 and a movable anchor 1277. The movable anchor can then be locked in the predetermined configuration and the excess proximal end of the suture can be cut to release and deploy the device 1270 as shown in FIG. 134.

Figure 135:
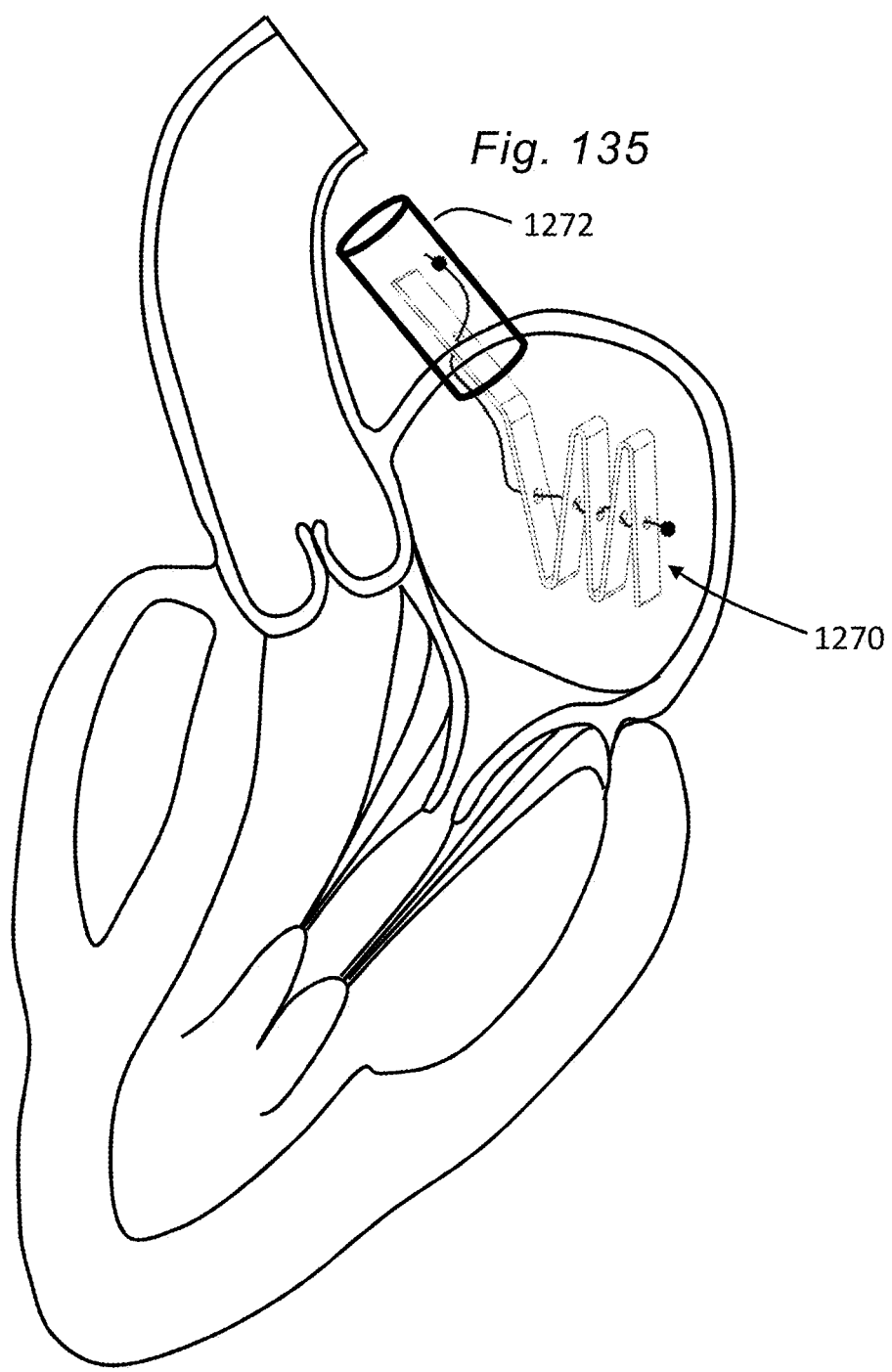
FIG. 135 shows an exemplary trans-septal catheter 1272 and the device 1270 being pushed out in the left atrium.
Figure 136:
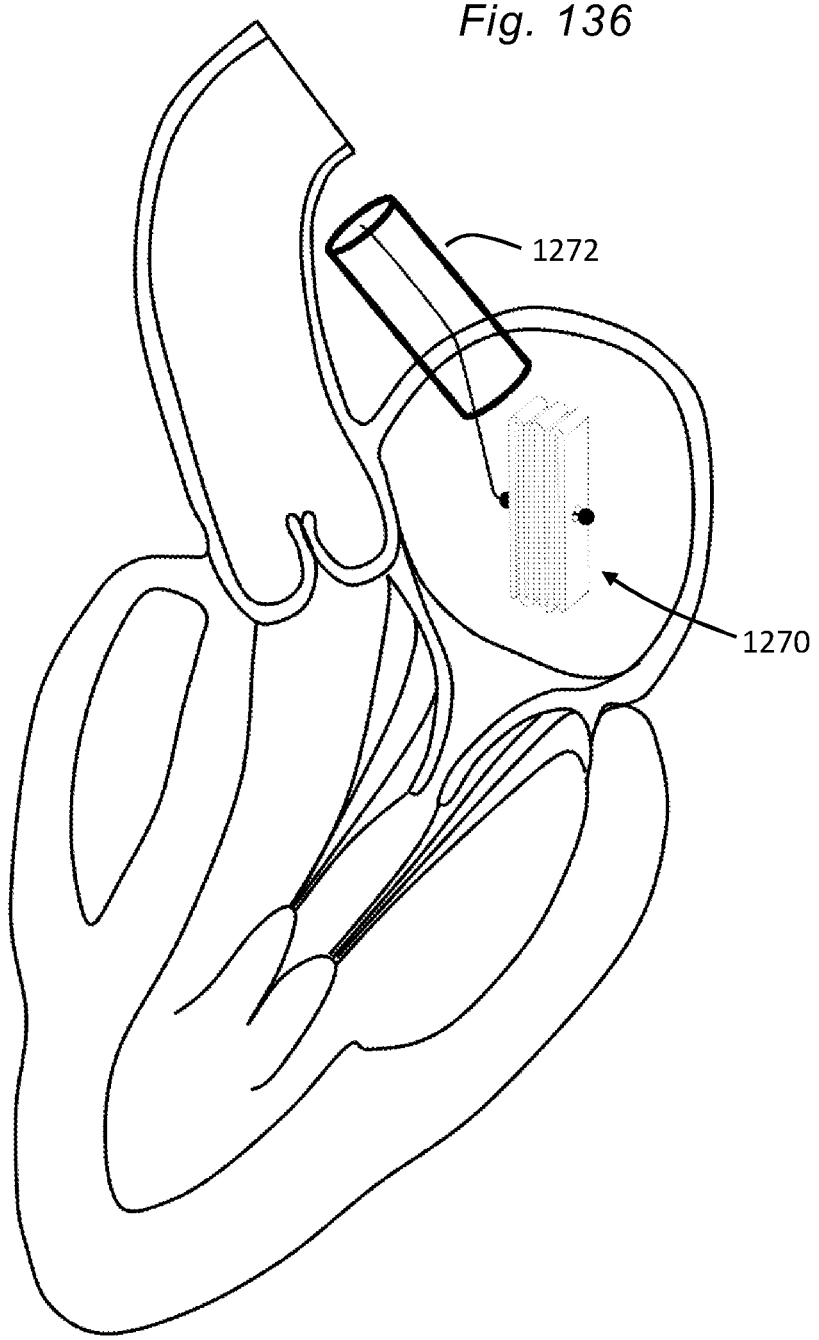
FIG. 136 shows the device outside of the catheter 1272 and cinched in the left atrium prior to being deployed into the mitral valve.
Figure 137:
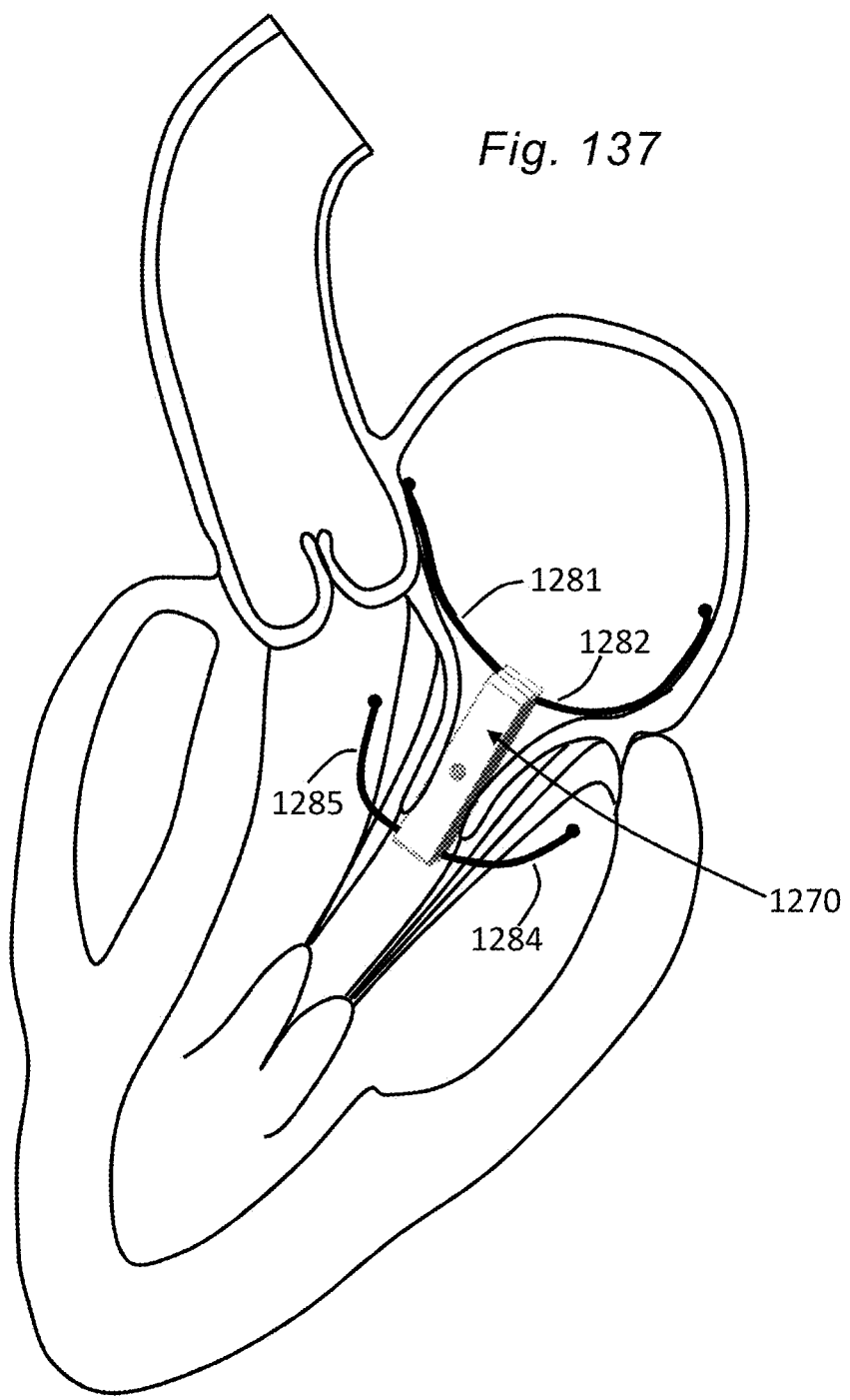
FIG. 137 shows cross-section of the heart and the device 1270 deployed in the mitral valve. Additionally, it shows atrial and ventricular support members or anchors 1281, 1282 and 1284, 1285 respectively.

FIG. 135 shows schematic of device 1270 being deployed in the left atrium via a trans-septal catheter. FIG. 136 shows the next stage where the suture is being used to assemble the device in desired configuration. FIG. 137 shows the final configuration where the device is deployed in the mitral valve. It additionally shows a variation in embodiment with additional atrial anchors 1281 and 1282 as well as ventricular anchors 1284 and 1285, similar to the anchors previously described and shown in FIG. 131.

One other obvious variation of device 1270 can be that all segments can be cut out of a single sheet of superelastic material such as nitinol and shape-set in its final configuration as in FIG. 134. Hence, when straightened and loaded into the delivery catheter, it self assembles in the predetermined shape-set configuration with or without the use of suture 1273, when pushed out of the catheter.

Annulus Reshaping Device

An exemplary method of performing mitral valve annuloplasty on a patient's heart is described. As indicated above, the intravascular annulus reshaping device is preferably loaded and delivered to a desired location using an interventional vascular catheter with the proximal and distal anchors in a delivery or straightened or collapsed condition. The leaf spring of the device is made of an elastic material and preferably of a super elastic material such as nitinol. A user may deploy the distal end of the intra-vascular device from the catheter into the lumen of a coronary sinus by advancing the intravascular device or by retracting the catheter, or a combination thereof. A delivery tool may provide for distal movement of the intravascular device with respect to the catheter, and a tether may provide proximal movement of the device or for maintaining the position of the intravascular device relative to distal motion of a catheter. Because of the inherent recoverability of the nitinol material from which it is formed, leaf spring begins to curve as soon as it is deployed from the catheter. This curving of the leaf spring causes the distal anchor to engage with the tissue.

Next, the intravascular device is tensioned by pulling on the tether to apply a proximally-directed cinching force on the distal anchor, thereby modifying the shape of the coronary sinus and adjacent nearby valve annulus tissue. Fluoroscopy, ultrasound or other imaging technology may be used to detect when the device modifies the shape of the mitral valve annulus sufficiently to reduce mitral valve regurgitation.

Once the device has been satisfactorily cinched, the proximal anchor is deployed from the catheter. In some embodiments, the proximal anchor is deployed in the coronary sinus, but it may be deployed in other vessels as well. Finally, the coupler that couples the intravascular device to a delivery tool can be released, using any method common in percutaneous stent delivery industry. For example, a hitch wire is first withdrawn, thereby releasing the loop so it can be pulled through and thereby uncoupling the intravascular device from the delivery tool.

In some embodiments it may be necessary to move or remove the intravascular device after deployment by recapturing the device into a catheter. This can be done by advancing the catheter over the device so that the entire intravascular device is once again inside the catheter. In some embodiments the tether may be used to pull the intravascular device proximally while holding the catheter stationary. If the coupler has been detached from the device prior to capture, the device may be recaptured into the delivery catheter or another catheter by grasping the proximal end of the device with a tether, hook or grasper and by advancing the catheter distally over the device.

Figure 138:
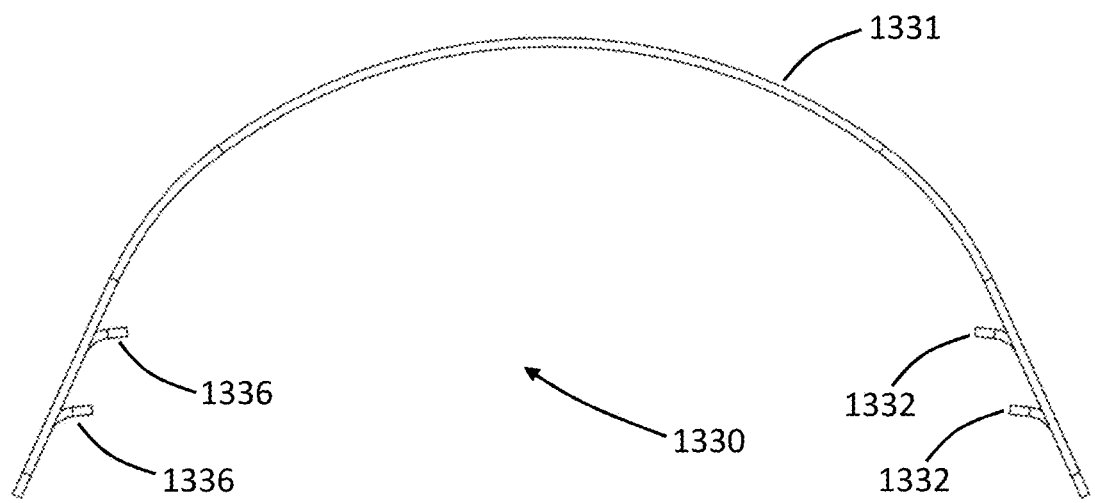
FIG. 138 shows an embodiment of the device 1330.

FIG. 138 shows an embodiment of annulus reshaping device 1330 that is deployed in the coronary sinus. This invention relates to a medical device and uses thereof that supports or changes the shape of tissue near a vessel in which the device is placed. This invention is particularly useful in reducing mitral valve regurgitation by changing the shape of or supporting a mitral valve annulus. U.S. Pat. No. 9,526,616 B2 describes a similar approach to cinch the annulus, however, that device uses wires and relies on expanding against the wall of the artery to secure either ends to generate cinching force. The expansion against the wall of the vessel can be unsafe and unreliable. Too little can lead to slippage and too much can be traumatic and may lead to perforation. Further, the cinching wire can have a cheese cutter effect on the surrounding tissue. This invention 1330 is based on using a wide atraumatic leaf-spring 1331 to cinch the annulus and uses atraumatic frictional members 1332 and 1336 to secure the ends. The wide surface area of the leaf spring mitigates the cheese cutter risk of a wire and the tiny barbs 1332 and 1336 are atraumatic and yet can help secure the device in place with the desired cinching force. Further, owing to the elastic nature of the leaf spring, it can be configured to exert radial compression force on the annulus.

Figure 139:
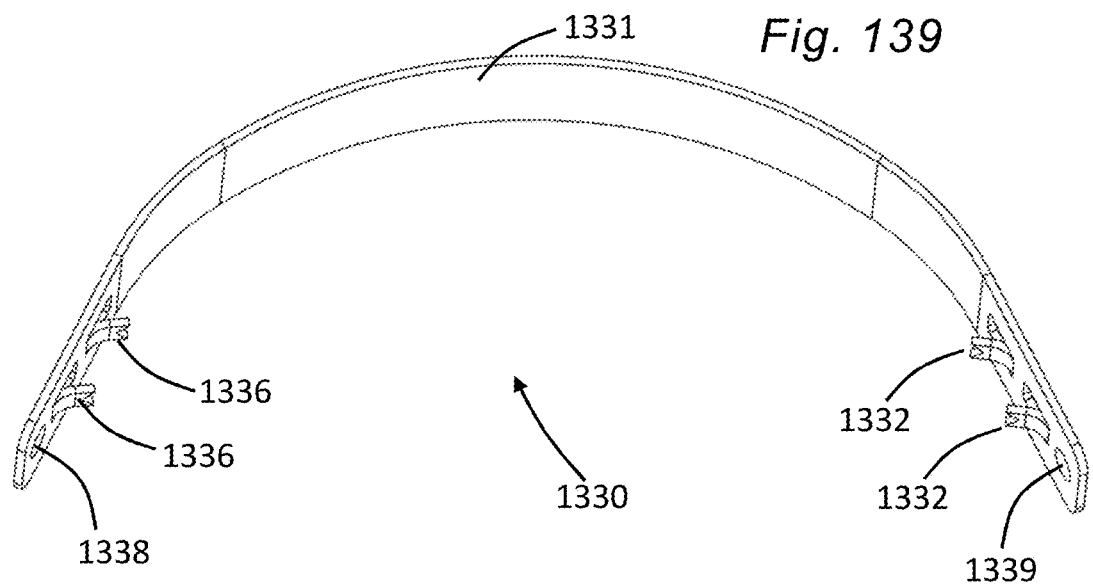
FIG. 139 shows the same device 1330 in a 3D perspective.

FIG. 139 shows the 3D aspect of the embodiment 1330 in FIG. 138.

Figure 140:
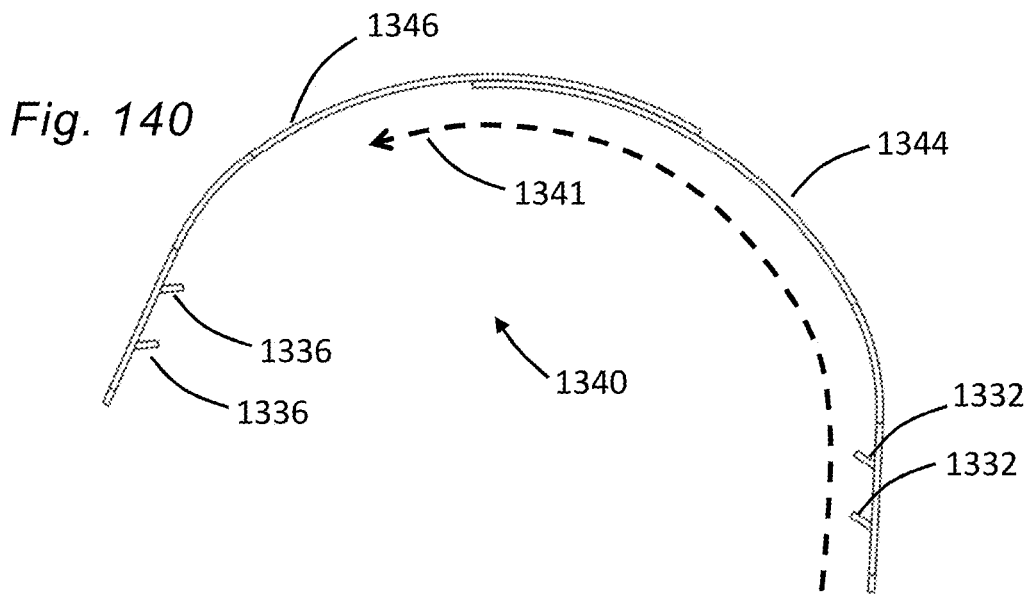
FIG. 140 shows a device 1340 with telescoping leaf spring.
Figure 141:
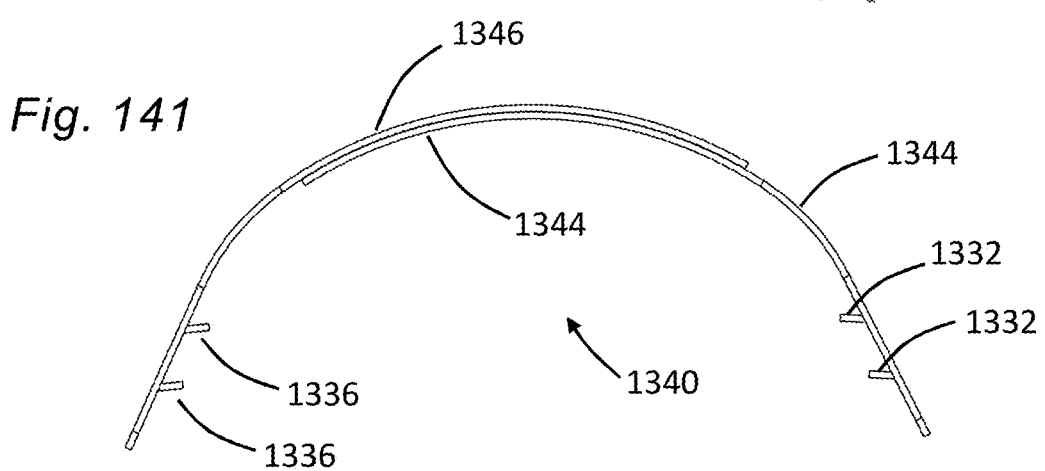
FIG. 141 shows the device 1340 in FIG. 138 in a locked configuration.

FIGS. 140 and 141 show an alternate embodiment of annulus reshaping device 1340 that provides enhanced cinching and radial compression by using telescoping leaf-springs 1344 and 1346. As can be seen in the FIGS. 140 and 141, 1344 and 1346 can translate and be lock in final cinched position as FIG. 141. Further, the overlapping of leaf-springs 1344 and 1346 can provide increased radial compression or force in comparison to a single leaf-spring device such as in FIG. 138.

Figure 142:
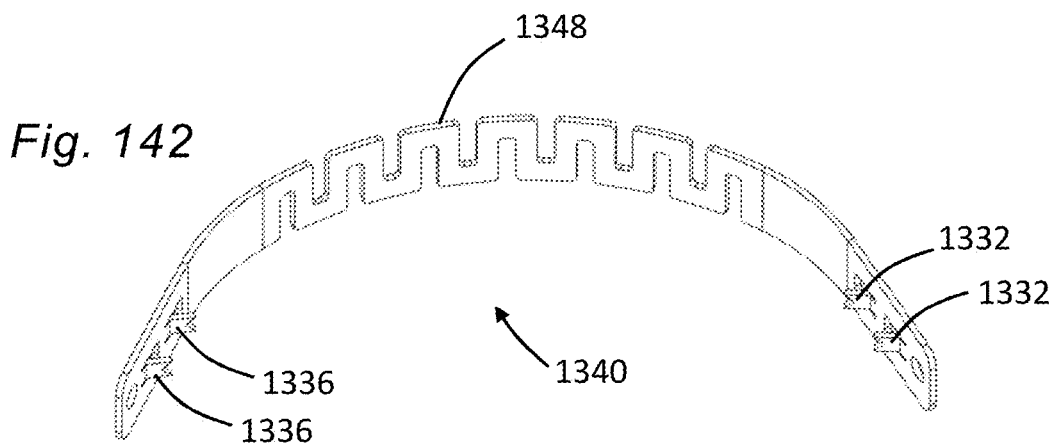
FIG. 142 shows the device 1340 with an expandable leaf spring.

FIG. 142 shows yet another variation of annulus reshaping device that allows for improved cinching by elastic expansion and compression of the leaf spring 1348. While 1348 shows one example of stretchable leaf spring pattern, other obvious patterns or combinations of patterns routinely used in the stent and medical device industry may be used.

Figure 143:
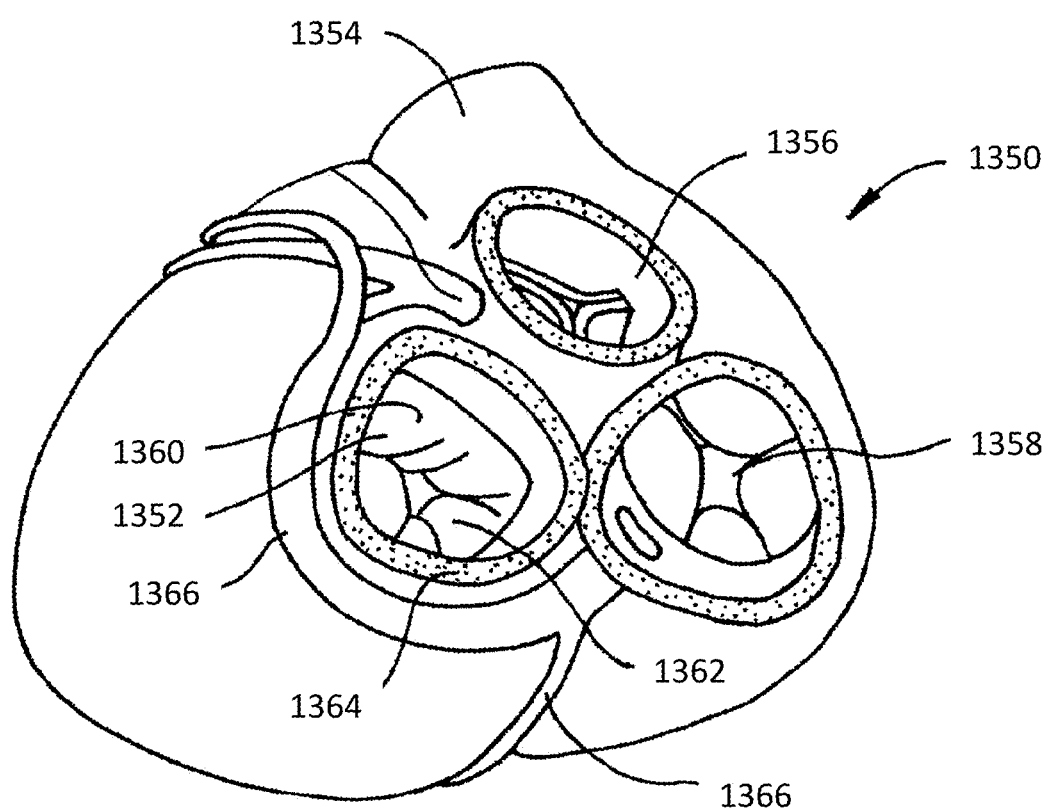
FIG. 143 is a superior view of a heart with the atria removed.

FIG. 143 is a superior view of a heart 1350 with the atria removed. As pictured, the heart comprises several valves including mitral valve 1352, pulmonary valve 1354, aortic valve 1356 and tricuspid valve 1358. Mitral valve 1352 includes anterior cusp 1360, posterior cusp 1362 and annulus 1364. Annulus 1364 encircles cusps 1360 and 1362 and functions to maintain their respective spacing to ensure complete mitral valve closure during left ventricular contractions of the heart 1350. As illustrated, coronary sinus 1366 partially encircles mitral valve 1352 and is adjacent to mitral valve annulus 1364. Coronary sinus 1366 is part of the venous system of heart 1350 and extends along the AV groove between the left atrium and the left ventricle. This places coronary sinus 1366 essentially within the same plane as mitral valve annulus 1364, making coronary sinus 1366 available for placement of shaping device 1330 in order to reshape mitral valve geometry and to restore proper valve function.

Figure 144:
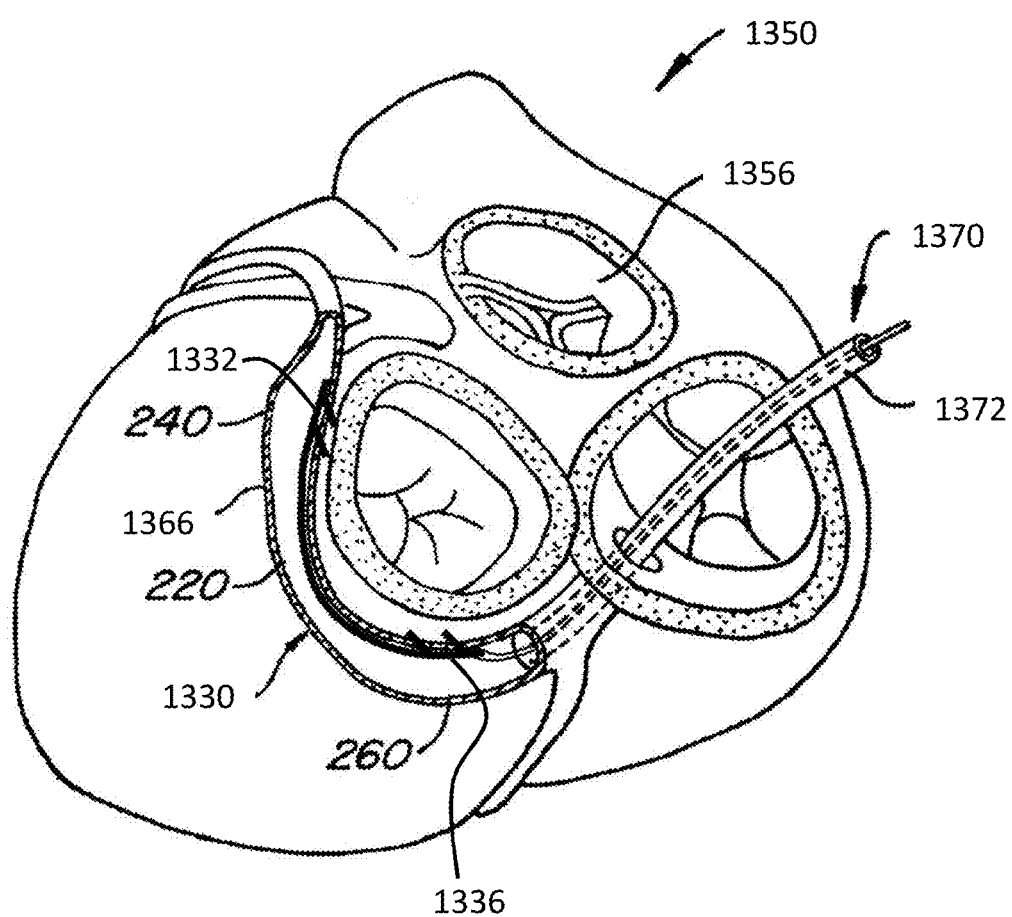
FIG. 144 illustrates delivery of intravascular device 1330 to a coronary sinus.

FIG. 144 illustrates one possible embodiment of an intravascular tissue shaping device 1330 which is deployable in coronary sinus 1366. As illustrated in FIGS. 138 and 139, the device 1330 comprises of a leaf-spring 1331 with a distal anchor/barbs 1332 and a proximal anchor/barbs 1336. Both distal anchor 1332 and proximal anchor 1336 are shown in their deployed configurations, securely positioned within the coronary sinus 1366. FIG. 144 further depicts, in phantom, a delivery tool 1370 comprising catheter 1372 for delivering and positioning intravascular device 1330 in the coronary sinus 1366.

Figure 145:
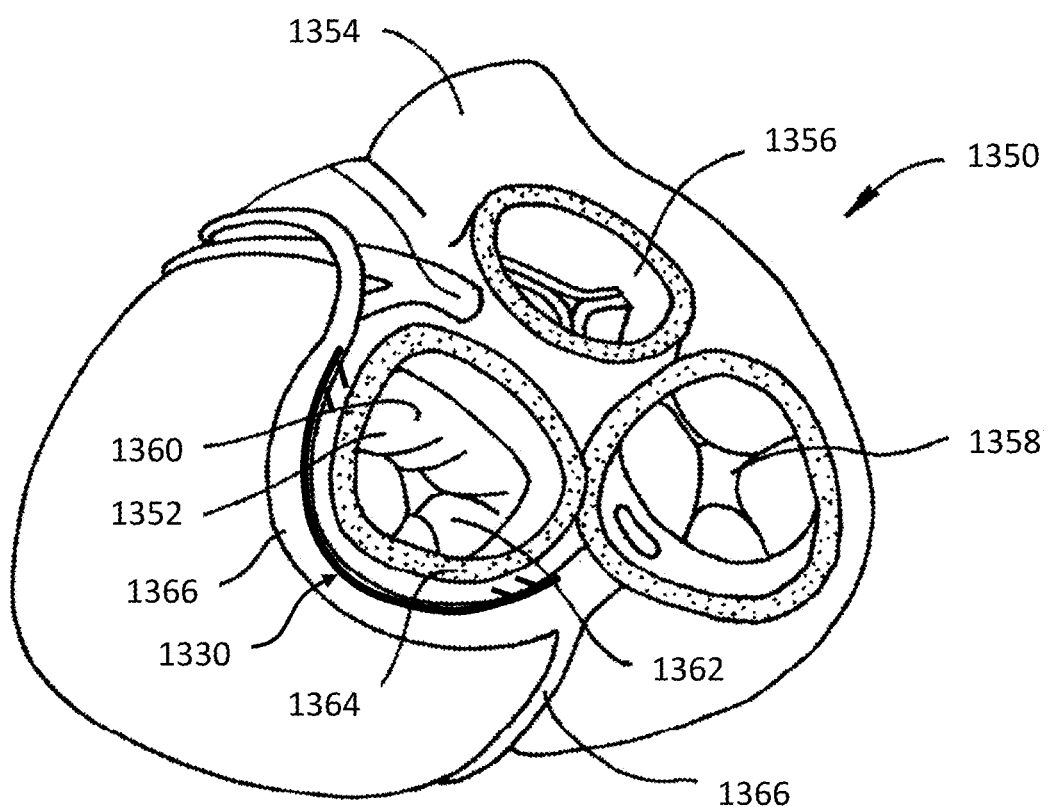
FIG. 145 illustrates deployment of intravascular device 1330 in a coronary sinus.

FIG. 145 shows an example of the device 1330 in its delivered configuration in the coronary sinus 1366.

Figure 146:
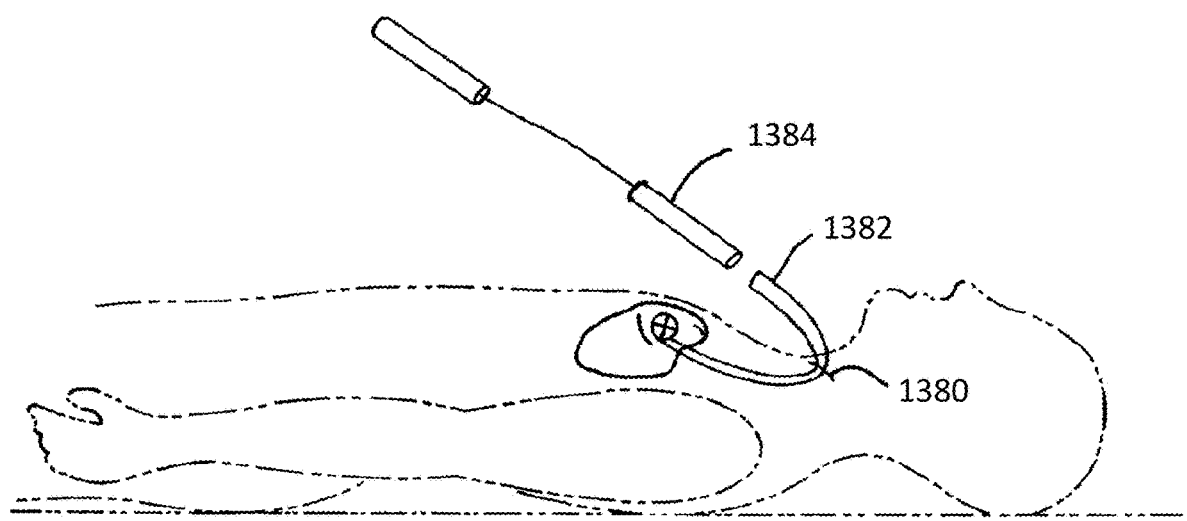
FIG. 146 illustrates delivery of an intravascular device to a target location within a patient's body.

FIG. 146 illustrates one embodiment of delivering the intravascular device of the present invention to a desired location within a patient's body. An incision 1380 is made in the patient's skin to gain access to a blood vessel. The blood vessel may be, for example, the jugular vein. A guide catheter 1382 is advanced through the patient's vasculature until its distal end is positioned near the desired location for the intravascular device. After positioning the guide catheter 1382, a delivery catheter similar to a typical coaxial stent delivery catheter and advancing mechanism 1384 are inserted through the guide catheter 1382 to deploy the intravascular device at the desired location in the patient's body. In preferred embodiments, the delivery catheter is advanced until its distal end is inside the coronary sinus.

Catheter Section

In any of the four approaches described in FIGS. 39-42, a marker catheter or other similar device can be used to help coordinate delivery and ensure that a desirable delivery position is achieved. An exemplary suitable marker catheter can include a standard catheter designed for angiograms, for example, a catheter made of a relatively low-density plastic material having relatively high-density metal marker bands (e.g., radiopaque marker bands) disposed at regular intervals thereon. Thus, the device can be introduced into a patient's vasculature and can be viewed under echocardiography or fluoroscopy. Alternatively, a marker wire can be used in place of the marker catheter. Another suitable alternative technique is left atrium angiography, which can help a physician visualize components of a patient's heart.

A marker catheter or marker wire can be introduced into a patient's vasculature and advanced to specific areas of the vasculature near a patient's heart. For example, a marker catheter can be advanced from a patient's jugular or femoral vein into the right atrium, then into the patient's coronary sinus. As another example, a marker catheter can be advanced from a patient's femoral artery to the patient's circumflex artery. As another example, a marker catheter can be advanced into a patient's left atrium. Once situated in the coronary sinus, circumflex artery, left atrium, or other suitable area of a patient's vasculature, the marker catheter can be used to aid a physician in delivering and ensuring desirable implantation of a prosthetic device. For example, the coronary sinus extends around the heart near the location and elevation of the mitral valve and thus can help a physician to properly size and position a prosthetic device for implantation.

For example, the patient's vasculature can be viewed under echocardiography, fluoroscopy, or other visualization technique which allows a physician to view the prosthetic device being delivered and the marker catheter. A physician can first view the devices along an axis extending from the patient's left atrium to the patient's left ventricle (referred to as a "short axis"). By viewing the devices along the short axis, a physician can deploy an implantable prosthetic device to desired sizes and/or configurations based on the size and location of the marker catheter, which can provide an estimate of the size of features of the native mitral valve. Alternatively or additionally, a physician can use the marker catheter to obtain an estimate of the size of a patient's native heart valve, from which estimate a prosthetic device to be implanted in the patient's native heart valve can be selected from a set of devices having differing sizes, e.g., a set of devices having differing diameters.

A physician can also view the devices along an axis perpendicular to the short axis (referred to as a "long axis"). The long axis can have several orientations, such as from commissure to commissure, but in one specific embodiment, the long axis is oriented from the A2 location to the P2 location of the native mitral valve. By viewing the devices along the long axis, a physician can align an implantable prosthetic device relative to the marker catheter at a desirable location along the short axis, such that an atrial anchor of the implantable device is situated in the left atrium (above the marker catheter) and a ventricular anchor of the implantable device is situated in the left ventricle (below the marker catheter).

The multi-anchor spacers described herein offer several advantages over previous techniques for treating regurgitation in heart valves. For example, the multi-anchor spacers described herein can be used to treat patients whose native leaflets fail to coapt at all, whereas many previous techniques required some amount of native coaptation to be efficacious. Additionally, the spacers described herein (e.g., spacer 640) can treat eccentric jet regurgitation more readily than other known techniques. While embodiments have been illustrated with two and three anchors, the techniques described herein are generally application to spacers having any number of anchors.

FIG. 51 shows an example of embodiment where the annulus straddling anchors 1030 and 1031 as described earlier in FIG. 47 originate from the cluster of other atrial anchors such as 1001 and 1002. Further, there are no anchors originating from the ventricular side of the body 1009.

FIGS. 52 to 54 show examples of various embodiments wherein, the annulus straddling anchors 1030 and 1031 are configured in various shapes to position and locate the device 1000 appropriately within the mitral valve (1032 shows intended position of the annulus along the length of the body 1009.

FIG. 55 shows a version of embodiment with atrial anchors similar to those in FIGS. 44 to 47 and 51 to 54. However, the annulus straddling anchors 1037 and 1038 originate and end in the body 1009 to form a closed loop.

FIG. 56 shows an example of embodiment described in FIG. 48 in mitral valve of a heart.

FIGS. 74 and 75 show an exemplary leaf spring device 1130.

FIG. 76 shows the laser cut flat pattern of exemplary leaf spring device 1130.

FIG. 77 shows an example of device embodiment 1140 that is made of two leaf springs devices 1130 joined using a structural rectangular tube fixed with any suitable and well known techniques such as crimp, weld, or with fasteners. These leaf springs can be made of laser cut sheet metal or strip (flat wire). Each sheet metal component as has an atrial side 1141 (or 1143) and a ventricular side 1142 (or 1144). The Atrial (and/or ventricle) side may have barbs 1146 (or frictional elements) to hold on to the leaf lets in the spaces 1147 and 1148.

FIG. 78 shows 3D aspect of device 1140 shown in FIG. 77. (Note, the laser cut barbs are shown in preformed shape due to CAD software limitations).

FIG. 79 shows device embodiment 1140 loaded into a catheter 1150 in a stretched configuration and partially deployed (using a pusher 1151) to let the ventricle side 1142 and 1144 of the device out of the catheter. Note that in this configuration, the ventricle side of the device arms are still relatively straight.

FIG. 80 shows a later configuration wherein the pusher 1151 further pushes the device 1140 out of the catheter 1150, such that the ventricle side of the arms are able to revert back elastically to the original shape. This create gaps 1153 and 1154 which can then be maneuvered to capture mitral valve leaflets.

FIG. 81 shows the fully deployed configuration of the device 1140 where the pusher 1151 is fully extended (to completely push/deploy the device 1140 outside of the catheter. This causes the atrial side of the arms to elastically revert back to original shape, thus capturing the mitral valve leaflets in the gaps 1147 and 1148. Note that the described deployment technique in FIGS. 79 to 81, can alternatively be similar to the technique described in FIGS. 12 to 15. Further, instead of pushing the device 1140 out of the catheter 1150, the user can alternatively hold the pusher 1151 in place and retract the catheter 1150 to deploy the device 1140.

FIGS. 82 to 85 show a variation of catheter based deployment of the device 1140 that allows for capture of the mitral valve leaflets one at a time. This is primarily achieved by using a catheter shaft configuration 1157 where, there is a designed step-indent 1155 at the distal end of the catheter shaft 1156, as seen in FIG. 85.

FIG. 82 is similar to FIG. 79, where in the device 1140 is elastically loaded into the catheter in a stretched configuration.

As the device 1140 is pushed out by the pusher 1151, one side of the ventricular arm 1144 elastically reverts to its original shape first, due to the cut aspect of the shaft 1155, while the other side of the ventricular arm 1140 remains in straight configuration owing to the constraint caused by the protruded shaft 1156, as shown in FIG. 83.

FIG. 84 shows the next stage of the deployment, where the device is pushed further out of the catheter, such that arm 1140 is unconstrained too by the catheter shaft 1156 and thereby reverts elastically to its original shape. This allows the user to capture the second mitral valve in the gap 1154.

FIG. 84 shows a deployed configuration of the device 1140, when it is fully pushed out of the catheter, similar to FIG. 81.

Note that with methods commonly used in the catheter/stent industry, it is possible to temporarily attach the device 1140 to the pusher 1151. Thereby, enabling the user to not only push but also be pull/retract the device 1140 inside the catheter 1157. Thus, providing means to bailout. The device can be fully deployed only if the user remotely disengages the device 1140 from the pusher 1151.

FIG. 94 shows an alternate embodiment of mitral valve spacer device 1210 that is made of two leaf springs joined using a structural rectangular tube 1207 fixed with any suitable and well known techniques such as crimp, weld, or with fasteners. These leaf springs can be made of laser cut sheet metal or strip (flat wire). Each sheet metal component as has an atrial side 1201 (or 1203) and a ventricular side 1202 (or 1204). The Atrial (and/or ventricle) side may have barbs 1214 (or frictional elements) to hold on to the leaflets in the spaces 1205 and 1206.

FIG. 95 shows 3D aspect of device 1210 shown in FIG. 94. (Note, the laser cut barbs 1214 are intended to be formed towards the gap 1205 (or 1206) to capture or secure the leaflets, however, they are shown in preformed shape due to CAD software limitations.).

FIGS. 96 to 98 show deployment of device 1210, similar to device 1140 as described in FIGS. 79 to 81.

FIGS. 104 to 111 show alternate embodiments of the spacer 1210 that are made from one continuous leaf spring. While differing in shapes and offering subtle variations, they function in general similar to spacer 1210

FIG. 112 shows an example of a closed cell body of the leaf spring spacer 1220. This is achieved by joining the leaf springs 1223 and 1225 at bottom 1221. A closed cell body offers higher structural strength in comparison to open cell structure. Both leaf springs 1223, 1225 may comprise anchors or frictional elements to secure mitral valve leaflets from the atrial side, while the leaf springs 1224, 1227 hold in place the leaflets from the ventricular side.

FIG. 113 shows the 3D aspect of the device 1220, as shown in FIG. 112.

FIG. 121 shows a schematic of the device 1220 as deployed in the mitral valve of the heart. Note that device 1220 may be deployed similar to the devices as explained previously with reference to FIGS. 96-103.

FIGS. 122 and 123 show a crescent shaped spacer embodiment 1250 with a notch 1252, 1253 on either sides. FIG. 124 shows a schematic of top view of a mitral valve and FIG. 125 shows schematic of the device 1250 seated inside the mitral valve. Not that the device 1250 can be any combination of flexible, elastic, rigid, solid, hollow and/or compressible. For example, in one embodiment the device 1250 can be straightened along the length and compressed along the height to allow for smaller diameter catheters. Further, the device 1250 may be paired with atrial and/or ventricular anchors as previously shown in various embodiments of the device 1000.

FIG. 132 shows an embodiment of spacer that is made of several segments that can be assembled within the cavities of the heart, preferably in the left atrium. The segments may be linked, bent, flexed, tied, hinged, wrapped in fabric or any other obvious methods can be used to join in a constrained and yet movable configuration. Each of the segments is loaded into a catheter in stretched/elongated configuration. As the segments are pushed out of the catheter, a string, wire, or suture 1273 is used to pull them together in a configuration of increasing thickness, as can be further seen in 3D schematic of the device in FIG. 133. One way to achieve this is by having a ball like anchor on the distal most termination of the suture 1273 and a movable anchor than can also me locked by the user once the device is fully out of the catheter and in the predetermined configuration. The movable anchor can then be locked and the excess proximal end of the suture cut to release and deploy the device 1270 as shown in FIG. 134.

FIG. 135 shows schematic of device 1270 being deployed in the left atrium via a trans-septal catheter. FIG. 136 shows the next stage where the suture is being used to assemble the device in desired configuration. FIG. 137 shows the final configuration where the device is deployed in the mitral valve. It additionally shows a variation in embodiment with additional atrial anchors 1281 and 1282 as well as ventricular anchors 1284 and 1285, similar to the anchors previously described and shown in FIG. 55.

One other obvious variation of device 1270 can be that all segments can be cut out of a single sheet of superelastic material such as nitinol and shape-set in its final configuration as in FIG. 134. Hence, when straightened and loaded into the delivery catheter, it self assembles in the predetermined shape-set configuration with or without the use of suture 1273, when pushed out of the catheter.

FIG. 138 shows a embodiment of annulus reshaping device 1330 that is deployed in the coronary great cardiac vein. As used herein, "coronary sinus" refers to not only the coronary sinus itself, but also to the venous system associated with the coronary sinus, including the great cardiac vein. This invention relates to a medical device and uses thereof that supports or changes the shape of tissue near a vessel in which the device is placed. This invention is particularly useful in reducing mitral valve regurgitation by changing the shape of or supporting a mitral valve annulus. U.S. Pat. No. 9,526,616 B2 describes a similar approach to cinch the annulus, however, that device uses wires and relies on expanding against the wall of the artery to secure either ends to generate cinching force. The expansion against the wall of the artery can be traumatic, further, the cinching wire can have a cheese cutter effect. This invention 1330 is based on using a wide atraumatic leaf-spring to cinch the annulus and uses atraumatic frictional elements to secure the ends. The wide surface area of the leaf spring mitigates the cheese cutter risk of a wire and the tiny barbs are atraumatic and yet can help secure the device in place with the desired cinching force. Further, owing to the elastic nature of the leaf spring, it can be configured to exert radial compression force on the annulus.

FIG. 139 shows the 3D aspect of the embodiment 1330 in FIG. 138. Atraumatic distal anchors or barbs 1332 and proximal anchors or barbs 1336 allow for cinching, while 1331 provides a larger surface area than a wire and additionally can be configure to exert radial compression force on the annulus.

FIGS. 140 and 141 show an alternate embodiment of annulus reshaping device 1330 that provides enhanced cinching and radial compression by using two partial leaf-springs. As can be seen in the FIGS. 140 and 141, 1344 and 1346 can translate on demand and locked in final cinched position as FIG. 141. Further, the overlapping of leaf-springs 1344 and 1346 can provide increased radial compression or force as a similarly designed single leaf-spring as shown in FIG. 139.

FIG. 142 shows yet another variation of annulus reshaping device that allows for improved cinching by elastic expansion and compression of 1348. While 1348 in shows one examples of pattern, other obvious patterns or combinations of patterns routinely used in the stent and medical device industry may be used.

FIG. 143 is a superior view of a heart 1350 with the atria removed. As pictured, the heart comprises several valves including mitral valve 1352, pulmonary valve 1354, aortic valve 1356 and tricuspid valve 1358. Mitral valve 1352 includes anterior cusp 1360, posterior cusp 1362 and annulus 1364. Annulus 1364 encircles cusps 1360 and 1362 and functions to maintain their respective spacing to ensure complete mitral valve closure during left ventricular contractions of the heart 1350. As illustrated, coronary sinus 1366 partially encircles mitral valve 1352 and is adjacent to mitral valve annulus 1364. Coronary sinus 1366 is part of the venous system of heart 1350 and extends along the AV groove between the left atrium and the left ventricle. This places coronary sinus 1366 essentially within the same plane as mitral valve annulus 1364, making coronary sinus 1366 available for placement of shaping device 1330 in order to reshape mitral valve geometry and to restore proper valve function.

FIG. 144 illustrates one possible embodiment of an intravascular tissue shaping device 1330 which is deployable in coronary sinus 1366. As illustrated in FIGS. 144 and 145, the device 1330 comprises of a leaf-spring with a distal anchor/barbs 1332 and a proximal anchor/barbs 1336. Both distal anchor 1332 and proximal anchor 1336 are shown in their deployed configurations, securely positioned within the coronary sinus 1366. FIG. 144 further depicts, in phantom, a delivery tool 1370 comprising catheter 1372 for delivering and positioning intravascular device 1330 in the coronary sinus 1366.

FIG. 146 illustrates one embodiment of delivering the intravascular device of the present invention to a desired location within a patient's body. An incision 1380 is made in the patient's skin to gain access to a blood vessel. The blood vessel may be, for example, the jugular vein. A guide catheter 1382 is advanced through the patient's vasculature until its distal end is positioned near the desired location for the intravascular device. After positioning the guide catheter 1382, a delivery catheter similar to a typical coaxial stent delivery catheter and advancing mechanism 1384 are inserted through the guide catheter 1382 to deploy the intra-vascular device at the desired location in the patient's body. In preferred embodiments, the delivery catheter is advanced until its distal end is inside the coronary sinus.

All implant embodiments described in this invention may be optionally coated to improve biocompatibility and tissue interface.

The coatings can be metallic or polymeric. Examples of metallic coatings are: Titanium, TiN, tantalum, gold, platinum. Examples of polymeric coatings are: Fluoropolymers: PTFE, PFA, FEP, ECTFE, ETFE, Parylene, polyester, PET, polypropylene, PEEK, PVDF, HDPE, LDPE, UHMWPE, Phosphorylcholine, hydroxyapatite, THV, CaP Biodegradable: poly(lactic acid), poly(glycolic acid)

All implant embodiments may be optionally covered to improve biocompatibility and tissue interface. The coverings can be metallic or polymeric. Additionally, the coverings can be fabric, web, fibrous, braid, woven or non-woven. Examples of metallic covering are: Titanium, tantalum, gold, platinum. Examples of polymeric coatings are: Fluoropolymers: PTFE, PFA, FEP, ECTFE, ETFE, Parylene, polyester, PET, polypropylene, PEEK, PVDF, HDPE, LDPE, UHMWPE, Phosphorylcholine, hydroxyapatite, CaP, THVBiodegradable: poly(lactic acid), poly(glycolic acid).

As evident to those skilled in the art, variations of embodiments may be formed by combining or substituting various aspects or features or subcomponents and/or parts of various exemplary embodiments described above. For example, a spacer anchor 14 in FIG. 1 may be replaced with single sided leaf-spring 1130 (FIG. 74), to form a new embodiment comprising of a leaf-spring 1130 and spacer body 12, wherein, the leaf-spring feature is attached to the spacer body 12.

As evident to those skilled in the art, variations of embodiments may be formed by combining or substituting various aspects or features or subcomponents and/or parts of various exemplary embodiments described above. For example, a spacer anchor 14 (FIG. 1) may be replaced with two or more single sided leaf-spring devices 1130 (FIG. 74), to form a new embodiment comprising of a leaf-springs 1130 and spacer body 12, wherein, two or more leaf-spring 1130 features are used to attach the spacer body 12 to the same leaflet or multiple leaflets. For example, two leaf-springs 1130 may be used to attach to the anterior and posterior leaflets with the spacer body 12 sandwiched in between to prevent the regurgitation.

As evident to those skilled in the art, variations of embodiments may be formed by combining or substituting various aspects or features or subcomponents, raw materials and/or parts of various exemplary embodiments described above. For example, the intent of exemplary leaf-spring 1130 embodiment as shown in FIG. 74 can be designed using round or rectangular or any other geometric shape wires. Further, the leaf-spring made of wires can comprise of a single wire or multiple wires or loops of wires mechanically attached together to achieve a configuration that is similar in function to the exemplary leaf-spring 1130 embodiment.

A one skilled in the art would appreciate the various examples and embodiments and aspects described and claimed herein can be combined in part or in whole throughout this application.

The following is a listing of the reference numbers used in this application:
  2 Left atrium
  4 Left ventricle
  6 Anterior mitral valve leaflet
  8 Posterior mitral valve leaflet
  10 An exemplary embodiment of a single leaflet attaching spacer device
  12 Body of the exemplary device 10
  14 Anchor of the embodiment 10
  20 An exemplary embodiment of a single leaflet attaching device with atrial anchor
  22 Body of the exemplary device 20
  24 Ventricular anchor of the embodiment 20
  26 Atrial anchor of the embodiment 20
  26A Comprised lattice-type framework of anchor 26
  26B Comprised single elongated loop of 26
  26C Comprised lattice-type framework with many diamond shaped segments of anchor 26
  27 Connecting members of the atrial anchor 26C to the body 22
  28 Blood-impervious fabric cover
  29 Diamond-shaped segments attached to the atrial anchor 26C
  30 Pointing tips at the ends of each diamond shaped segment 29
  32 Annular metal frame covered with fabric 28 found on the body 22
  50 An exemplary embodiment of single leaflet attaching device
  52 Body of the exemplary device 50
  54 Anchor of the embodiment 50
  56 Delivery catheter for device 50
  58 Distal outlet of the catheter 56
  59 Member to push device 50 distally relative to the catheter 56
  60 Gap between the curling anchor 54 and the body 52 where the mitral leaflet will be 62 Ventricular end of the body 52
100 An exemplary embodiment of single leaflet attaching device
102 Anchor of the embodiment 100
104 Delivery catheter for device 100
106 Distal end portion of catheter 104
110 Inferior vena cava
112 Right atrium
114 Septum
116 Pusher member extending coaxially through catheter 104
120 An exemplary embodiment of single leaflet attaching device
122 Anchor of the embodiment 120
124 Delivery device for device 120
126 Apex
600 An exemplary embodiment of double leaflet attaching spacer device
602 Body of the exemplary device 600
604 First anchor of the embodiment 600
606 Second anchor of the embodiment 600
608 First inner portion of anchors 604, 606
610 Second inner portion of anchors 604, 606
612 First bottom portion of anchors 604, 606
614 Second bottom portion of anchors 604, 606
616 Main loop portion of anchors 604, 606
618 One of the divided mitral value orifices during diastole
620 Other divided mitral value orifice during diastole
660 An exemplary embodiment of dual-anchor spacer device
662 One of the divided native mitral valve orifices during diastole
664 Other divided native mitral valve orifice during diastole
666 Leaflets which permit blood flow between left ventricle and left atrium
700 An exemplary embodiment of tricuspid spacer device
702 Three anchors of embodiment 700
704 Leaflet of the tricuspid valve
706 One of three orifices allowing blood flow between right atrium and right ventricle
708 Second orifice between right atrium and right ventricle
710 Third orifice between right atrium and right ventricle
712 Circular body of the exemplary device 700
720 Alternative embodiment of tricuspid spacer device
722 Y-shaped body of the device 720
724 Three clips of the embodiment 720
730 Alternative embodiment of tricuspid spacer device
732 Triangular-shaped body of the device 730
734 Three clips of the embodiment 730
750 An exemplary embodiment of dual anchor spacer device
752 Body of the exemplary device 750
754 First anchor of the embodiment 750
756 Second anchor of the embodiment 750
758 One of two openings for blood to flow from left atrium to left ventricle during diastole
760 Second opening for blood flow from left atrium to left ventricle
800 An exemplary embodiment of dual anchor spacer device
802 Body of the exemplary device 800
804 First anchor of the embodiment 800
806 Second anchor of the embodiment 800
808 Interconnected struts on the body 802
810 First end portion of the first anchor 804
812 Second end portion of the first anchor 804
814 Loop portion extending between the first and second end portions 810, 812
816 First end portion of the body 802
818 Second end portion of the body 802
820 Coupling mechanisms on the body 802
822 Fabric material for the spacer 800
824 Fabric layer covering all of the opening at the center of the body 802
870 Delivery device for the spacer 800
872 Inner sheath of delivery device 870
874 Outer sheath of the delivery device 870
876 Expanders to force the anchors 804, 806 to splay apart
920 Delivery system for device 800 to the region of a patient's mitral valve
922 Outer sheath of the delivery system 920
924 Inner sheath of the delivery system 920
930 Guidewire which can extend through the outer sheath 922 and inner sheath 924
1000 An exemplary embodiment of prosthetic device with various anchors configurations
1001 Looped atrial support structure of device 1000
1002 Looped atrial support structure of device 1000
1003 Ventricular support structure of device 1000
1004 Ventricular support structure of device 1000
1005 Ventricular support structure of device 1000
1009 Body of the exemplary device 1000
1010 Atrial side of the body 1009
1011 Ventricular side of the body 1009
1012 Support structure originating from the tip of the body 1009
1014 Support structure originating from the tip of the body 1009
1015 Support structures from the body 1009
1016 Support structures from the body 1009
1017 Support structures from the body 1009
1018 Support structures from the body 1009
1021 Support structures originating from various staggered locations of the body 1009
1022 Support structures originating from various staggered locations of the body 1009
1023 Support structures originating from various staggered locations of the body 1009
1024 Support structures originating from various staggered locations of the body 1009
1025 Support structures originating from various staggered locations of the body 1009
1026 Support structures originating from various staggered locations of the body 1009
1030 Support structure of device 1000
1031 Support structure of device 1000
1032 Location of the annulus along the length of the body 1009
1037 Closed loop form of support structure at location 1032
1038 Close loop form of support structure at location 1032
1051 Crimp used to string two embodiments 1000 together
1052 Crimp used to string two embodiments 1000 together
1061 String running through two embodiments 1000 to hold together
1062 String running through two embodiments 1000 to hold together 1063 String running through two embodiments 1000 to hold together
1064 String running through two embodiments 1000 to hold together
1065 Excess string after the crimp 1052
1070 Alternative embodiment of device 1000
1072 Starting string running through two embodiments 1070
1073 End of string running through two embodiments 1070 before the crimp 1052
1074 Excess string after the locked proximal crimp 1052
1079 Non-circular body of an alternative embodiment 1070
1080 An exemplary embodiment based on balloons as spacers
1082 Self-sealing ends for the embodiment 1080
1083 Retrieval loop at one or both ends of the device 1080, 1100
1084 The body of the balloon for the exemplary device 1080
1086 Ventricular support/anchor structure of the embodiment 1080
1088 Detachable inflation shaft of the embodiment 1080
1090 Alternative embodiment of single balloon design with a wide compliant body shape
1094 Balloon body of the embodiment 1090
1100 Alternative embodiment with stent-like structure
1101 Atrial support structure of the device 1100
1102 Spacer body of the exemplary device 1100
1103 Ventricular side of body 1102
1130 An exemplary embodiment of a prosthetic device with leaf springs
1131 Leaf spring of the device 1130 at the base
1140 An exemplary embodiment of device using two devices 1130
1141 Atrial leaf-spring of device 1130
1142 Ventricular leaf-spring of the device 1130
1143 Atrial leaf-spring of device 1140 opposite of the atrial leaf-spring 1141
1144 Ventricular leaf-spring of device 1140 opposite of the ventricular leaf-spring 1142
1145 Tubular member binding two devices 1130 to form device 1140
1146 Atrial frictional elements of the device 1130
1147 Gap where leaflets remain anchored at natural shape of device 1140
1148 Gap opposite of the other gap 1147 to keep leaflets anchored
1149 Fastening hole at the base of the device 1130, as shown in FIG. 76
1150 Delivery catheter for the device 1140
1151 Pusher member to push the device 1150
1153 Gap between atrial and ventricular leaf-springs during configuration of device 1140
1154 Gap opposite of other gap 1153 during configuration
1155 Trailing end of the catheters 1150 and 1157
1156 Leading distal end of the catheters 1150 and 1157
1157 Alternative delivery catheter for device 1140
1164 Anterior mitral valve leaflet of the heart
1167 Posterior mitral valve leaflet of the heart
1170 An exemplary embodiment of prosthetic device with leaf springs and wire loops
1171 Tubular member at the base of device 1170
1172 Frictional barbs on the leaf springs of the device 1170
1173 Atrial leaf spring of the device 1170
1174 Ventricular wire loop of the device 1170
1175 Leaf spring opposite of leaf spring 1173
1177 Wire loop opposite of the wire loop 1174
1200 An exemplary embodiment of prosthetic device with body and anchor leaf springs
1201 Body leaf spring of the device 1200
1202 Anchor leaf spring of the device 1200
1203 Other body leaf spring opposite of body leaf spring 1201
1204 Other anchor leaf spring opposite of anchor leaf spring 1202 (not in device 1200)
1205 Gap between the body leaf spring 1201 and anchor leaf spring 1202
1206 Gap between the body leaf spring 1203 and anchor leaf spring 1204
1207 Tubular structure holding the two body leaf springs of device 1200 together
1208 Base structure holding opposite leaf springs of device 1200
1209 Atrial support structure of device 1200
1210 Alternative embodiment of device 1200 with anchor leaf spring 1204
1211 Base gap between opposite leaf springs of device 1210 (without 1208)
1212 Delivery catheter for device 1210
1213 Pusher member for the device 1210
1214 Frictional barbs for leaflets of device 1210 to be more secure
1215 Alternative delivery catheter for device 1210
1216 Leading end of the catheter 1215
1217 Trailing end of the catheter 1215
1220 Example embodiment of a leaf spring spacer
1221 Bottom location where the body leaf anchor springs join
1223 Body leaf spring of device 1220
1224 Anchor leaf spring of the device 1220
1225 Other body leaf spring opposite of leaf spring 1223
1227 Other anchor leaf spring opposite of leaf spring 1224
1231 Closed cell leaf spring spacer
1232 Open cell leaf spring spacer
1234 Location where leaf springs are bonded in FIG. 114
1250 An exemplary embodiment of a crescent shaped spacer device
1252 Notch on one side of the device 1250
1253 Other notch opposite of the notch 1252
1254 Looped support member on the atrial side of the device 1250
1255 Looped support member on the atrial side of the device 1250
1256 Looped support member on the atrial side of the device 1250
1264 Alternative support member on the atrial side of device 1250
1265 Alternative support member on the atrial side of device 1250
1266 Alternative support member on the atrial side of device 1250
1269 Annulus anchors of device 1250
1270 An exemplary embodiment of spacer device
1272 Delivery catheter for device 1270
1273 Suture used to pull segments of device 1270 through catheter
1274 Body of the embodiment 1270
1276 Ball-like anchor on distal end of the suture 1273
1277 Movable anchor on the other end of the suture 1273
1281 Atrial anchor of the device 1270
1282 Atrial anchor opposite of the anchor 1281

1284 Ventricular anchor of the device 1270
1285 Ventricular anchor opposite of the anchor 1285
1330 An exemplary embodiment of annulus reshaping device
1331 Wide atraumatic leaf-spring for the device 1330
1332 Frictional members of the device 1330 to secure one end
1336 Other frictional members opposite of the members 1332
1338 Hole at one end of the device 1330
1339 Other hole opposite of hole 1338
1340 Alternative embodiment of annulus reshaping device 1330
1341 The compression path for device 1340
1344 One of the overlapping leaf-springs for device 1340
1346 The other leaf-spring opposite of leaf-spring 1344
1348 Alternative stretchable leaf spring for device 1340
1350 Superior view of the heart with atria removed
1352 Mitral value
1354 Pulmonary valve
1356 Aortic valve
1358 Tricuspid valve
1360 Anterior cusp at the mitral valve 1352
1362 Posterior cusp at the mitral valve 1352
1364 Annulus at the mitral valve 1352
1366 Coronary sinus partially encircling mitral valve 1352
1370 Delivery tool for the device 1330 and catheter 1372
1372 Catheter used to deliver and position device 1330 in the coronary sinus 1366
1380 Incision in patient's skin to a blood vessel
1382 Guide catheter
1384 Delivery catheter inserted through the guide catheter 1382

Although certain embodiments of the disclosure have been described in detail, certain variations and modifications will be apparent to those skilled in the art, including embodiments or examples or clauses that may not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. For example, some of the embodiments described specifically for mitral valve repair can easily be modified or configured for use of tricuspid valve. Thus, it is intended that the scope of the present disclosure herein disclosed should not be limited by the particular disclosed embodiments or examples described above. For all of the embodiments and examples described above, the steps of any methods need not be performed sequentially. Lastly, the terms implant, device, leaf-spring, sheet, spacer and/or prosthetic device may be used interchangeably.

What is claimed is:

1. A prosthetic sealing device comprising:
a leaf-spring having a atrial leaf-spring segment and a ventricular leaf-spring segment, the segments being joined at a base and configured to open in response to an opening force to form to a leaflet-receiving gap and to resiliently close toward each other when the opening force is removed; and
a body attached to the base of the leaf-spring, wherein the body is configured to expand to inhibit the flow of blood through the body;
wherein the body comprises any one of (a) a hollowed shaft, wherein the shaft is flexible and/or foldable, (b) a sponge-like material that is compressible and flexible, (c) a gel-like material, and (d) a balloon connected to an inflator for remotely inflating the balloon to allow size adjustment after implantation.

2. A prosthetic sealing device comprising:
a leaf-spring having a atrial leaf-spring segment and a ventricular leaf-spring segment, the segments being joined at a base and configured to open in response to an opening force to form to a leaflet-receiving gap and to resiliently close toward each other when the opening force is removed; and
a body attached to the base of the leaf-spring, wherein the body is configured to expand to inhibit the flow of blood through the body;
wherein the body and the leaf springs are covered or coated with a material that promotes tissue in-growth.

3. The prosthetic sealing device of claim 2, wherein the tissue in-growth promoting material comprises a polyester fabric.

4. The prosthetic sealing device of claim 1, wherein the leaf-springs comprise atraumatic barbs to securely grasp leaflets.

5. The prosthetic sealing device of claim 1, wherein the leaf-springs and body comprise a shape memory and/or super-elastic material.

6. The prosthetic sealing device of claim 5, wherein the shape memory or super-elastic material comprises a nickel-titanium alloy.

7. A prosthetic sealing device comprising:
a leaf-spring having a atrial leaf-spring segment and a ventricular leaf-spring segment, the segments being joined at a base and configured to open in response to an opening force to form to a leaflet-receiving gap and to resiliently close toward each other when the opening force is removed;
a body attached to the base of the leaf-spring, wherein the body is configured to expand to inhibit the flow of blood through the body; and
a second set of leaf springs that are configured to secure both anterior and posterior leaflets, with the body attached in between or at a side of the leaf springs.

8. The prosthetic sealing device of claim 7, further comprising a third set of leaf springs configured to secure each of the three tricuspid valve leaflets, with the body attached in between or at a side of the leaf-springs.

9. A prosthetic sealing device comprising:
a leaf-spring having a atrial leaf-spring segment and a ventricular leaf-spring segment, the segments being joined at a base and configured to open in response to an opening force to form to a leaflet-receiving gap and to resiliently close toward each other when the opening force is removed;

a body attached to the base of the leaf-spring, wherein the body is configured to expand to inhibit the flow of blood through the body; and two or more sets of leaf springs that are configured to secure a single leaflet.

10. A prosthetic sealing device comprising:

a leaf-spring having a atrial leaf-spring segment and a ventricular leaf-spring segment, the segments being joined at a base and configured to open in response to an opening force to form to a leaflet-receiving gap and to resiliently close toward each other when the opening force is removed;

a body attached to the base of the leaf-spring, wherein the body is configured to expand to inhibit the flow of blood through the body; and a retrieval feature configured to allow for retrieval of the prosthetic device during and/or after implantation.

11. The prosthetic sealing of device of claim 10, wherein the prosthetic device is covered or coated with materials that inhibit formation of scar/fibrous tissue.

* * * * *